(12) United States Patent
Tanzi et al.

(10) Patent No.: US 8,273,543 B2
(45) Date of Patent: *Sep. 25, 2012

(54) REGULATION OF BACE DEGRADATION

(75) Inventors: Rudolph E. Tanzi, Hull, MA (US); Giuseppina Tesco, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/861,912

(22) Filed: Aug. 24, 2010

(65) Prior Publication Data

US 2011/0177543 A1 Jul. 21, 2011

Related U.S. Application Data

(63) Continuation of application No. 11/827,445, filed on Jul. 11, 2007, now Pat. No. 7,781,177.

(60) Provisional application No. 60/819,832, filed on Jul. 11, 2006.

(51) Int. Cl.
G01N 33/567 (2006.01)

(52) U.S. Cl. ....................................... 435/7.21

(58) Field of Classification Search .................. None
See application file for complete search history.

(56) References Cited

U.S. PATENT DOCUMENTS 7,781,177 B2  8/2010  Tanzi et al.

OTHER PUBLICATIONS

Abe, K., Tanzi, R. E., and Kogure, K. (1991). Selective induction of Kunitz-type protease inhibitor domain-containing amyloid precursor protein mRNA after persistent focal ischemia in rat cerebral cortex. Neurosci Lett 125, 172-174.
Abrahamson, E. E., Ikonomovic, M. D., Ciallella, J. R., Hope, C. E., Paljug, W. R., Isanski, B. A., Flood, D. G., Clark, R. S., and Dekosky, S. T. (2006). Caspase inhibition therapy abolishes brain trauma-induced increases in Abeta peptide: Implications for clinical outcome. Exp Neurol 197, 437-450.
Banati, R. B., Gehrmann, J., Wiessner, C., Hossmann, K. A., and Kreutzberg, G. W. (1995). Glial expression of the beta-amyloid precursor protein (APP) in global ischemia. J Cereb Blood Flow Metab 15, 647-654.
Barnes, N. Y., Li, L., Yoshikawa, K., Schwartz, L. M., Oppenheim, R. W., and Milligan, C. E. (1998). Increased production of amyloid precursor protein provides a substrate for caspase-3 in dying motoneurons. J Neurosci 18, 5869-5880.
Blasko, I., Beer, R., Bigl, M., Apelt, J., Franz, G., Rudzki, D., Ransmayr, G., Kampfl, A., and Schliebs, R. (2004). Experimental traumatic brain injury in rats stimulates the expression, production and activity of Alzheimer's disease beta-secretase (BACE-1). J Neural Transm 111, 523-536.
Bonifacino, J. S. (2004). The GGA proteins: adaptors on the move. Nat Rev Mol Cell Biol 5, 23-32.
Bonifacino, J. S., and Traub, L. M. (2003). Signals for sorting of transmembrane proteins to endosomes and lysosomes. Annu Rev Biochem 72, 395-447.
Brancolini, C., Sgorbissa, A., and Schneider, C. (1998). Proteolytic processing of the adherens junctions components beta-catenin and gamma-catenin/plakoglobin during apoptosis. Cell Death Differ 5, 1042-1050.
Chen, X. H., Siman, R., Iwata, A., Meaney, D. F., Trojanowski, J. Q., and Smith, D. H. (2004). Long-term accumulation of amyloid-beta, beta-secretase, presenilin-1, and caspase-3 in damaged axons following brain trauma. Am J Pathol 165, 357-371.
Citron, M. (2004). Beta-secretase inhibition for the treatment of Alzheimer's disease—promise and challenge. Trends Pharmacol Sci 25, 92-97.
Cribbs, D. H., Poon, W. W., Rissman, R. A., and Blurton-Jones, M. (2004). Caspase mediated degeneration in Alzheimer's disease. Am J Pathol 165, 353-355.
Davoli, M. A., Fourtounis, J., Tam, J., Xanthoudakis, S., Nicholson, D., Robertson, G. S., Ng, G. Y., and Xu, D. (2002). Immunohistochemical and biochemical assessment of caspase-3 activation and DNA fragmentation following transient focal ischemia in the rat. Neuroscience 115, 125-136.
De Strooper, B., and Annaert, W. (2000). Proteolytic processing and cell biological functions of the amyloid precursor protein. J Cell Sci 113 (Pt 11), 1857-1870.
Fukumoto, H., Cheung, B. S., Hyman, B. T., and Irizarry, M. C. (2002). Beta-secretase protein and activity are increased in the neocortex in Alzheimer disease. Arch Neurol 59, 1381-1389.
Galli, C., Piccini, A., Ciotti, M. T., Castellani, L., Calissano, P., Zaccheo, D., and Tabaton, M. (1998). Increased amyloidogenic secretion in cerebellar granule cells undergoing apoptosis. Proc Natl Acad Sci U S A 95, 1247-1252.
Gervais, F. G., Xu, D., Robertson, G. S., Vaillancourt, J. P., Zhu, Y., Huang, J., LeBlanc, A., Smith, D., Rigby, M., Shearman, M. S., et al. (1999). Involvement of caspases in proteolytic cleavage of Alzheimer's amyloid-beta precursor protein and amyloidogenic A beta peptide formation. Cell 97, 395-406.
Grupe, A., Li, Y., Rowland, C., Nowotny, P., Hinrichs, A. L., Smemo, S., Kauwe, J. S., Maxwell, T. J., Cherny, S., Doil, L., et al. (2006). A scan of chromosome 10 identifies a novel locus showing strong association with late-onset Alzheimer disease. Am J Hum Genet 78, 78-88.
Guo, Q., Xie, J., Chang, X., and Du, H. (2001). Prostate apoptosis response-4 enhances secretion of amyloid beta peptide 1-42 in human neuroblastoma IMR-32 cells by a caspase-dependent pathway. J Biol Chem 276, 16040-16044.
He, X., Chang, W. P., Koelsch, G., and Tang, J. (2002). Memapsin 2 (beta-secretase) cytosolic domain binds to the VHS domains of GGA1 and GGA2: implications on the endocytosis mechanism of memapsin 2. FEBS Lett 524, 183-187.
He, X., Li, F., Chang, W. P., and Tang, J. (2005). GGA proteins mediate the recycling pathway of memapsin 2 (BACE). J Biol Chem. 280(12), 11696-11703.

(Continued)

Primary Examiner — Daniel E Kolker
Assistant Examiner — Gregory S Emch
(74) Attorney, Agent, or Firm — Wolf, Greenfield & Sacks, P.C.

(57) ABSTRACT

The invention relates to methods and products for diagnosing, preventing, and treating Alzheimer's disease and abnormal production of amyloid β.

20 Claims, 38 Drawing Sheets

OTHER PUBLICATIONS

He, X., Zhu, G., Koelsch, G., Rodgers, K. K., Zhang, X. C., and Tang, J. (2003). Biochemical and structural characterization of the interaction of memapsin 2 (beta-secretase) cytosolic domain with the VHS domain of GGA proteins. Biochemistry 42, 12174-12180.

Holsinger, R. M., McLean, C. A., Beyreuther, K., Masters, C. L., and Evin, G. (2002). Increased expression of the amyloid precursor beta-secretase in Alzheimer's disease. Ann Neurol 51, 783-786.

Honig, L. S., Tang, M. X., Albert, S., Costa, R., Luchsinger, J., Manly, J., Stern, Y., and Mayeux, R. (2003). Stroke and the risk of Alzheimer disease. Arch Neurol 60, 1707-1712.

Huse, J. T., Pijak, D. S., Leslie, G. J., Lee, V. M., and Doms, R. W. (2000). Maturation and endosomal targeting of beta-site amyloid precursor protein-cleaving enzyme. The Alzheimer's disease beta-secretase. J Biol Chem 275, 33729-33737.

Kalaria, R. N. (2000). The role of cerebral ischemia in Alzheimer's disease. Neurobiol Aging 21, 321-330.

Kalaria, R. N., Bhatti, S. U., Palatinsky, E. A., Pennington, D. H., Shelton, E. R., Chan, H. W., Perry, G., and Lust, W. D. (1993). Accumulation of the beta amyloid precursor protein at sites of ischemic injury in rat brain. Neuroreport 4, 211-214.

Kim, H. S., Lee, S. H., Kim, S. S., Kim, Y. K., Jeong, S. J., Ma, J., Han, D. H., Cho, B.K., and Suh, Y. H. (1998). Post-ischemic changes in the expression of Alzheimer's APP isoforms in rat cerebral cortex. Neuroreport 9, 533-537.

Koh, Y. H., Suzuki, K., Che, W., Park, Y. S., Miyamoto, Y., Higashiyama, S., and Taniguchi, N. (2001). Inactivation of glutathione peroxidase by NO leads to the accumulation of H2O2 and the induction of HB-EGF via c-Jun NH2-terminal kinase in rat aortic smooth muscle cells. Faseb J 15, 1472-1474.

Koh, Y. H., von Arnim, C. A., Hyman, B. T., Tanzi, R. E., and Tesco, G. (2005). BACE is degraded via the lysosomal pathway. J Biol Chem 280, 32499-32504.

Koistinaho, J., Pyykonen, I., Keinanen, R., and Hokfelt, T. (1996). Expression of beta amyloid precursor protein mRNAs following transient focal ischaemia. Neuroreport 7, 2727-2731.

Lane, J. D., Lucocq, J., Pryde, J., Barr, F. A., Woodman, P. G., Allan, V. J., and Lowe, M. (2002). Caspase-mediated cleavage of the stacking protein GRASP65 is required for Golgi fragmentation during apoptosis. J Cell Biol 156, 495-509.

LeBlanc, A. (1995). Increased production of 4 kDa amyloid beta peptide in serum deprived human primary neuron cultures: possible involvement of apoptosis. J Neurosci 15, 7837-7846.

LeBlanc, A., Liu, H., Goodyer, C., Bergeron, C., and Hammond, J. (1999). Caspase-6 role in apoptosis of human neurons, amyloidogenesis, and Alzheimer's disease. J Biol Chem 274, 23426-23436.

LeBlanc, A. C. (2005). The role of apoptotic pathways in Alzheimer's disease neurodegeneration and cell death. Curr Alzheimer Res 2, 389-402.

Li, R., Lindholm, K., Yang, L. B., Yue, X., Citron, M., Yan, R., Beach, T., Sue, L., Sabbagh, M., Cai, H., et al. (2004). Amyloid beta peptide load is correlated with increased beta-secretase activity in sporadic Alzheimer's disease patients. Proc Natl Acad Sci U S A 101, 3632-3637.

Li, Y., Nowotny, P., Holmans, P., Smemo, S., Kauwe, J. S., Hinrichs, A. L., Tacey, K., Doil, L., van Luchene, R., Garcia, V., et al. (2004). Association of late-onset Alzheimer's disease with genetic variation in multiple members of the GAPD gene family. Proc Natl Acad Sci U S A 101, 15688-15693.

Li, Y., Grupe, A., Rowland, C., Nowotny, P., Kauwe, J. S., Smemo, S., Hinrichs, A., Tacey, K., Toombs, T. A., Kwok, S., et al. (2006). DAPK1 variants are associated with Alzheimer's disease and allele-specific expression. Hum Mol Genet 15, 2560-2568.

Liu, R., Yang, S. H., Perez, E., Yi, K. D., Wu, S. S., Eberst, K., Prokai, L., Prokai-Tatrai, K., Cai, Z. Y., Covey, D. F., et al. (2002). Neuroprotective effects of a novel non-receptorbinding estrogen analogue: in vitro and in vivo analysis. Stroke 33, 2485-2491.

Namura, S., Zhu, J., Fink, K., Endres, M., Srinivasan, A., Tomaselli, K. J., Yuan, J., and Moskowitz, M. A. (1998). Activation and cleavage of caspase-3 in apoptosis induced by experimental cerebral ischemia. J Neurosci 18, 3659-3668.

Nolan, K. A., Lino, M. M., Seligmann, A. W., and Blass, J. P. (1998). Absence of vascular dementia in an autopsy series from a dementia clinic. J Am Geriatr Soc 46, 597-604.

Pastorino, L., Ikin, A. F., Nairn, A. C., Pursnani, A., and Buxbaum, J. D. (2002). The carboxyl-terminus of BACE contains a sorting signal that regulates BACE trafficking but not the formation of total A(beta). Mol Cell Neurosci 19, 175-185.

Pellegrini, L., Passer, B. J., Tabaton, M., Ganjei, J. K., and D'Adamio, L. (1999). Alternative, non-secretase processing of Alzheimer's beta-amyloid precursor protein during apoptosis by caspase-6 and -8. J Biol Chem 274, 21011-21016.

Petrovitch, H., Ross, G. W., Steinhorn, S. C., Abbott, R. D., Markesbery, W., Davis, D., Nelson, J., Hardman, J., Masaki, K., Vogt, M. R., et al. (2005). AD lesions and infarcts in demented and non-demented Japanese-American men. Ann Neurol 57, 98-103.

Puertollano, R., and Bonifacino, J. S. (2004). Interactions of GGA3 with the ubiquitin sorting machinery. Nat Cell Biol 6, 244-251.

Puertollano, R., Randazzo, P. A., Presley, J. F., Hartnell, L. M., and Bonifacino, J. S. (2001). The GGAs promote ARF-dependent recruitment of clathrin to the TGN. Cell 105, 93-102.

Qing, H., Zhou, W., Christensen, M. A., Sun, X., Tong, Y., and Song, W. (2004). Degradation of BACE by the ubiquitin-proteasome pathway. Faseb J. express article 10.1096/fj.04-1994fje. Published online Aug. 2, 2004.

Riekse, R. G., Leverenz, J. B., McCormick, W., Bowen, J. D., Teri, L., Nochlin, D., Simpson, K., Eugenio, C., Larson, E. B., and Tsuang, D. (2004). Effect of vascular lesions on cognition in Alzheimer's disease: a community-based study. J Am Geriatr Soc 52, 1442-1448.

Rippon, G. A., Tang, M. X., Lee, J. H., Lantigua, R., Medrano, M., and Mayeux, R. (2006). Familial Alzheimer disease in Latinos: interaction between APOE, stroke, and estrogen replacement. Neurology 66, 35-40.

Sena-Esteves, M., Tebbets, J. C., Steffens, S., Crombleholme, T., and Flake, A. W. (2004). Optimized large-scale production of high titer lentivirus vector pseudotypes. J Virol Methods 122, 131-139.

Shi, J., Yang, S. H., Stubley, L., Day, A. L., and Simpkins, J. W. (2000). Hypoperfusion induces overexpression of beta-amyloid precursor protein mRNA in a focal ischemic rodent model. Brain Res 853, 1-4.

Shiba, T., Kametaka, S., Kawasaki, M., Shibata, M., Waguri, S., Uchiyama, Y., and Wakatsuki, S. (2004). Insights into the phosphoregulation of beta-secretase sorting signal by the VHS domain of GGA1. Traffic 5, 437-448.

Sinha, S., Anderson, J. P., Barbour, R., Basi, G. S., Caccavello, R., Davis, D., Doan, M., Dovey, H. F., Frigon, N., Hong, J., et al. (1999). Purification and cloning of amyloid precursor protein beta-secretase from human brain. Nature 402, 537-540.

Snowdon, D. A., Greiner, L. H., Mortimer, J. A., Riley, K. P., Greiner, P. A., and Markesbery, W. R. (1997). Brain infarction and the clinical expression of Alzheimer disease. The Nun Study. JAMA 277, 813-817.

Sodhi, C. P., Rampalli, S., Perez, R. G., Koo, E. H., Quinn, B., and Gottardi-Littell, N. R. (2004). The endocytotic pathway is required for increased A beta 42 secretion during apoptosis. Brain Res Mol Brain Res 128, 201-211.

Stephenson, D. T., Rash, K., and Clemens, J. A. (1992). Amyloid precursor protein accumulates in regions of neurodegeneration following focal cerebral ischemia in the rat. Brain Res 593, 128-135.

Tamagno, E., Bardini, P., Obbili, A., Vitali, A., Borghi, R., Zaccheo, D., Pronzato, M. A., Danni, O., Smith, M. A., Perry, G., and Tabaton, M. (2002). Oxidative stress increases expression and activity of BACE in NT2 neurons. Neurobiol Dis 10, 279-288.

Tamagno, E., Guglielmotto, M., Bardini, P., Santoro, G., Davit, A., Di Simone, D., Danni, O., and Tabaton, M. (2003). Dehydroepiandrosterone reduces expression and activity of BACE in NT2 neurons exposed to oxidative stress. Neurobiol Dis 14, 291-301.

Tamagno, E., Parola, M., Bardini, P., Piccini, A., Borghi, R., Guglielmotto, M., Santoro, G., Davit, A., Danni, O., Smith, M. A., et al. (2005). Beta-site APP cleaving enzyme upregulation induced by 4-hydroxynonenal is mediated by stress-activated protein kinases pathways. J Neurochem 92, 628-636.

Tesco, G., Koh, Y. H., and Tanzi, R. E. (2003). Caspase activation increases beta-amyloid generation independently of caspase cleavage of the beta-amyloid precursor protein (APP). J Biol Chem 278, 46074-46080.

Tong, Y., Zhou, W., Fung, V., Christensen, M. A., Qing, H., Sun, X., and Song, W. (2005). Oxidative stress potentiates BACE1 gene expression and Abeta generation. J Neural Transm 112, 455-469.

Tyler, S. J., Dawbarn, D., Wilcock, G. K., and Allen, S. J. (2002). alpha- and betasecretase: profound changes in Alzheimer's disease. Biochem Biophys Res Commun 299, 373-376.

Vassar, R., Bennett, B. D., Babu-Khan, S., Kahn, S., Mendiaz, E. A., Denis, P., Teplow, D. B., Ross, S., Amarante, P., Loeloff, R., et al. (1999). Beta-secretase cleavage of Alzheimer's amyloid precursor protein by the transmembrane aspartic protease BACE. Science 286, 735-741.

Velliquette, R. A., O'Connor, T., and Vassar, R. (2005). Energy inhibition elevates beta-secretase levels and activity and is potentially amyloidogenic in APP transgenic mice: possible early events in Alzheimer's disease pathogenesis. J Neurosci 25, 10874-10883.

Von Arnim, C. A., Tangredi, M. M., Peltan, I. D., Lee, B. M., Irizarry, M. C., Kinoshita, A., and Hyman, B. T. (2004). Demonstration of BACE (beta-secretase) phosphorylation and its interaction with GGA1 in cells by fluorescence-lifetime imaging microscopy. J Cell Sci 117, 5437-5445.

Wahle, T., Prager, K., Raffler, N., Haass, C., Famulok, M., and Walter, J. (2005). GGA proteins regulate retrograde transport of BACE1 from endosomes to the trans-Golgi network. Mol Cell Neurosci 29, 453-461.

Wakita, H., Tomimoto, H., Akiguchi, I., Ohnishi, K., Nakamura, S., and Kimura, J. (1992). Regional accumulation of amyloid beta/A4 protein precursor in the gerbil brain following transient cerebral ischemia. Neurosci Lett 146, 135-138.

Weidemann, A., Paliga, K., Durrwang, U., Reinhard, F. B., Schuckert, O., Evin, G., and Masters, C. L. (1999). Proteolytic processing of the Alzheimer's disease amyloid precursor protein within its cytoplasmic domain by caspase-like proteases. J Biol Chem 274, 5823-5829.

Wen, Y., Onyewuchi, O., Yang, S., Liu, R., and Simpkins, J. W. (2004). Increased beta-secretase activity and expression in rats following transient cerebral ischemia. Brain Res 1009, 1-8.

Yan, R., Bienkowski, M. J., Shuck, M. E., Miao, H., Tory, M. C., Pauley, A. M., Brashier, J. R., Stratman, N. C., Mathews, W. R., Buhl, A. E., et al. (1999). Membrane-anchored aspartyl protease with Alzheimer's disease beta-secretase activity. Nature 402, 533-537.

Yang, L. B., Lindholm, K., Yan, R., Citron, M., Xia, W., Yang, X. L., Beach, T., Sue, L., Wong, P., Price, D., et al. (2003). Elevated beta-secretase expression and enzymatic activity detected in sporadic Alzheimer disease. Nat Med 9, 3-4.

Zlokovic, B. V. (2002). Vascular disorder in Alzheimer's disease: role in pathogenesis of dementia and therapeutic targets. Adv Drug Deliv Rev 54, 1553-1559.

```
                                                       D313
1 Human GGA3    KLASETEDNDNSLGDILQASDNLSRVINSYKTIIEGQVINGEVATLTLPDSEGNSQCSNQGTILDLAELDTTNSLSSVLAPTPPSSGIPILPPPQASGPPRSRSSQAEATLGPSST  383
2 Mus musculus  KLASETEDNDNSLGDILQASDNLSRVINSYKTIIEGQIVNGEVTTSTMPDSEGNSHCGNQGALIDLAELDAPSNSS-----PALAPPTSGIPILPPPQTSGPPRSRSSQAEAPPGSDST  379
4 Bos taurus    KLASETEDNDNSLGDILQASDNLSRVINSYKTVVEGQVINGEVATSAMPDSEGN-HSRNQGTLIDLAELDTPGSSSS---VLAPAPPSSGIPILPPPQTSGPRSHSSQAEVTPTPNST  380
3 Canis fam     KLASETEDNDSSLGDILQASDNLSRVINSYKTVVEGQVNGEVTSAIPDSEGN------QGTLIDLAELDLAEVAPSGPPP--ALAPAPAGGSIPVLPPPQASGPRSHSAGQPEAPPGPSST  473
                *****:******:*******************.**:***:*****:**:****,   * :*:****:***:*.:***  :*: ** *::******.**:**  ***.* :*  .**

1 Human GGA3    SNAISWIDEELLCLGLADPAPNVPPKESAGNSQWHLLQREQ-SDLDFFSRPGTAACGASDAPLLQPSAPSSSSQAPLPPPPFPAPVVPASVPADSAGSSLFSTGVAPALAPKVEPAVPG  502
2 Mus musculus  NNAISLLDEELLCICLGLTDPAPTAP-KESPGGSQWHLFQNEPPSDLDFFSRPVPAASCPSDGPQLPPPVSTSSMSQAPLPAAFPAPVVPASAPTHSTGSFMFSSGPPAPALAPKAEPKGPE  498
4 Bos taurus    SNALCLLDEELLCICLGLADPAPTAPSDAPTAPGKDSAGNSQWNPFONEQ-SDLEFCGPKPGSAACSPSDGLLIVPPSASSAGSSOAPLPSFSAPVVPATGPRAPKAGSFLPSGLAPASAPKAESTALG  499
3 Canis fam     SNALSLLDEELLCICLGLIDPAPSAPPAKAAGNSQMPLLONER-SDLDFFSPKPGPGACSPTDGPLLQPSVAPIGSSQ---------APVAPAGVPRATASPLFSTGLASALAPKAEPIAPG  584
                .**: :*****: ** :**.*.         :**   :   ***:*   . * *                         .                        :  :*****.* .

V599
1 Human GGA3    HHGLAIGNSALHHIDALDQLLEEAKVTSGLVK----------PTTSPLIPTTPARDILPFSTCPGSPLFQPLSFPSQGSPPKGPELSLASIHVPLESIKPSSALPVTAYDKNGFRILFHF  613
2 Mus musculus  YP---SSSTSHRIDALDQLLEEAKVTSGLVKPVS-CFSPGPTASPLLPASAPARPLLPFSTCPGSPLFQ-----SQGSPQXGPELSLASVHVPLESIKPSSALPVTAYDKNGFRILFHF  608
4 Bos taurus    YHGSALGDSTHQIDALDHLLEDRATSGLVKPVSSIFFPGAMTSPLIPTSTTARDLLPFSPGPGSPLFQPPPAFQSQGSPMKGPELSLASVHVPLESIKPSSALPVTAYDKNGFRILFHF  619
3 Canis fam     HRGSTLGDSTPHQLDALDQLLEEAKATSGLVPATSSCFLGAAAPPLLPSGASASRPLLPLSAGPSGPLSQ-----AQGSPMKGPELSLASVHVPLESIKPSSALPVTAYDKNGFRILFHF  699
                 :    .:: ::.***:.** .* :*.**                * *** .  **:**: **:** *      ::*** .***.****:**************************

1 Human GGA3    AKECPGRPDVLVVVSMLNTAPLPVKSIVLQAAVPRSMKVKLQPPSGCTELSPFSPIQPPAAITQVMLLANPLKEKVRLYKLITFALGEQLSTEVGEVDQFPPVEQNGNL  723
2 Mus musculus  AKECPGRPDVLVVVSMLNTAPLPVKSIVLQAAVPRSMKVKLQPPSGCTELSPFSPIQPPAAITQVMLLANPMKEKVRLYKLITFALGEQLSTELGEVDQFPPVEQNGNL  718
4 Bos taurus    AKECPGRPDVLVVVSMLNTAPLPIKSIVLQAAVPRSMKVKLQPPSGCTELSPFSPIQPPAAITQVMLLANPLKEKARLYRLITFALGEQLSTEVGEVDQFPPVEQNGNL  729
3 Canis fam     AKECPGRPDVLVVVSMLNTAPLPIKSIVLQAAVPRSMKVKLQPPSGCTELSPFSVQPPAAITQVMLLANPLKEKARLYRLITFALGEQLSTEVGEVDEFPPVEQNGNL  809
                ***********************:*****************************.*********************.*** *******************:*********
```

Fig. 6G

```
                                                      D328
                                              D313    D333
1 Human GGA3    KLASETEDNDNSLGDILQASDNLSRVINSYKTIIEGQVINGEVATLLPDSEGNSQCSNQGTLIDIAELLTNSLSSVLAPATPPSSGIPILPPPQASGPPRSRSSQAEALLGPSST 383
2 Mus musculus  KLASETEDNDNSLGDILQASDNLSRVINSYKTIIEGQVINGEVTTSTMPDBEGNSHCNQGALIDIAELDAPSNSS----PALAPPTSGIPILPPPQTSGPPRSRSSQAEAPPGSDST 379
4 Bos taurus    KLASETEDNDSSLGDILQASDNLSRVINSYKIVVEGQVINGEVATSAMPDSEGN-HSRNQGTLIDIAELTPGSSSS--VLAPAPPSSGIPILPPPQTSGPGRSHSSQAEVTPTNST 380
3 Canis fam     KLASETEDNDSSLGDILQASDNLSRVINSYKTVVEGQVVNGEVVSAIPDSEGN--QGTLIDIAEVAPSGPPP--ALAPAPAGSGIPVLPPPQASGPGRSHSAGQPEAPPGPSST 473
                ********.*****:********:*:**:;*******.*.  *.* :;*****.   ****:******  ..    *.  *.. .,*.

D428
1 Human GGA3    SNALSWLDEELLCLGLADPAPNVPPKESAGNSQWHLLQEEQ-SDLDFFSPRPGTAACCASDAPLLQPSAPSSSSQAPLPPPPPAPVVPASVPADSAGSSLFRSTGVAPALAPKVEPAVPG 502
2 Mus musculus  NNALSLLDEELLCLGLTDPAPTAP-KESPGSSQWHLFQNEPPSDLDFFSPRPVPAASCPSDGPQLLPPPPVSTSSMSQAPLPAAFPAPVPASAPHSTGSFMFSSGPAPAPALAPRAEPKGPE 498
4 Bos taurus    SNALCLLDEELLCLGLTCLGLADPAPTAPSKDSAGNSQWPLFQNEQ-SDLEFCGPKRGSAACSPSDGLIVPPSASSAGSSQAPLPSPFSAPVVPATGPAPKAGSFLPSGLAPASAPKAESTALG 499
3 Canis fam     SNALSLLDEELLCLGLTDPAPSAPPAKAAGNSQWPLLQNER-SDLDFFSPKPGPGACSPTDGPLLQPSVAPIGSQ----------APVAPAGVPAPTASPFLFSTGLASALAPRAEPIAPG 584
                .***. *******.*:**.**:. ...;.:.***.**  .: .**.*: *.**.   . .. : :: ::*.   *.    .      .. ..  *..**.  * ..

V599
1 Human GGA3    HHGLALGNSALHHLDALDQLLEEAKVTSGLVK------------PTTSPLIPTTPARPLLPFSTGGSPLFQPLSFQQGSPPKGPELSLASIHVPLESIKPSSALPVTAYDKNGFRILFHF 613
2 Mus musculus  YP------SSSTSHRLDALDQLLEEAKVTSGLVRPVS-CFSPGPTASPLLPASAPARPLLPFSTGPGSPLFQ-----SQGSPQKCPELSLASVHVPLESIKPSSALPVTAYDKNGFRILFHF 608
4 Bos taurus    YHGSALGDSTLHQLDALDHLLEDTRATSGLVRPVSSIFFPGATTSPLIPTSTARPLLPFSTGSPGPGSPLFQPPAFQSQGSPMKGPELSLASVHVPLESIKPSSALPVTAYDKNGFRILFHF 619
3 Canis fam     HRGSTLGDSTPHQLDALDQLLEEAKATSGLVKPATSSCCELGAAAPPLLPSAGPSASARPLLPLSAGPSSPLFQ----AQGSPMKGPELSLASVHVPLESIKPSSALPVTAYDKNGFRILFHF 699
                  .    .: .  . ..**.***.::   *****.                 *:*:;*: ..**.**:   *,*:  .;*** *****:*:.:****************************

1 Human GGA3    AKECPPGGRPDVLVVVVSMLNTAPLPVKSIVLQAAVPKSMKVKLQPPSGTELSPFFSPIQPPAAITQVMLLANPLKEAVPLRVIKLTFALGEQLSTEVGEVDQPPPVEQWGNL 723
2 Mus musculus  AKECPPGGRPDVLVVVVSMLNTAPLPVKSIVLQAAVPKSMKVKLQPPSGTELSPFFSPIQPPAAITQVMLLANPLIANPMKEVPRLRYKILTFALGEQLSTELGEVDQPPPVEQWGNL 718
4 Bos taurus    AKECPPGGRPDVLVVVVSMLNTAPLPIKSIVLQAAVPKSMKVKLQPPSGTELSPFFSPIQPPAAITQVMLLANPLKEKARLRYKILTFALRVRLTFALGEQLSTELGEVDEFPPVEQWGNL 729
3 Canis fam     AKECPPGGRPDVLVVVVSMLNTAPLPIKSIVLQAAVPKSMKVKLQPPSGTELSPFFSPVQPPAAITQVMLLANPLKEKARLRYKILTFALGEQLSTEVGEVDQFPPVEQWGNL 809
                ****.************************.*****************************:***********.**:*.*:*:***:**********:*****::*******
```

Fig. 13A

SEQUENCE LISTING

```
<160> NUMBER OF SEQ ID NOS: 7

<210> SEQ ID NO 1
<211> LENGTH: 4
<212> TYPE: PRT
<213> ORGANISM: Homo sapiens
<220> FEATURE:
<221> NAME/KEY: misc_feature
<222> LOCATION: (2)..(2)
<223> OTHER INFORMATION: Xaa can be Ser or Thr
<220> FEATURE:
<221> NAME/KEY: misc_feature
<222> LOCATION: (4)..(4)
<223> OTHER INFORMATION: Xaa can be Ser or Thr

<400> SEQUENCE: 1
```

Asp Xaa Gly Xaa
1

<210> SEQ ID NO 2
<211> LENGTH: 5
<212> TYPE: PRT
<213> ORGANISM: Homo sapiens
<220> FEATURE:
<221> NAME/KEY: misc_feature
<222> LOCATION: (2)..(3)
<223> OTHER INFORMATION: Xaa can be any naturally occurring amino acid

<400> SEQUENCE: 2

Asp Xaa Xaa Leu Leu
1               5

<210> SEQ ID NO 3
<211> LENGTH: 4
<212> TYPE: PRT
<213> ORGANISM: Homo sapiens

<400> SEQUENCE: 3

Thr Leu Pro Asp
1

<210> SEQ ID NO 4
<211> LENGTH: 20
<212> TYPE: DNA
<213> ORGANISM: Homo sapiens

<400> SEQUENCE: 4
atgggtgagg ttaccaacca                                               20

<210> SEQ ID NO 5
<211> LENGTH: 20
<212> TYPE: DNA
<213> ORGANISM: Homo sapiens

<400> SEQUENCE: 5
gacaacgtag aagccctcca                                               20

<210> SEQ ID NO 6
<211> LENGTH: 20
<212> TYPE: DNA
<213> ORGANISM: Homo sapiens

<400> SEQUENCE: 6
ggtctcctct gacttcaaca                                               20

<210> SEQ ID NO 7
<211> LENGTH: 20
<212> TYPE: DNA
<213> ORGANISM: Homo sapiens

<400> SEQUENCE: 7
gtgagggtct ctctcttcct                                               20

REGULATION OF BACE DEGRADATION

RELATED APPLICATIONS

This application is a continuation of U.S. application Ser. No. 11/827,445, filed Jul. 11, 2007, now pending, and claims the benefit under 35 U.S.C. 119(e) of U.S. provisional application Ser. No. 60/819,832, filed Jul. 11, 2006, the disclosures of which are incorporated herein by reference.

GOVERNMENT INTEREST

This work was funded in part by the National Institutes of Health under grant numbers 1K12 MH069281-01 and 1R01AG025952-01A2, and by the National Institute of Mental Health under grant number 1R37MH60009. The government has certain rights in this invention.

FIELD OF THE INVENTION

The invention relates to methods and products for diagnosing, preventing, and treating Alzheimer's disease and abnormal production of amyloid $\beta$.

BACKGROUND OF THE INVENTION

Alzheimer's disease (AD) is a disorder that causes the gradual loss of brain cells. AD is named after Dr. Alois Alzheimer, who in 1906 noticed changes in the brain tissue of a woman who had died of an unusual mental illness. Upon examination, Dr. Alzheimer found abnormal clumps and tangled bundles of fibers, which are now known as amyloid plaques and neurofibrillary tangles, respectively. Today, these plaques and tangles in the brain are considered hallmarks of AD.

AD results in damage in brain regions associated with thought, memory, and language. Symptoms of AD are progressive and include dementia, which includes characteristics such as loss of memory, problems with reasoning or judgment, disorientation, difficulty in learning, loss of language skills, and decline in the ability to perform routine tasks. Additional AD symptoms may include personality changes, agitation, anxiety, delusions, and hallucinations.

The risk of AD in the population increases with age. It is believed that up to 4 million Americans have AD. The onset of AD is generally after age 60, but in rare instances younger individuals may be afflicted. It is generally believed that approximately 3 percent of men and women ages 65 to 74, and almost half of those age 85 and older have AD.

There is as yet no clear understanding of the cause of AD. Age is a known risk factor and there is some association between family history and early-onset AD. Although a pattern of decline in AD patients is generally clinically recognizable as the disease progresses, reliable diagnostic methods are lacking. The only definitive diagnostic test for AD at this time is to determine whether amyloid plaques and tangles are present in a subject's brain tissue, a determination that can only be done after death. Thus, due to the lack of suitable diagnostic methods, health-care professionals are only able to provide a tentative diagnosis of AD in an individual, particularly at the early to mid stages of the disease. Although these diagnoses can indicate that a person "likely" has AD, the absence of a definitive diagnosis reflects a critical need for more accurate and reliable AD diagnostic tests.

In addition to the absence of reliable diagnostic methods, the are also very limited treatment options available for patients suspected of having and/or diagnosed as having AD. Several drugs have been approved in the US for treatment of early and mid-stage AD, but they have significant detrimental side effects and limited efficacy. The lack of effective treatments for AD means that even with a diagnosis of probable AD, the therapeutic options are quite limited. Thus, there is a significant need for effective compounds and methods for preventing and/or treating AD.

SUMMARY OF THE INVENTION

We have elucidated the roles of GGA proteins that are involved in the degradation of BACE protein, the enhanced presence of which contributes to amyloid $\beta$ (A$\beta$)-accumulation-associated disorders, and have developed methods to diagnose A$\beta$-accumulation-associated disorders, e.g., Alzheimer's disease, based on the involvement of GGA proteins in these processes. The invention includes diagnostic methods and methods to identify compounds that modulate the stability of a GGA protein, or GGA protein complex, in a cell, tissue, or subject. The methods and compounds of the invention are also useful for preventing and/or treating A$\beta$-accumulation-associated disorders.

According to one aspect of the invention, methods for diagnosing a disorder associated with altered $\beta$-secretase processing of substrates are provided. The methods include measuring the stability and/or amount of a GGA protein in a biological sample from a subject, wherein decreased protein stability and/or amount relative to that in a control biological sample is an indication that the subject has a disorder associated with altered $\beta$-secretase processing of substrates.

According to another aspect of the invention, methods for determining onset, progression, or regression, of a disorder associated with altered $\beta$-secretase processing of substrates in a subject are provided. The methods include measuring the stability and/or amount of a GGA protein in a first biological sample of a subject, measuring the stability and/or amount of the GGA protein in a second biological sample of a subject obtained at a second time, and comparing the measurement of stability and/or amount in the first sample to the measurement of stability and/or amount in the second sample as a determination of the onset, progression, or regression of the disorder associated with altered $\beta$-secretase processing of substrates.

According to still another aspect of the invention, methods for identifying compounds that modulate caspase activation-induced cleavage of a GGA protein are provided. The methods include contacting cells that have been induced to undergo caspase activation with a candidate modulator of GGA protein cleavage, and measuring the stability of the GGA protein, wherein a difference in the cleavage of the protein relative to the cleavage of the protein in untreated cells is an indication that the candidate modulator is a compound that modulates the caspase activation-induced cleavage of the GGA protein. In certain embodiments, a decrease in the cleavage of the GGA protein relative to the cleavage of the GGA protein in untreated cells indicates the candidate modulator is an inhibitor of cleavage of the GGA protein. In other embodiments, an increase of the cleavage of the GGA protein relative to the stability of the GGA protein in untreated cells indicates the candidate modulator is an enhancer of cleavage of the GGA protein. In one embodiment, the cells are contacted with the candidate modulator before caspase activation induction. In another embodiment, the cells are contacted with the candidate modulator after caspase activation induction. In yet another embodiment, the caspase activation induces apoptosis.

In some embodiments of the foregoing methods, the disorder associated with altered $\beta$-secretase processing of substrates is an Aβ-accumulation-associated disorder, cancer, neurological diseases, immunologic diseases and glycoconjugate metabolism disorders, Alzheimer's disease, Down's syndrome, cerebrovascular amyloidosis, inclusion body myositis and hereditary inclusion body myopathies, diseases associated with abnormal BACE activity, ischemia, oxidative stress, head trauma, stroke, hypoglycemia, or any neurodegenerative disorder with increased caspase activation.

In other embodiments of the foregoing methods, the GGA protein is GGA1, GGA2 or GGA3.

In still other embodiments of the foregoing methods, the subject is human or is at risk of developing Alzheimer's disease.

In further embodiments of the foregoing methods, the biological sample is selected from the group consisting of cells and tissues. Preferably the cells are neuronal cells or the tissue includes neuronal cells.

According to another aspect of the invention, methods for treating or preventing a disorder associated with altered β-secretase processing of substrates are provided. The methods include administering to a subject in need of such treatment an effective amount of a compound that is an inhibitor of degradation of a GGA protein or GGA protein complex, or that increases GGA protein amounts in the subject.

In some embodiments of the foregoing methods, the disorder associated with altered β-secretase processing of substrates is an Aβ-accumulation-associated disorder, cancer, neurological diseases, immunologic diseases and glycoconjugate metabolism disorders, Alzheimer's disease, Down's syndrome, cerebrovascular amyloidosis, inclusion body myositis and hereditary inclusion body myopathies, diseases associated with abnormal BACE activity, ischemia, oxidative stress, head trauma, stroke, hypoglycemia, or any neurodegenerative disorder with increased caspase activation.

In other embodiments of the foregoing methods, the GGA protein is GGA1, GGA2 or GGA3.

In still other embodiments of the foregoing methods, the subject is human or is at risk of developing Alzheimer's disease.

In a further embodiment, the compound is linked to a targeting molecule; preferably the targeting molecule's target is a neuronal cell.

In other embodiments, the compound is selected from the group consisting of small molecules, polypeptides, and nucleic acids. Preferably the polypeptide is a GGA protein, an antibody or an antigen-binding fragment thereof. Preferably the nucleic acid molecule is selected from the group consisting of: molecules encoding a GGA protein, antisense molecules, RNAi molecules, and siRNA molecules.

In some embodiments, the mode of administration is selected from the group consisting of: implantation, mucosal administration, injection, inhalation, and oral administration.

In still other embodiments the compound is administered in combination with an additional drug or therapy for treating an Aβ-accumulation-associated disorder.

Methods for preparing a drug formulation are provided in another aspect of the invention. The methods include identifying a compound that inhibits degradation of a GGA protein or GGA protein complex by the foregoing method and formulating the compound for administration to a subject in need of such treatment.

In some embodiments the drug formulation is used in the treatment of an Aβ-accumulation-associated disorder, a disorder associated with altered β-secretase processing of substrates, cancer, neurological diseases, immunologic diseases and glycoconjugate metabolism disorders, disorders of cell adhesion, cardiovascular diseases, Alzheimer's disease, Down's syndrome, cerebrovascular amyloidosis, inclusion body myositis and hereditary inclusion body myopathies, diseases associated with abnormal BACE activity, ischemia, oxidative stress, head trauma, stroke, hypoglycemia, or any neurodegenerative disorder with increased caspase activation.

Use of the compositions described herein in the preparation of a medicament also is provided. Preferred medicaments include those which are useful in modulation of Aβ accumulation in a subject, particularly for treatment of Aβ accumulation-associated disorders such as Alzheimer's disease, Down's syndrome, cerebrovascular amyloidosis, inclusion body myositis and hereditary inclusion body myopathies, diseases associated with abnormal BACE activity, ischemia, oxidative stress, head trauma, stroke, hypoglycemia, and any neurodegenerative disorder with increased caspase activation.

These and other aspects of the invention are described in further detail below in connection with the detailed description of the invention.

BRIEF DESCRIPTION OF THE DRAWINGS

FIG. 4 shows that BACE protein levels increase following cerebral ischemia in rats and in mice. Cerebral ischemia was induced by middle cerebral artery occlusion for 1 hr in female rats (FIG. 4a,c) or in mice (FIG. 4b). After desired times of reperfusion the animals were sacrificed. The brains were dissected in the ischemic (ipsilateral, I) and not-ischemic (contralateral, C) hemispheres and each hemisphere in cortex (Ctx) and sub-cortex (Sub-Ctx). In the case of the mice only subcortex was examined. The tissues were homogenized in RIPA buffer.

FIG. 5 shows that GGA3 undergoes caspase-mediated cleavage during apoptosis.

FIG. 6 demonstrates that Caspase 3 cleaves GGA3 at three major sites including D313. FIG. 6b: recombinant caspase 3 cleaves in vitro translated GGA3 (cold methionine) in three fragments detected in WB by anti-GGA3 Ab. FIG. 6g: Multiple sequence alignment of human (NP_619525), *mus musculus* (NP_766636), *Bos taurus* (XP_587687) and *canis familiaris* (XP_540429) GGA3. Putative caspase consensus sequence in the hinge and GAE domain are in box. The black line indicates the epitope recognized by the anti GGA3 antibody. The Hinge domain starts at D313 and end at V599.

FIG. 7 shows the effect of GGA3 overexpression on BACE protein levels.

FIGS. 9a,c: GGA3 protein levels are significantly decreased in the same AD brains.

Figure 1:
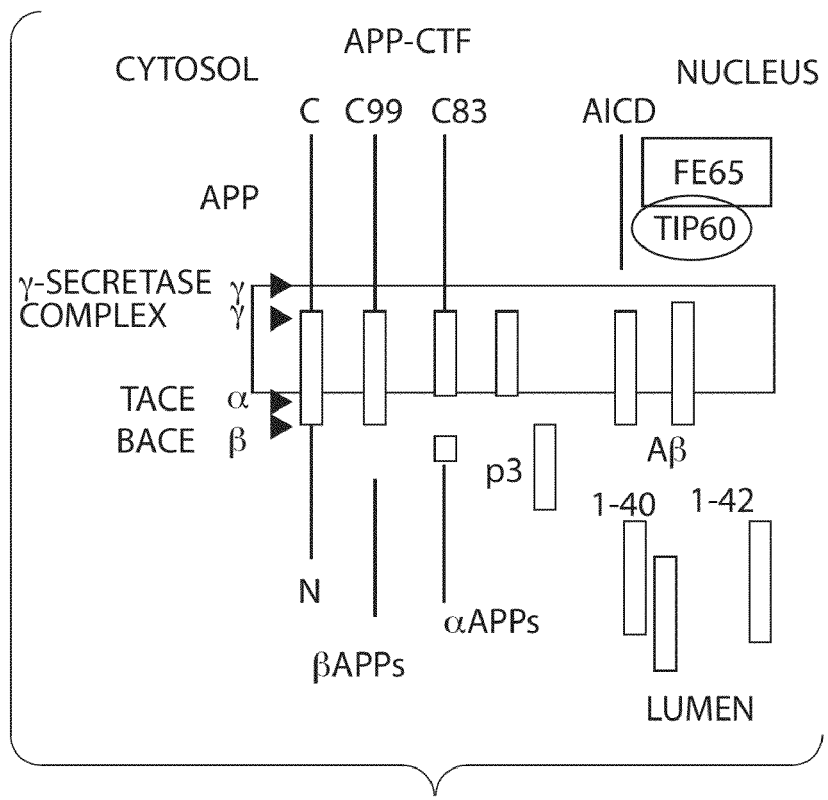
FIG. 1 is a schematic representation of amyloid precursor processing.

A: HA-tagged GGA3DN, HA-tagged GGA3 w.t. or vector alone with myc-tagged BACE in H4-APP751 cells. WB analysis performed with anti-HA antibody (Cell Signaling) revealed the expression of GGA3 construct. WB analysis performed with anti-myc (Cell Signaling) revealed that BACE levels were increased in the cells expressing GGA3DN compared to cells expressing vector alone or GGA3. B: The graph represents mean±SEM of at least 6 BACE levels measurements. Densitometry was performed using Versadoc Imager and QuantityOne software (Bio-Rad). BACE densitometry values were normalized against GAPDH values. Unpaired T-test with Welch correction was used for statistical analysis. p=0.0014 vector vs GGA3DN. p=0.0008 GGA3 w.t vs GGA#DN. C: The graph represents mean±SEM of at least 6 Aβ0 measurements by ELISA. Aβ concentration was normalized against the concentration of protein in cell lysates.

FIG. 15: RNAi Silencing of GGA3 Increases Levels of BACE, APP-C99, and Ab.

A: H4-APP751 cells were transfected with 200 nM siRNA GGA3 or 200 nM siNeg control. After 72 hr, GGA3 protein levels were determined by WB with anti-GGA3 antibody (Transduction Laboratories). GAPDH was used as loading control. B: After 72 hr, a sister plate of the same cells was co-transfected with myc-tagged BACE and siGGA3 or siNeg control. EGFR levels detected by WB with anti-EGFR antibody (Cell Signaling) were increased in the siGGA3 treated cells. BACE protein levels were detected by WB using anti-myc polyclonal antibody (Cell signaling) were also increased in the siGGA3 treated cells. Levels of GAPDH were unchanged. C-D: the graph represents mean±SEM of 6 or 7 BACE levels measurements for H4-APP751 and H4 APPSwe, respectively. Densitometry was performed using Versadoc Imager and QuantityOne software (Bio-Rad). BACE densitometry values were normalized against GAPDH values. Unpaired T-test with Welch correction was used for statistical analysis. E: Full-length APP and APP-C99 levels were detected by WB with WO2 antibody in H4-APPSWE cells. F-G: the graph represents mean±SEM of 6 or 9 Aβ0 measurements by ELISA in H4-APP751 or H4 APPSWE, respectively. Aβ concentration was normalized against the concentration of protein in cell lysates. Unpaired T-test with Welch correction was used for statistical analysis.

FIG. 16: GGA3 Is Degraded during Cerebral Ischemia Concurrently with Caspase Activation and Increased BACE Levels.

A: Cerebral ischemia was induced by middle cerebral artery occlusion for 1 hr in female rats. After desired times of reperfusion, the animals were sacrificed. The brains were dissected in the ischemic (ipsilateral, I) and not-ischemic (contralateral, C) hemispheres and each hemisphere in cortex (Ctx) and sub-cortex (Sub-Ctx). A-B: WB analysis with anti-BACE antibody (ABR) revealed an increase in BACE proteins levels in the ischemic hemisphere (samples were run in duplicate) after 48 hr of reperfusion. β-tubulin was used as loading control. The densitometry analysis of BACE after normalization against β-tubulin levels is represented in the graph. Mean±SEM of 5 rats. Statistical analysis was performed using Mann-Whitney test. WB with an anti-APP-CTF antibody (A8717, Sigma) revealed an APP caspase-derived fragment in the rat ischemic hemisphere (samples were run in duplicate) after 48 hr of reperfusion. C: WB analysis with anti-GGA3 antibody revealed a decrease in GGA3 full-length and a longer exposure two fragments of GGA3 generated during ischemia after 12 and 48 hrs of reperfusion (C=contralateral hemisphere; I=ipsilateral hemisphere; SubCtx=subcortex; Ctx=cortex).

FIG. 17: Levels of GGA3 Are Decreased and Are Inversely Correlated with Increased Levels of BACE in AD Brains.

A. Western Blot analysis of temporal cortex of human brains. AD=Alzheimer's disease. ND=non-demented control. BACE was detected by SECB1. GGA3 was detected by anti-GGA3 antibody. GAPDH was used as loading control. B-C. BACE and GGA3 densitometry values were normalized against GAPDH values. At least triplicate of each samples were analyzed. The graphs represent mean±SEM of 19 ND and 20 AD. Unpaired t-test and unpaired t-test with Welch correction ware used to perform statistical analysis of BACE and GGA3 levels, respectively. D-E. Linear correlation analysis between BACE and GGA3 levels in AD and ND, respectively. The dotted line indicates the 95% confidence interval. F. GGA3 mRNA was quantified by real time PCR. The graph represents mean±SEM of 10 ND and 10 AD. SQ=starting quantity. Please note that the levels of GGA3 protein were significantly decreased in the same samples. G. Western Blot analysis of temporal cortex of human brains. AD=Alzheimer's disease. ND=non-demented control. Full-length caspase 3 was detected with anti-caspase 3 antibody. To show that full-length caspase 3 decrease during apoptosis, lysates from control (C), treated with (STS), and treated with STS+zVAD H4 cells were also included. GAPDH was used as loading control.

Figure 18A:
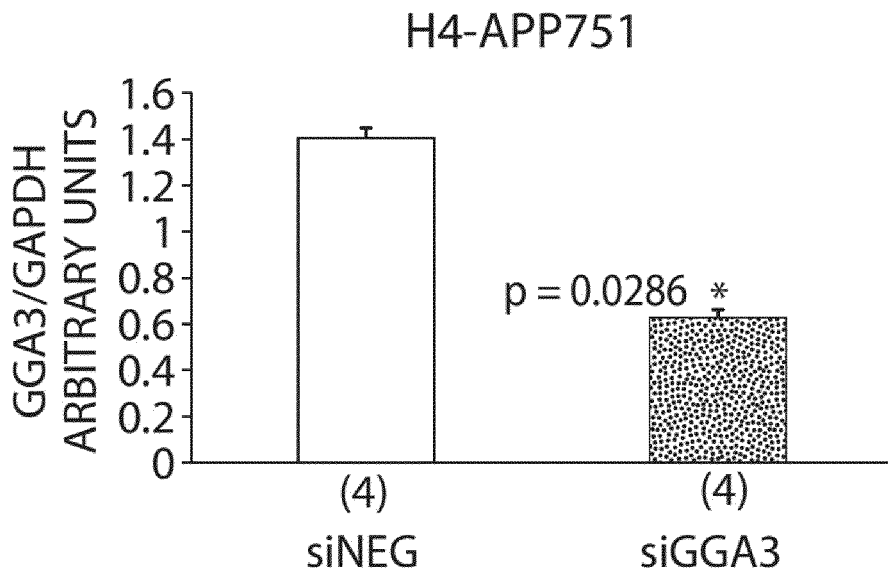

FIG. 18: Depletion of GGA3 by siRNA increases EGFR levels.

A-B. the graph represents mean±SEM of 4 measurements of GGA3 or EGFR protein levels, respectively, in H4-APP751 cells treated with siGGA3 or siNeg. Levels of EGFR were measured 72 hr after BACE and siGGA3 or siNeg co-transfection. Densitometry was performed using Versadoc Imager and QuantityOne software (Bio-Rad). GGA3 or EGFR densitometry values were normalized against GAPDH values. Mann-Whitney test was used for statistical analysis.

FIG. 19: Depletion of GGA3 by lentiviral RNAi increases both ectopically expressed and endogenous BACE in N2A cells.

A. Murine N2A cells were infected with lentivirus expressing either shRNA negative control or shRNA for murine GGA3 gene. Three different murine shRNA lentivirus were tested. After 72 hr, myc-tagged BACE vector was transfected in N2A cells. After additional 72 hr, GGA3 protein levels were determined by WB with anti-GGA3 antibody (Transduction Laboratories). BACE protein levels were detected by WB using anti-myc polyclonal antibody (Cell signaling). GAPDH was used as loading control. B-C. the graphs represent mean±SEM of 4 GGA3 or BACE levels measurements, respectively. Densitometry was performed using Versadoc Imager and QuantityOne software (Bio-Rad). GGA3 and BACE densitometry values were normalized against GAPDH values. The levels of GGA3 were 40% and 20% in cells infected with 310 or 306 lentivirus, respectively, compared to levels in cells infected with negative control virus. The levels of BACE were 150% and 200% in cells infected with 310 or 306 lentivirus, respectively, compared to levels in cells infected with negative control virus. D. N2A cells were infected as described above. After 72 hr GGA3 protein levels were determined by WB with anti-GGA3 antibody (Transduction Laboratories). Endogenous BACE protein levels were detected by WB using anti-BACE polyclonal antibody (Affinity Bioreagents). GAPDH was used as loading control. E: the graph represents mean±SEM of 3 BACE levels measurements. Densitometry was performed using Versadoc Imager and QuantityOne software (Bio-Rad). GGA3 and BACE densitometry values were normalized against GAPDH values. The levels of endogenous BACE were 140% in cells infected with 306 lentivirus, compared to levels in cells infected with negative control virus.

Figure 20A:
Figure 20B:
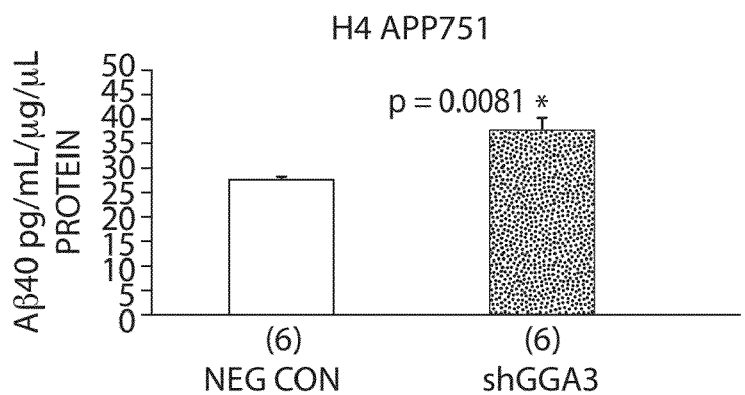
Figure 20C:
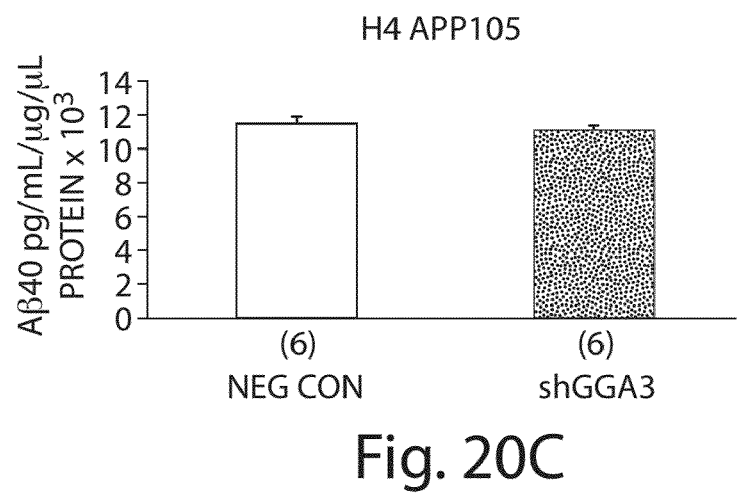

FIG. 20: Depletion of GGA3 affects APP processing independently of γ-secretase activity.
A. H4 cells expressing either APP-751 or the APP-CTF (APP105) were infected with lentivirus expressing either shRNA negative control or shRNA for human GGA3. After 72 hr, GGA3 protein levels were determined by WB with anti-GGA3 antibody (Transduction Laboratories). GAPDH was used as loading control. B-C. the graphs represent mean±SEM of 6 Aβ40 measurements by ELISA in H4-APP751 or H4-APP105 APPSWE, respectively. Aβ concentration was normalized against the concentration of protein in cell lysates. Unpaired T-test with Welch correction was used for statistical analysis.

FIG. 21: Levels of GGA3 are decreased in AD cerebellum. A. Western Blot analysis of cerebellum of human brains. AD=Alzheimer's disease. ND=non-demented control. BACE was detected by SECB1. GGA3 was detected by anti-GGA3 antibody. GAPDH was used as loading control. B-C. BACE and GGA3 densitometry values were normalized against GAPDH values. At least triplicate of each samples were analyzed. The graphs represent mean±SEM of 18 ND and 18 AD. Unpaired t-test and unpaired t-test with Welch correction ware used to perform statistical analysis of BACE and GGA3 levels, respectively. D-E. Linear correlation analysis between GGA3 levels in temporal cortex (TC) and cerebellum in ND and AD, respectively. The dotted line indicates the 95% confidence interval. F. the graph represents the distribution of AD versus ND relative to levels of GGA3 both in TC and cerebellum.

DETAILED DESCRIPTION OF THE INVENTION

The key neuropathological event in Alzheimer's disease (AD) is the accumulation in the brain of an ~4 kDa peptide called Aβ, the principle component of senile plaques. The Aβ peptide is derived by proteolysis of APP by β-secretase at the N-terminus followed by γ-secretase at the C-terminus. APP more commonly undergoes a non-amyloidogenic processing by α-secretases that cleaves in the middle of the β-amyloid domain (De Strooper and Annaert, 2000). β-secretase has been identified as a novel membrane-tethered member of the aspartyl proteases, termed BACE (beta-site APP-cleaving enzyme) (Sinha et al., 1999; Vassar et al., 1999), while candidate α-secretases include ADAM 9, 10 and 17 (TACE, tumor necrosis factor-α converting enzyme) (Buxbaum et al., 1998; Lammich et al., 1999). APP proteolysis by β- and α-secretases results in the production of secreted APP polypeptides (APPs) along with membrane-associated C99 and C83 APP-C-terminal fragments (APP-CTFs), respectively. The C99 and C83 APP-CTFs can then serve as substrates for γ-secretase resulting in the production of Aβ or p3, respectively (FIG. 1). Recent findings have shown that γ-secretase activity requires a set of four proteins including presenilins, nicastrin/Aph2, Aph1a and Pen-2 (Haass, 2004).

Figure 2:
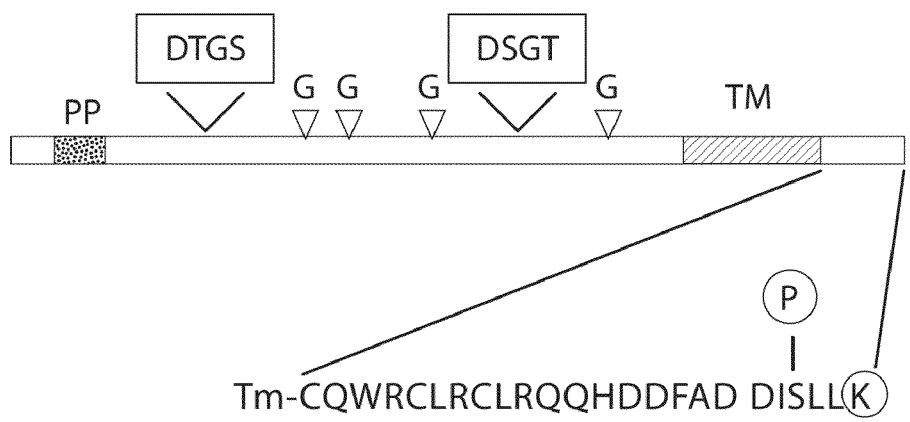
FIG. 2 is a schematic representation of BACE protein. G are the potential N-glycosylation sites. PP is the propeptide domain. Aspartyl protease signature sequences are boxed. Tm indicates that transmembrane domain. The C-terminus is enlarged to show the di-leucine motif and the phosphorylation site.

BACE is an N-glycosylated type 1 transmembrane protein that undergoes constitutive N-terminal processing in the Golgi apparatus. The terms "BACE" and "β-secretase" are used interchangably herein, unless the context requires otherwise. The ectodomain contains four glycosylation sites and two signature sequences typically associated with aspartyl proteases (DT/SGT/S; SEQ ID NO:1)(Citron, 2004). The BACE N-terminus contains a 24-amino acid propeptide which is removed by furin proteolysis (Benjannet et al., 2001). Furthermore, BACE has been shown to undergo shedding of its ectodomain probably by ADAM 10 (Hussain et al., 2003). BACE is targeted through the secretory pathway to the plasma membrane where it can be internalized to endosomes. The BACE-CTF contains a specific di-leucine (DXXLL; SEQ ID NO:2) sorting signal that is present in several transmembrane proteins (e.g. cation-dependent and cation-independent mannose-6-phosphate receptor, CD- and CI-MRP) and that regulates endocytosis and ultimately lysosomal degradation (Bonifacino and Traub, 2003; He et al., 2002; Huse et al., 2000) (FIG. 2). Mutagenesis of LL to AA results in retention of BACE at the plasma membrane (Huse et al., 2000; Pastorino et al., 2002). Furthermore, the di-leucine motif may play a role in BACE degradation since BACE LL/AA mutations increase protein levels of BACE (Pastorino et al., 2002).

Figure 3:
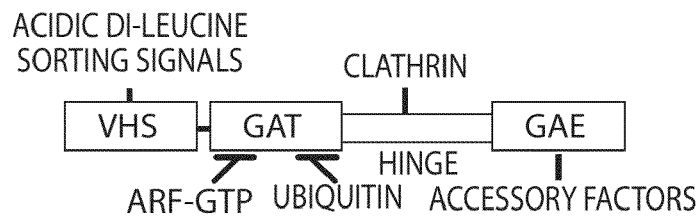
FIG. 3 shows a schematic representation of the domains and interactions of a typical GGA protein.

As used herein, the term "GGA protein" means a GGA1, GGA2, or GGA3 protein (Golgi-localized γ-ear-containing ARF binding proteins). GGA1, GGA2, and GGA3 have been shown to bind the BACE acidic di-leucine motif, and phosphorylation of BACE 5498 appears to increase their binding (He et al., 2002; He et al., 2003). GGA1, 2, and 3 are monomeric adaptors that are recruited to the trans-Golgi network by the Arf1-GTPase. They consist of four distinct segments: a VHS domain that binds the acidic di-leucine sorting signal, DXXLL (SEQ ID NO:2); a GAT domain which binds Arf: GTP; a hinge region which recruits clathrin; and a GAE domain which exhibits sequence similarity to the ear region of 7-adaptin and recruits a number of accessory proteins (FIG. 3). GGAs are necessary for the sorting of acid hydrolases to the lysosomes. Newly synthesized acid hydrolases modified with mannose 6-phosphate groups bind to mannose 6-phosphate receptors (MPRs). MPRs bind to the VHS domain of GGAs via the DXXLL (SEQ ID NO:2) motif. Vesicles budding from the TGN contains the MPR/GGA complex (Puertollano et al., 2001a). A dominant-negative GGA1 VHS-GAT construct lacking the hinge and GAE domains caused accumulation of CD-MPR at the TGN and its depletion from the periphery (Puertollano et al., 2001a). Thus, GGAs are likely involved in the transport from the Golgi complex to the endosome of proteins containing the DXXLL (SEQ ID NO:2) signal. However, Puertollano et al. (Puertollano and Bonifacino, 2004) have recently reported that GGA3 GAT domain binds ubiquitin and that ubiquitinated GGA3 is necessary for the delivery of activated EGFR to the lysosomes. Downregulation of GGA3, but not GGA1 or GGA2, by RNAi resulted in the accumulation of EGFR in enlarged early endosomes but did not perturb the internalization of activated EGFRs from the cell surface. These studies indicate that GGAs are also involved in the delivery of both biosynthetic and endosomal cargoes to the lysosomes. Thus, it is possible that GGA3 plays a role in the sorting of BACE to the lysosomes thus impacting its degradation.

The invention includes methods and compositions for the diagnosis of AD. Thus, the invention relates in part to the determination and modulation of levels, stabilization, and/or activity of a GGA protein, or GGA protein complex. As used herein, the term "complex" means an association comprising one or more GGA proteins and one or more other proteins, particularly BACE.

The invention includes the recognition that caspase cleaves GGA proteins. This recognition permits the modulation of Aβ accumulation for a variety of uses including therapeutic intervention in diseases (e.g., by reducing Aβ accumulation), creation of animal models of disease (e.g., by increasing Aβ accumulation), elucidation of the effects of Aβ accumulation, etc.

Increased Aβ accumulation is the result of increased Aβ production and/or reduced Aβ clearance. Therefore, Aβ accumulation can be modulated (to increase or decrease accumulation depending on the desired result) by modulating Aβ production and/or Aβ clearance to obtain a desired effect. Although not wishing to be bound by any particular theory, it is believed that there are four events that influence Aβ accumulation: Aβ production (e.g., production APP and processing of APP to Aβ), the rate and amount of Aβ aggregation and/or fibril formation, clearance of Aβ aggregates and/or fibrils by cell-mediated events, and direct degradation of Aβ aggregates and/or fibrils by enzymes. Each of these events is a potential target for modulating Aβ accumulation.

In addition to mediating processing of APP, BACE cleaves other substrates. For a review of beta-secretase substrates see e.g., Gruninger-Leitch et al., *J. Biol. Chem.* 277(7):4687-4693, 2002.

These additional non-APP substrates of β-secretase may be involved in other disorders including, neurological diseases. Thus, the stabilization of GGA and GGA complex components also provides a target for diseases associated with altered beta-secretase processing of substrates other than APP.

Altered β-secretase processing of substrates therefore can result in a variety of disorders that can be diagnosed and/or treated in accordance with the invention. The term "disorder associated with altered β-secretase processing of substrates" as used herein includes Aβ-accumulation-associated disorders such as Alzheimer's disease as well as other disorders correlated with proteins that also are substrates of β-secretase (cancer, neurological diseases, immunologic diseases, glycoconjugate metabolism disorders, and cardiovascular diseases including atherosclerosis), as described herein.

The methods of the invention in some aspects involve the use of compounds that inhibit caspase activation-induced Aβ production. Caspase activation in some instances results in apoptosis, and therefore in certain embodiments the methods include the use of compounds that inhibit apoptosis-induced Aβ production to reduce Aβ accumulation. As used herein, the term "Aβ production" means the generation of Aβ in a cell, tissue, or subject. As used herein, the term "subject" means any mammal that may be in need of treatment with the Aβ production modulating compounds of the invention or may be in need of diagnostic methods of the invention. Subjects include but are not limited to: humans, non-human primates, cats, dogs, sheep, pigs, horses, cows, rodents such as mice, hamsters, and rats.

As used herein, the term "Aβ production-modulating compound" means a compound that modulates the stability of a GGA protein or GGA protein complex in a cell, tissue, or subject. Compositions of the invention include compounds that modulate caspase activation-induced Aβ production in cells, tissues, and subjects. The methods of the invention involve the administration of compounds that modulate caspase activation-induced Aβ accumulation in neuronal cells and/or tissues and therefore are useful to reduce or prevent Alzheimer's disease, any other diseases or disorders associated with abnormal accumulation of Aβ such as Down's syndrome, cerebrovascular amyloidosis, inclusion body myositis and hereditary inclusion body myopathies and any disease associated with abnormal BACE activity. As used herein, the term "Aβ-accumulation-associated disorder" means Alzheimer's disease, Down's syndrome, cerebrovascular amyloidosis, inclusion body myositis and hereditary inclusion body myopathies, and any disease associated with abnormal (increased) BACE activity.

The invention includes the recognition that caspase activation can increase Aβ accumulation in neuronal cells and/or tissues (with or without apoptosis) and therefore the invention also provides methods and compositions for diagnosing and treating caspase activation disorders. Therefore, as used herein, Aβ-accumulation-associated disorders include caspase activation disorders. "Caspase activation disorders" include ischemia, oxidative stress, head trauma, stroke, hypoglycemia, and any neurodegenerative disorder with increased caspase activation. A feature of the caspase activation disorders is increased accumulation of Aβ.

The invention involves a variety of assays based upon detecting the level and/or activity of a GGA protein and/or GGA protein complex, in subjects. The assays include (1) characterizing the impact of levels or activity of a GGA protein or GGA protein complex in a subject; (2) evaluating a treatment for regulating levels and/or activity of a GGA protein or GGA protein complex in a subject; (3) selecting a treatment for regulating levels and/or activity of a GGA protein or GGA protein complex in a subject; and (4) determining regression, progression or onset of a condition characterized by abnormal levels and/or activity of a GGA protein or GGA protein complex in a subject.

Thus, subjects can be characterized, treatment regimens can be monitored, treatments can be selected and diseases can be better understood using the assays of the present invention. For example, the invention provides in one aspect a method for measuring the level and/or activity of a GGA protein or GGA protein complex in a subject. As provided by the invention, the level and/or activity of a GGA protein or GGA protein complex thus correlates with the existence of an Aβ accumulation-associated disorder, e.g. Alzheimer's disease. For example, a level and/or activity that is significantly lower in a subject than a control level may indicated a subject has Alzheimer's disease, whereas a relatively normal level of a GGA protein or GGA protein complex indicates that the subject does not have an Aβ accumulation-associated disorder of the invention, e.g. Alzheimer's disease.

The assays described herein are carried out on samples obtained from subjects. As used herein, a subject is a human, non-human primate, cow, horse, pig, sheep, goat, dog, cat, or rodent. In all embodiments, human subjects are preferred. The samples used herein are any cell, body tissue, or body fluid sample obtained from a subject. In some embodiments, the cell or tissue sample includes neuronal cells and/or is a neuronal cell or tissue sample.

The biological sample can be located in vivo or in vitro. For example, the biological sample can be a tissue in vivo and the agent specific for a GGA protein or GGA protein complex can be used to detect the presence of such molecules in the tissue (e.g., for imaging portions of the tissue that include a GGA protein or GGA protein complex). Alternatively, the biological sample can be located in vitro (e.g., a biopsy such as a tissue biopsy or tissue extract). In a particularly preferred embodiment, the biological sample can be a cell-containing sample. Samples of tissue and/or cells for use in the various methods described herein can be obtained through standard methods. Samples can be surgical samples of any type of tissue or body fluid. Samples can be used directly or processed to facilitate analysis (e.g., paraffin embedding). Exemplary samples include a cell, a cell scraping, a cell extract, a blood sample, a cerebrospinal fluid sample, a tissue biopsy, including punch biopsy, a tumor biopsy, a bodily fluid, a tissue, or a tissue extract or other methods. Samples also can be cultured cells, tissues, or organs.

Particular subjects to which the present invention can be applied are subjects at risk for or known to have an Aβ-accumulation-associated disorder. Such disorders may include, but are not limited to: Alzheimer's disease and any other diseases associated with overproduction of Aβ or reduced clearance of Aβ such as Down's syndrome, cerebrovascular amyloidosis, inclusion body myositis and hereditary inclusion body myopathies, any disease associated with abnormal BACE activity, ischemia, oxidative stress, head trauma, stroke, hypoglycemia, and any neurodegenerative disorder with increased caspase activation.

The assays described herein (see Examples section) include measuring levels and/or activity of a GGA protein or GGA protein complex. Levels and/or activity of a GGA protein or GGA protein complex can be measured in a number of ways when carrying out the various methods of the invention. In one type of measurement, the level of a GGA protein or GGA protein complex is a measurement of absolute levels of a GGA protein or GGA protein complex. This could be expressed, for example, in terms of molecules per cubic millimeter of tissue. Another measurement of the level of a GGA protein or GGA protein complex is a measurement of the change in the level and/or activity of the GGA protein or GGA protein complex over time. This may be expressed in an absolute amount or may be expressed in terms of a percentage increase or decrease over time.

Importantly, levels of a GGA protein or GGA protein complex are advantageously compared to controls according to the invention. The control may be a predetermined value, which can take a variety of forms. It can be a single value, such as a median or mean. It can be established based upon comparative groups, such as in groups having normal amounts of a GGA protein or GGA protein complex and groups having abnormal amounts of a GGA protein or a GGA protein complex. Another example of comparative groups would be groups having a particular disease (e.g., Alzheimer's disease), condition or symptoms, and groups without the disease, condition or symptoms. Another comparative group would be a group with a family history of a condition and a group without such a family history. The predetermined value can be arranged, for example, where a tested population is divided equally (or unequally) into groups, such as a low-risk group, a medium-risk group and a high-risk group or into quadrants or quintiles, the lowest quadrant or quintile being individuals with the lowest risk or amounts of a GGA protein or GGA protein complex and the highest quadrant or quintile being individuals with the highest risk or amounts of a GGA protein or GGA protein complex.

The predetermined value of course, will depend upon the particular population selected. For example, an apparently healthy population will have a different 'normal' range than will a population that is known to have a condition related to Aβ accumulation. Accordingly, the predetermined value selected may take into account the category in which an individual falls. Appropriate ranges and categories can be selected with no more than routine experimentation by those of ordinary skill in the art. By abnormally low it is meant low relative to a selected control. Typically the control will be based on apparently healthy normal individuals in an appropriate age bracket.

It will also be understood that the controls according to the invention may be, in addition to predetermined values, samples of materials tested in parallel with the experimental materials. Examples include samples from control populations or control samples generated through manufacture to be tested in parallel with the experimental samples.

The various assays used to determine the levels and/or activity of a GGA protein or GGA protein complex include: assays, such as described in the Examples section herein, and assays such as using materials that specifically bind to a GGA protein or GGA protein complex (e.g., immunoassays); gel electrophoresis; mass spectrometry; and the like. Immunoassays may be used according to the invention including sandwich-type assays, competitive binding assays, one-step direct tests and two-step tests such as routinely practiced by those of ordinary skill in the art.

As mentioned above, it is also possible to characterize the existence of an Aβ accumulation-associated disorder by monitoring changes in the absolute or relative amounts or activity of a GGA protein or GGA protein complex over time. For example, it is expected that a decrease that amount or activity of a GGA protein, or GGA protein complex correlates with increasing amounts of BACE and therefore increasing severity of an Aβ accumulation-associated disorder. Accordingly one can monitor levels and/or activity of a GGA protein or GGA protein complex to determine if the status (e.g., severity or existence) of an Aβ accumulation-associated disorder of a subject is changing. Changes in relative or absolute levels and/or activity of a GGA protein or GGA protein complex of greater than 0.1% may indicate an abnormality. Preferably, the change in levels and/or activity of a GGA protein or GGA protein complex, which indicates an abnormality, is greater than 0.2%, greater than 0.5%, greater than 1.0%, 2.0%, 3.0%, 4.0%, 5.0%, 7.0%, 10%, 15%, 20%, 25%, 30%, 40%, 50%, or more. Other changes, (e.g. increases or reductions) in levels or amounts and/or activity of a GGA protein or GGA protein complex over time may indicate an onset, progression, regression, or remission of the Aβ accumulation-associated disorder in the subject. As described above, in some disorders an increase in the level and/or activity of a GGA protein or GGA protein complex may mean regression of the disorder. Such a regression may be associated with a clinical treatment of the disorder thus the methods of the invention can be used to determine the efficacy of a therapy for an Aβ-accumulation-associated disorder (e.g. Alzheimer's disease). In some disorders a decrease in level and/or activity of a GGA protein or GGA protein complex may mean progression or onset of the disorder.

The invention in another aspect provides a diagnostic method to determine the effectiveness of treatments for abnormal levels or activity of a GGA protein or GGA protein complex. The term "evaluation of treatment" as used herein, means the comparison of a subject's levels and/or activity of a GGA protein or GGA protein complex measured in samples collected from the subject at different sample times, preferably at least one day apart. The preferred time to obtain the second sample from the subject is at least one day after obtaining the first sample, which means the second sample is obtained at any time following the day of the first sample collection, preferably at least 12, 18, 24, 36, 48 or more hours after the time of first sample collection.

The comparison of levels and/or activity of a GGA protein or GGA protein complex in two or more samples, taken on different days, is a measure of level of the subject's diagnostic status for an Aβ accumulation-associated disorder and allows evaluation of the treatment to regulate levels and or activity of a GGA protein or GGA protein complex. The comparison of a subject's levels and/or activity of a GGA protein or GGA protein complex measured in samples obtained on different days provides a measure of the status of the Aβ accumulation-associated disorder to determine the effectiveness of any treatment to regulate levels and/or activity of a GGA protein or GGA protein complex in the subject.

As will be appreciated by those of ordinary skill in the art, the evaluation of the treatment also may be based upon an evaluation of the symptoms or clinical end-points of the associated disease. In some instances, the subjects to which the methods of the invention are applied are already diagnosed as having a particular condition or disease. In other instances, the measurement will represent the diagnosis of the condition or disease. In some instances, the subjects will already be undergoing drug therapy for an Aβ accumulation-associated disorder (e.g. Alzheimer's disease), while in other instances the subjects will be without present drug therapy for an Aβ accumulation-associated disorder.

Agents, e.g. antibodies and/or antigen-binding fragments thereof, that specifically bind to a GGA protein or GGA protein complex, are useful in additional diagnostic methods. As described herein, the antibodies of the present invention thus are prepared by any of a variety of methods, including administering protein, fragments of protein, cells expressing the protein or fragments thereof and the like to an animal to induce polyclonal antibodies. In addition, antibodies that specifically bind to GGA proteins are available commercially. The production of monoclonal antibodies is according to techniques well known in the art. As detailed herein, such antibodies or antigen-binding fragments thereof may be used, for example, to quantify GGA proteins or GGA protein complexes, to identify tissues expressing protein or to purify protein.

As detailed herein, the foregoing antibodies or antigen-binding fragments thereof and other binding molecules may be used for example to identify a GGA protein or GGA protein complex. Antibodies also may be coupled to specific diagnostic labeling agents for imaging of cells and tissues with abnormal levels and/or activity of a GGA protein or GGA protein complex; or to therapeutically useful agents according to standard coupling procedures. Diagnostic agents include, but are not limited to, barium sulfate, iocetamic acid, iopanoic acid, ipodate calcium, diatrizoate sodium, diatrizoate meglumine, metrizamide, tyropanoate sodium and radiodiagnostics including positron emitters such as fluorine-18 and carbon-11, gamma emitters such as iodine-123, technitium-99m, iodine-131 and indium-111, nuclides for nuclear magnetic resonance such as fluorine and gadolinium. Other diagnostic agents useful in the invention will be apparent to one of ordinary skill in the art.

Using methods described herein, agents (e.g., antibodies or antigen-binding fragments thereof) can be identified and prepared that bind specifically to a GGA protein or to GGA protein complexes. As used herein, "binding specifically to" means capable of distinguishing the identified material from other materials sufficient for the purpose to which the invention relates. Thus, "binding specifically to" a GGA protein means the ability to bind to and distinguish GGA1, GGA2 and GGA3 proteins from other proteins, and preferably among the GGA proteins. Binding specifically to a GGA protein complex that includes one or more GGA proteins means binding to and distinguishing the complex from individual GGA proteins, or distinguishing from other complexes of proteins.

The invention also provides agents (e.g. antibodies) for use in methods to stabilize or destabilize a GGA protein or GGA protein complex. In such methods, the antibodies recognize and bind specifically to a GGA protein or GGA protein complex. Methods to stabilize or destabilize a GGA protein or a GGA protein complex may be used to treat Aβ accumulation-associated disorders; for example, methods to stabilize the proteins or complexes thereof, may be used to prevent or treat Alzheimer's disease.

Agents that bind to a GGA protein and fragments thereof, or bind to a GGA protein complex, include polypeptide agents. Such polypeptides include polyclonal and monoclonal antibodies, prepared according to conventional methodology. Antibodies that bind a GGA protein, fragment thereof, or a GGA protein complex are useful for determining GGA proteins, fragments thereof, or GGA protein complexes. Such antibodies include, but are not limited to: antibodies that bind specifically to a GGA protein, antibodies that bind specifically to fragments of a GGA protein, and antibodies that bind specifically to GGA protein complexes. Certain antibodies useful in the methods of the invention already are known in the art and include for example, the antibodies provided in the Examples section herein.

Significantly, as is well-known in the art, only a small portion of an antibody molecule, the paratope, is involved in the binding of the antibody to its epitope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F9(ab')$_2$ fragment, retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Proceeding further, Fab fragments consist of a covalently bound antibody light chain and a portion of the antibody heavy chain denoted Fd. The Fd fragments are the major determinant of antibody specificity (a single Fd Fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (Frs), which maintain the tertiary structure of the paratope (see, in general, Clark, W. R. (1986) *The Experimental Foundations of Modern Immunology*, Wiley & Sons, Inc., New York; Roitt, I. (1991) *Essential Immunology*, 7th Ed., Blackwell Scientific Publications, Oxford). In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is now well-established in the art that the non-CDR regions of a mammalian antibody may be replaced with similar regions of conspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816, 567, 5,225,539, 5,585,089, 5,693,762 and 5,859,205.

Thus, for example, PCT International Publication Number WO 92/04381 teaches the production and use of humanized murine RSV antibodies in which at least a portion of the murine FR regions have been replaced by FR regions of human origin. Such antibodies, including fragments of intact antibodies with antigen-binding ability, are often referred to as "chimeric" antibodies.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab')$_2$, Fab, Fv and Fd fragments; chimeric antibodies in which the Fc and/or Fr and/or CDR1 and/or CDR2 and/or light chain CDR3 regions have been replaced by homologous human or non-human sequences; chimeric F(ab')$_2$ fragment antibodies in which the FR and/or CDR1 and/or CDR2 and/or light chain CDR3 regions have been replaced by homologous human or non-human sequences; chimeric Fab fragment antibodies in which the FR and/or CDR1 and/or CDR2 and/or light chain CDR3 regions have been replaced by homologous human or non-human sequences; and chimeric Fd fragment antibodies in which the FR and/or CDR1 and/or CDR2 regions have been replaced by homologous human or nonhuman sequences. The present invention also includes so-called single chain antibodies.

Thus, the invention involves polypeptides of numerous size and type that bind specifically to a GGA protein, fragment thereof, or GGA protein complex. These polypeptides may be derived also from sources other than antibody technology. For example, such polypeptide-binding agents can be provided by degenerate peptide libraries, which can be readily prepared in solution, in immobilized form or as phage display libraries. Combinatorial libraries also can be synthesized of peptides containing one or more amino acids. Libraries further can be synthesized of peptoids and non-peptide synthetic moieties.

A wide variety of assays to identify pharmacological agents that modulate the stability of a GGA protein and/or GGA protein complex can be used in accordance with the aspects of the invention, including, labeled in vitro protein-protein binding assays, electrophoretic mobility shift assays, immunoassays, cell-based assays such as two- or three-hybrid screens, expression assays, etc. The assay mixture comprises a candidate pharmacological agent. Typically, a plurality of assay mixtures are run in parallel with different agent concentrations to obtain a different response to the various concentrations. Typically, one of these concentrations serves as a negative control, i.e., at zero concentration of agent or at a concentration of agent below the limits of assay detection.

Candidate agents encompass numerous chemical classes, although typically they are organic compounds. In some embodiments, the candidate pharmacological agents are small organic compounds, i.e., those having a molecular weight of more than 50 yet less than about 2500, preferably less than about 1000 and, more preferably, less than about 500. Candidate agents comprise functional chemical groups necessary for structural interactions with proteins and/or nucleic acid molecules, and typically include at least an amine, carbonyl, hydroxyl or carboxyl group, preferably at least two of the functional chemical groups and more preferably at least three of the functional chemical groups. The candidate agents can comprise cyclic carbon or heterocyclic structure and/or aromatic or polyaromatic structures substituted with one or more of the above-identified functional groups. Candidate agents also can be biomolecules such as peptides, saccharides, fatty acids, sterols, isoprenoids, purines, pyrimidines, derivatives or structural analogs of the above, or combinations thereof and the like. Where the agent is a nucleic acid molecule, the agent typically is a DNA or RNA molecule, although modified nucleic acid molecules as defined herein are also contemplated.

It is contemplated that cell-based assays as described herein can be performed using cell samples and/or cultured cells. Cells include cells that transformed to express a GGA protein, or fragment or variant thereof, and cells treated using methods described herein to modulate (e.g. inhibit or enhance) the level and/or activity of a GGA protein or GGA protein complex.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random peptides, and the like. Alternatively, libraries of natural compounds in the form of bacterial, fungal, plant and animal extracts are available or readily produced. Additionally, natural and synthetically produced libraries and compounds can be readily be modified through conventional chemical, physical, and biochemical means. Further, known pharmacological agents may be subjected to directed or random chemical modifications such as acylation, alkylation, esterification, amidification, etc. to produce structural analogs of the agents.

A variety of other reagents also can be included in the mixture. These include reagents such as salts, buffers, neutral proteins (e.g., albumin), detergents, etc. which may be used to facilitate optimal protein-protein and/or protein-nucleic acid binding. Such a reagent may also reduce non-specific or background interactions of the reaction components. Other reagents that improve the efficiency of the assay such as protease inhibitors, nuclease inhibitors, antimicrobial agents, and the like may also be used.

An assay may be used to identify candidate agents that modulate 1) production of Aβ, and/or 2) stability and/or activity of a GGA protein or GGA protein complex. In general, the mixture of the foregoing assay materials is incubated under conditions whereby, but for the presence of the candidate pharmacological agent, Aβ production occurs. It will be understood that a candidate pharmacological agent that identified as a modulating agent may be identified as reducing or eliminating Aβ production. A reduction in Aβ production need not be the absence of Aβ production, but may be a lower level of Aβ production. The order of addition of components, incubation temperature, time of incubation, and other parameters of the assay may be readily determined. Such experimentation merely involves optimization of the assay parameters, not the fundamental composition of the assay. Incubation temperatures typically are between 4° C. and 40° C. Incubation times preferably are minimized to facilitate rapid, high throughput screening, and typically are between 0.1 and 10 hours.

After incubation, the stability of a GGA protein, GGA protein complex, and/or Aβ production is detected by any convenient method available to the user.

Aβ production may be modulated using methods and/or compounds that modulate the stabilization or activity of a GGA protein, or GGA protein complex. As used herein, the term "modulate" means to change, which in some embodiments means to "enhance" and in other embodiments, means to "inhibit". In some embodiments, stabilization or activity of a GGA protein or GGA protein complex is reduced or inhibited. It will be understood that reduction may mean reduction to zero or may mean reduction to a level below a normal level, a previous level, or a control level.

The Aβ production modulating molecules of the invention may include small molecules, polypeptides, (for example, competitive ligands and antibodies, or antigen-binding fragments thereof), and nucleic acids. For example, compositions of the invention may include nucleic acids that encode a molecule that increases the stability and/or activity of a GGA protein, fragments and/or complexes thereof, nucleic acids that bind to other nucleic acids, [e.g. for antisense, RNAi, or small interfering RNA (siRNA) methods], or may be polypeptides that reduce the stability and/or activity of a GGA protein or complex that includes a GGA protein. Such polypeptides include, but are not limited to antibodies or antigen-binding fragments thereof.

Various methods may be used to decrease Aβ accumulation. Aβ accumulation may be decreased using methods that increase the level, stabilization, and/or activity of GGA proteins, or a GGA protein complex. In these embodiments, the level of expression or functional activity of one or more GGA proteins may be increased using methods such as administration of nucleic acids that encode GGA molecules, or other methods that increase expression of the molecules. Methods to increase the stability or activity of a GGA protein, or GGA protein complex may also include the use of binding agents, e.g. antibodies, to stabilize the proteins or complexes of one or more of the proteins.

In some embodiments of the invention, the level, stability, and/or activity of a GGA protein, or GGA protein complex may be decreased, for example, to produce cell or animal models of Alzheimer's disease or other neurological disorder. For example, methods of the invention include 1) the administration of molecules that are antisense of the nucleic acids that encode a GGA protein, 2) RNAi and/or siRNA inhibition methods, and/or 3) administration of antibodies that block the functional activity of the proteins in the production of Aβ (e.g. block interaction of the GGA proteins). The methods of reducing activity of the proteins may also include administering polypeptides or nucleic acids that encode polypeptides that are variants of the GGA proteins and are not fully functional. Such dominant negative variants may compete with the functional endogenous versions in a cell, tissue, or subject, and thereby reduce the Aβ production activity of the endogenous GGA proteins or GGA protein complexes.

The Aβ production-modulating compounds of the invention, which include for example, antisense oligonucleotides, RNAi and/or siRNA oligonucleotides, antibodies, nucleic acids directing the expression of GGA protein, and/or polypeptides may be administered as part of a pharmaceutical composition.

One set of embodiments of the aforementioned Aβ production-modulating compositions and methods include the use of antisense molecules or nucleic acid molecules that reduce expression of genes via RNA interference (RNAi or siRNA). One example of the use of antisense, RNAi or siRNA in the methods of the invention, although not intended to be limiting is their use to decrease the level of expression of one or more GGA proteins. The antisense oligonucleotides, RNAi, or siRNA nucleic acid molecules used for this purpose may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art-recognized methods, which may be carried out manually or by an automated synthesizer. They also may be produced recombinantly by vectors.

In some embodiments of the invention, the antisense oligonucleotides also may include "modified" oligonucleotides. That is, the oligonucleotides may be modified in a number of ways, which do not prevent them from hybridizing to their target but which enhance their stability or targeting or which otherwise enhance their therapeutic effectiveness.

The term "modified oligonucleotide" as used herein describes an oligonucleotide in which (1) at least two of its nucleotides are covalently linked via a synthetic internucleoside linkage (i.e., a linkage other than a phosphodiester linkage between the 5' end of one nucleotide and the 3' end of another nucleotide) and/or (2) a chemical group not normally associated with nucleic acids has been covalently attached to the oligonucleotide. Preferred synthetic internucleoside linkages are phosphorothioates, alkylphosphonates, phosphorodithioates, phosphate esters, alkylphosphonothioates, phosphoramidates, carbamates, carbonates, phosphate triesters, acetamidates, carboxymethyl esters and peptides.

The term "modified oligonucleotide" also encompasses oligonucleotides with a covalently modified base and/or sugar. For example, modified oligonucleotides include oligonucleotides having backbone sugars that are covalently attached to low molecular weight organic groups other than a hydroxyl group at the 3' position and other than a phosphate group at the 5' position. Thus, modified oligonucleotides may include a 2'-O-alkylated ribose group. In addition, modified oligonucleotides may include sugars such as arabinose instead of ribose. The present invention, thus, contemplates pharmaceutical preparations containing modified antisense molecules that are complementary to and hybridizable with, under physiological conditions, nucleic acid molecules encoding proteins of the invention, together with pharmaceutically acceptable carriers.

The methods to modulate Aβ accumulation also include methods to increase expression of fragments or variants of a GGA protein that may have reduced function (e.g., dominant negative molecules). Additionally, the invention includes methods that include cells or models of Alzheimer's disease, thereby including methods that decrease the stability, activity, or function of a GGA protein.

Thus, it will be recognized that the invention embraces the use of sequences that encode a GGA protein or fragment or variant thereof, in expression vectors, as well their use to transfect host cells and cell lines, be these prokaryotic (e.g., *E. coli*), or eukaryotic (e.g., CHO cells, COS cells, yeast expression systems and recombinant baculovirus expression in insect cells). Especially useful are mammalian cells such as human, mouse, hamster, pig, goat, primate, etc. They may be of a wide variety of tissue types, including neurons, mast cells, fibroblasts, oocytes, monocytes, lymphocytes, and leukocytes, and they may be primary cells or cell lines. Specific examples include neurons, keratinocytes, peripheral blood leukocytes, bone marrow stem cells and embryonic stem cells. The expression vectors require that the pertinent sequence, i.e., those nucleic acids described supra, be operably linked to a promoter.

The invention also permits the construction of polypeptide gene "knock-outs" or "knock-ins" in cells and in animals, providing materials for studying certain aspects of disorders associated with a GGA protein. For example, a knock-out mouse may be constructed and examined for clinical parallels between the model and characteristics and symptoms found in subjects with Alzheimer's disease. Such a cellular or animal model may be useful for assessing treatment strategies for Aβ accumulation-associated disorders, e.g. Alzheimer's disease. This type of knock-out model provides a model with which to evaluate the effects of candidate pharmacological agents (e.g., inhibitory effects) on a living animal that has an abnormal level of Aβ production. In addition, animal or cell models may be constructed in which the level, stability, activity and/or function of a GGA protein is increased.

According to still a further aspect of the invention, a transgenic non-human animal comprising an expression vector of the invention is provided, including a transgenic non-human animal which has altered expression of molecule that modulates the level and/or the stability of a GGA protein.

As used herein, "transgenic non-human animals" includes non-human animals having one or more exogenous nucleic acid molecules incorporated in germ line cells and/or somatic cells. Thus the transgenic animal include "knock-out" animals having a homozygous or heterozygous gene disruption by homologous recombination, animals having episomal or chromosomally incorporated expression vectors, etc. Knock-out animals can be prepared by homologous recombination using embryonic stem cells as is well known in the art. The recombination can be facilitated by the cre/lox system or other recombinase systems known to one of ordinary skill in the art. In certain embodiments, the recombinase system itself is expressed conditionally, for example, in certain tissues or cell types, at certain embryonic or post-embryonic developmental stages, inducibly by the addition of a compound which increases or decreases expression, and the like. In general, the conditional expression vectors used in such systems use a variety of promoters which confer the desired gene expression pattern (e.g., temporal or spatial). Conditional promoters also can be operably linked to nucleic acid molecules of the invention to increase or decrease expression of the encoded polypeptide molecule in a regulated or conditional manner. Trans-acting negative or positive regulators of polypeptide activity or expression also can be operably linked to a conditional promoter as described above. Such trans-acting regulators include antisense nucleic acid molecules, nucleic acid molecules that encode dominant negative molecules, ribozyme molecules specific for nucleic acid molecules, and the like. The transgenic non-human animals are useful in experiments directed toward testing biochemical or physiological effects of diagnostics or therapeutics for conditions characterized by increased or decreased levels and/or increased or decreased stability of a GGA protein. Other uses will be apparent to one of ordinary skill in the art. Thus, the invention also permits the construction of gene alterations in cells and in animals, providing materials for studying certain aspects of Aβ accumulation-associated disorders.

According to another aspect of the invention, methods to modulate Aβ accumulation include use of one or more isolated GGA proteins or fragments thereof as Aβ accumulation-modulating compounds. Such proteins or fragments thereof may be useful to generate antibodies to single GGA proteins or to complexes of one or more GGA proteins. Fragments of one or more GGA proteins may also be useful to replace fully functional endogenous GGA proteins. If a GGA protein, or fragment thereof does not exhibit the GGA protein's function, it may be useful to replace or dilute out the fully functional endogenous GGA protein in a subject.

Proteins of the invention, and fragments thereof, can be isolated from biological samples including tissue or cell homogenates, and can also be expressed recombinantly in a variety of prokaryotic and eukaryotic expression systems by constructing an expression vector appropriate to the expression system, introducing the expression vector into the expression system, and isolating the recombinantly expressed protein. Short polypeptides, including antigenic peptides (such as those presented by MHC molecules on the surface of a cell for immune recognition) also can be synthesized chemically using well-established methods of peptide synthesis.

Thus, as used herein with respect to proteins, "isolated" means separated from its native environment and present in sufficient quantity to permit its identification or use. Isolated, when referring to a protein or polypeptide, means, for example: (i) selectively produced by expression of a recombinant nucleic acid or (ii) purified as by chromatography or electrophoresis. Isolated proteins or polypeptides may, but need not be, substantially pure. The term "substantially pure" means that the proteins or polypeptides are essentially free of other substances with which they may be found in nature or in vivo systems to an extent practical and appropriate for their intended use. Substantially pure proteins may be produced by techniques well known in the art. Because an isolated protein may be admixed with a pharmaceutically acceptable carrier in a pharmaceutical preparation, the protein may comprise only a small percentage by weight of the preparation. The protein is nonetheless isolated in that it has been separated from the substances with which it may be associated in living systems, e.g. isolated from other proteins.

The prevention and treatment methods of the invention include administration of Aβ accumulation-modulating compounds. Various techniques may be employed for introducing Aβ accumulation-modulating compounds of the invention to cells, depending on whether the compounds are introduced in vitro or in vivo in a host. In some embodiments, the Aβ accumulation-modulating compounds target neuronal cells and/or tissues. Thus, the Aβ accumulation-modulating compounds can be specifically targeted to neuronal tissue (e.g. neuronal cells) using various delivery methods, including, but not limited to: administration to neuronal tissue, the addition of targeting molecules to direct the compounds of the invention to neuronal cells and/or tissues. Additional methods to specifically target molecules and compositions of the invention to brain tissue and/or neuronal tissues are known to those of ordinary skill in the art.

In some embodiments of the invention, an Aβ accumulation-modulating compound of the invention may be delivered in the form of a delivery complex. The delivery complex may deliver the Aβ accumulation-modulating compound into any cell type, or may be associated with a molecule for targeting a specific cell type. Examples of delivery complexes include an Aβ accumulation-modulating compound of the invention associated with: a sterol (e.g., cholesterol), a lipid (e.g., a cationic lipid, virosome or liposome), or a target cell specific binding agent (e.g., an antibody, including but not limited to monoclonal antibodies, or a ligand recognized by target cell specific receptor). Some delivery complexes may be sufficiently stable in vivo to prevent significant uncoupling prior to internalization by the target cell. However, the delivery complex can be cleavable under appropriate conditions within the cell so that the Aβ accumulation-modulating compound is released in a functional form.

An example of a targeting method, although not intended to be limiting, is the use of liposomes to deliver an Aβ accumulation-modulating compound of the invention into a cell. Liposomes may be targeted to a particular tissue, such as neuronal cells, by coupling the liposome to a specific ligand such as a monoclonal antibody, sugar, glycolipid, or protein. Such proteins include proteins or fragments thereof specific for a particular cell type, antibodies for proteins that undergo internalization in cycling, proteins that target intracellular localization and enhance intracellular half life, and the like.

Liposomes are commercially available from Gibco BRL, for example, as LIPOFECTIN™ and LIPOFECTACE™, which are formed of cationic lipids such as N-[1-(2,3 dioleyloxy)-propyl]-N,N, N-trimethylammonium chloride (DOTMA) and dimethyl dioctadecylammonium bromide (DDAB). Methods for making liposomes are well known in the art and have been described in many publications. Liposomes also have been reviewed by Gregoriadis, G. in *Trends in Biotechnology*, 3:235-241 (1985).

When administered, the Aβ accumulation-modulating compounds (also referred to herein as therapeutic compounds and/or pharmaceutical compounds) of the present invention are administered in pharmaceutically acceptable preparations. Such preparations may routinely contain pharmaceutically acceptable concentrations of salt, buffering agents, preservatives, compatible carriers, and optionally other therapeutic agents.

The term "pharmaceutically acceptable" means a non-toxic material that does not interfere with the effectiveness of the biological activity of the active ingredients. The characteristics of the carrier will depend on the route of administration.

The therapeutics of the invention can be administered by any conventional route, including injection or by gradual infusion over time. The administration may, for example, be oral, intravenous, intrathecal, intraperitoneal, intramuscular, intranasal, intracavity, subcutaneous, intradermal, or transdermal.

The therapeutic compositions may conveniently be presented in unit dosage form and may be prepared by any of the methods well known in the art of pharmacy. All methods include the step of bringing the compounds into association with a carrier which constitutes one or more accessory ingredients. In general, the compositions are prepared by uniformly and intimately bringing the therapeutic agent into association with a liquid carrier, a finely divided solid carrier, or both, and then, if necessary, shaping the product.

Compositions suitable for parenteral administration conveniently comprise a sterile aqueous preparation of the therapeutic agent, which is preferably isotonic with the blood of the recipient. This aqueous preparation may be formulated according to known methods using those suitable dispersing or wetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables. Carrier formulations suitable for oral, subcutaneous, intravenous, intramuscular, etc. can be found in Remington's Pharmaceutical Sciences, Mack Publishing Company, Easton, Pa.

Compositions suitable for oral administration may be presented as discrete units such as capsules, cachets, tablets, or lozenges, each containing a predetermined amount of the therapeutic agent. Other compositions include suspensions in aqueous liquors or non-aqueous liquids such as a syrup, an elixir, or an emulsion.

The invention provides a composition of the above-described agents for use as a medicament, methods for preparing the medicament and methods for the sustained release of the medicament in vivo. Delivery systems can include time-release, delayed release or sustained release delivery systems. Such systems can avoid repeated administrations of the therapeutic agent of the invention, increasing convenience to the subject and the physician. Many types of release delivery systems are available and known to those of ordinary skill in the art. They include polymer-based systems such as polylactic and polyglycolic acid, poly(lactide-glycolide), copolyoxalates, polyanhydrides, polyesteramides, polyorthoesters, polyhydroxybutyric acid, and polycaprolactone. Microcapsules of the foregoing polymers containing drugs are described in, for example, U.S. Pat. No. 5,075,109. Nonpolymer systems that are lipids including sterols such as cholesterol, cholesterol esters and fatty acids or neutral fats such as mono-, di- and tri-glycerides; phospholipids; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. Nos. 4,452,775, 4,675,189, and 5,736,152, and (b) diffusional systems in which an active component permeates at a controlled rate from a polymer such as described in U.S. Pat. Nos. 3,854,480, 5,133,974 and 5,407,686. In addition, pump-based hardware delivery systems can be used, some of which are adapted for implantation.

In one particular embodiment, the preferred vehicle is a biocompatible microparticle or implant that is suitable for implantation into the mammalian recipient. Exemplary bioerodible implants that are useful in accordance with this method are described in PCT International application no. PCT/US95/03307 (Publication No. WO 95/24929, entitled "Polymeric Gene Delivery System". PCT/US95/03307 describes a biocompatible, preferably biodegradable polymeric matrix for containing an exogenous gene under the control of an appropriate promoter. The polymeric matrix is used to achieve sustained release of the exogenous gene in the patient. In accordance with the instant invention, the compound(s) of the invention is encapsulated or dispersed within the biocompatible, preferably biodegradable polymeric matrix disclosed in PCT/US95/03307. The polymeric matrix preferably is in the form of a microparticle such as a microsphere (wherein the compound is dispersed throughout a solid polymeric matrix) or a microcapsule (wherein the compound is stored in the core of a polymeric shell). Other forms of the polymeric matrix for containing the compounds of the invention include films, coatings, gels, implants, and stents. The size and composition of the polymeric matrix device is selected to result in favorable release kinetics in the tissue into which the matrix device is implanted. The size of the polymeric matrix device further is selected according to the method of delivery that is to be used. The polymeric matrix composition can be selected to have both favorable degradation rates and also to be formed of a material that is bioadhesive, to further increase the effectiveness of transfer when the devise is administered to a vascular surface. The matrix composition also can be selected not to degrade, but rather, to release by diffusion over an extended period of time.

Both non-biodegradable and biodegradable polymeric matrices can be used to deliver agents of the invention to the subject. Biodegradable matrices are preferred. Such polymers may be natural or synthetic polymers. Synthetic polymers are preferred. The polymer is selected based on the period of time over which release is desired, generally in the order of a few hours to a year or longer. Typically, release over a period ranging from between a few hours and three to twelve months is most desirable. The polymer optionally is in the form of a hydrogel that can absorb up to about 90% of its weight in water and further, optionally is cross-linked with multi-valent ions or other polymers.

In general, the agents of the invention are delivered using the bioerodible implant by way of diffusion, or more preferably, by degradation of the polymeric matrix. Exemplary synthetic polymers that can be used to form the biodegradable delivery system include: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and co-polymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxy-propyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulphate sodium salt, poly(methyl methacrylate), poly (ethyl methacrylate), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), poly(octadecyl acrylate), polyethylene, polypropylene, poly(ethylene glycol), poly(ethylene oxide), poly(ethylene terephthalate), poly(vinyl alcohols), polyvinyl acetate, poly vinyl chloride, polystyrene and polyvinylpyrrolidone.

Examples of non-biodegradable polymers include ethylene vinyl acetate, poly(meth)acrylic acid, polyamides, copolymers and mixtures thereof.

Examples of biodegradable polymers include synthetic polymers such as polymers of lactic acid and glycolic acid, polyanhydrides, poly(ortho)esters, polyurethanes, poly(butic acid), poly(valeric acid), and poly(lactide-cocaprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion.

Bioadhesive polymers of particular interest include bioerodible hydrogels described by H. S. Sawhney, C. P. Pathak and J. A. Hubell in Macromolecules, 1993, 26, 581-587, the teachings of which are incorporated herein by reference, polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly (isodecyl methacrylate), poly(lauryl methacrylate), poly (phenyl methacrylate), poly(methyl acrylate), poly(isopropyl acrylate), poly(isobutyl acrylate), and poly(octadecyl acrylate).

Use of a long-term sustained release implant may be particularly suitable for treatment of established neurological disorder conditions as well as subjects at risk of developing a neurological disorder. "Long-term" release, as used herein, means that the implant is constructed and arranged to deliver therapeutic levels of the active ingredient for at least 7 days, and preferably 30-60 days. The implant may be positioned at or near the site of the neurological damage or the area of the brain or nervous system affected by or involved in the neurological disorder. Long-term sustained release implants are well known to those of ordinary skill in the art and include some of the release systems described above.

Some embodiments of the invention include methods for treating a subject to reduce the risk of a disorder associated with abnormal levels and/or activity of a GGA protein or GGA protein complex, such as diseases in which Aβ is elevated, including Alzheimer's disease. The methods involve selecting and administering to a subject who is known to have, is suspected of having, or is at risk of having an abnormal level and/or activity of a GGA protein or GGA protein complex, an Aβ accumulation-modulating compound for treating the disorder. Preferably, the Aβ accumulation-modulating compound is a compound for modulating (e.g., increasing) levels and/or activity of a GGA protein or GGA protein complex and is administered in an amount effective to modulate (increase) levels and/or activity of a GGA protein or GGA protein complex.

Another aspect of the invention involves reducing the risk of a disorder associated with abnormal levels and/or activity of a GGA protein or GGA protein complex means using treatments and/or medications to modulate levels of a GGA protein or GGA protein complex, therein reducing, for example, the subject's risk of an Aβ accumulation-associated disorder of the invention.

In a subject determined to have an Aβ-accumulation-associated disorder, an effective amount of an Aβ accumulation-modulating compound is that amount effective to modulate (e.g., decrease) levels of Aβ accumulation in the subject. For example, in the case of Alzheimer's disease, an effective amount may be an amount that increases the abnormally low level and/or activity of a GGA protein or GGA protein complex, in the subject, thereby promoting BACE degradation and reducing levels of Aβ produced in the subject.

A response to a prophylatic and/or treatment method of the invention can, for example, also be measured by determining the physiological effects of the treatment or medication, such as the decrease or lack of disease symptoms following administration of the treatment or pharmacological agent. Other assays will be known to one of ordinary skill in the art and can be employed for measuring the level of the response. For example, the behavioral and neurological diagnostic methods that are used to ascertain the likelihood that a subject has Alzheimer's disease, and to determine the putative stage of the disease can be used to ascertain the level of response to a prophylactic and/or treatment method of the invention. The amount of a treatment may be varied for example by increasing or decreasing the amount of a therapeutic composition, by changing the therapeutic composition administered, by changing the route of administration, by changing the dosage timing and so on. The effective amount will vary with the particular condition being treated, the age and physical condition of the subject being treated, the severity of the condition, the duration of the treatment, the nature of the concurrent therapy (if any), the specific route of administration, and the like factors within the knowledge and expertise of the health practitioner. For example, an effective amount can depend upon the degree to which an individual has abnormal levels and/or activity of a GGA protein or GGA protein complex.

The factors involved in determining an effective amount are well known to those of ordinary skill in the art and can be addressed with no more than routine experimentation. It is generally preferred that a maximum dose of the pharmacological agents of the invention (alone or in combination with other therapeutic agents) be used, that is, the highest safe dose according to sound medical judgment. It will be understood by those of ordinary skill in the art however, that a patient may insist upon a lower dose or tolerable dose for medical reasons, psychological reasons or for virtually any other reasons.

The therapeutically effective amount of a pharmacological agent of the invention is that amount effective to modulate $A\beta$ accumulation, and/or the level or activity of a GGA protein or GGA protein complex and reduce, prevent, or eliminate the $A\beta$ accumulation-associated disorder. For example, testing can be performed to determine the level and/or activity of a GGA protein or GGA protein complex in a subject's tissue and/or cells. Additional tests useful for monitoring the onset, progression, and/or remission, of $A\beta$ accumulation-associated disorders such as those described above herein, are well known to those of ordinary skill in the art. As would be understood by one of ordinary skill, for some disorders (e.g., Alzheimer's disease) an effective amount is the amount of a pharmacological agent of the invention that increases the level and/or activity of a GGA protein or GGA protein complex to a level and/or activity that diminishes the disorder, as determined by the aforementioned tests.

In the case of treating a particular disease or condition the desired response is inhibiting the progression of the disease or condition. This may involve only slowing the progression of the disease temporarily, although more preferably, it involves halting the progression of the disease permanently. This can be monitored by routine diagnostic methods known to one of ordinary skill in the art for any particular disease. The desired response to treatment of the disease or condition also can be delaying the onset or even preventing the onset of the disease or condition.

The pharmaceutical compositions used in the foregoing methods preferably are sterile and contain an effective amount of a pharmacological agent for producing the desired response in a unit of weight or volume suitable for administration to a patient.

The doses of pharmacological agents administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits. The dosage of a pharmacological agent of the invention may be adjusted by the individual physician or veterinarian, particularly in the event of any complication. A therapeutically effective amount typically varies from 0.01 mg/kg to about 1000 mg/kg, preferably from about 0.1 mg/kg to about 200 mg/kg, and most preferably from about 0.2 mg/kg to about 20 mg/kg, in one or more dose administrations daily, for one or more days.

Various modes of administration will be known to one of ordinary skill in the art which effectively deliver the pharmacological agents of the invention to a desired tissue, cell, or bodily fluid. The administration methods include: topical, intravenous, oral, inhalation, intracavity, intrathecal, intrasynovial, buccal, sublingual, intranasal, transdermal, intravitreal, subcutaneous, intramuscular and intradermal administration. The invention is not limited by the particular modes of administration disclosed herein. Standard references in the art (e.g., *Remington's Pharmaceutical Sciences,* 18th edition, 1990) provide modes of administration and formulations for delivery of various pharmaceutical preparations and formulations in pharmaceutical carriers. Other protocols which are useful for the administration of pharmacological agents of the invention will be known to one of ordinary skill in the art, in which the dose amount, schedule of administration, sites of administration, mode of administration (e.g., intra-organ) and the like vary from those presented herein.

Administration of pharmacological agents of the invention to mammals other than humans, e.g. for testing purposes or veterinary therapeutic purposes, is carried out under substantially the same conditions as described above. It will be understood by one of ordinary skill in the art that this invention is applicable to both human and animal diseases including $A\beta$ accumulation-associated disorders of the invention. Thus, this invention is intended to be used in husbandry and veterinary medicine as well as in human therapeutics.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. Preferred components of the composition are described above in conjunction with the description of the pharmacological agents and/or compositions of the invention.

A pharmacological agent or composition may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the pharmacological agents of the invention, and with each other, in a manner such that there is no interaction which would substantially impair the desired pharmaceutical efficacy.

The pharmaceutical compositions may contain suitable buffering agents, as described above, including: acetate, phosphate, citrate, glycine, borate, carbonate, bicarbonate, hydroxide (and other bases) and pharmaceutically acceptable salts of the foregoing compounds. The pharmaceutical compositions also may contain, optionally, suitable preservatives, such as: benzalkonium chloride, chlorobutanol and parabens.

The pharmaceutical compositions may conveniently be presented in unit dosage form and may be prepared by any of the methods well known in the art of pharmacy. All methods include the step of bringing the active agent into association with a carrier, which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration may be formulated according to known methods using suitable dispersing or wetting agents and suspending agents. The sterile injectable preparation also may be a sterile injectable solution or suspension in a non-toxic parenterally acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the preparation of injectables. Carrier formulation suitable for oral, subcutaneous, intravenous, intramuscular, etc. administrations can be found in *Remington's Pharmaceutical Sciences*, Mack Publishing Co., Easton, Pa.

In general, the treatment methods involve administering an agent to modulate the level and/or activity of a GGA protein or GGA protein complex. Thus, these methods include gene therapy applications. The procedure for performing ex vivo gene therapy is outlined in U.S. Pat. No. 5,399,346 and in exhibits submitted in the file history of that patent, all of which are publicly available documents. In general, it involves introduction in vitro of a functional copy of a gene into a cell(s) of a subject which contains a defective copy of the gene, and returning the genetically engineered cell(s) to the subject. The functional copy of the gene is under operable control of regulatory elements, which permit expression of the gene in the genetically engineered cell(s). Numerous transfection and transduction techniques as well as appropriate expression vectors are well known to those of ordinary skill in the art, some of which are described in PCT application WO95/00654. In vivo gene therapy using vectors such as adenovirus, retroviruses, herpes virus, and targeted liposomes also is contemplated according to the invention. Preferred target cells for ex vivo and in vivo therapy include neurons and stem cells that can differentiate into a variety of cells.

In certain embodiments, the method for treating a subject with a disorder characterized by abnormal levels and/or activity of a GGA protein or GGA protein complex, involves administering to the subject an effective amount of a nucleic acid molecule to treat the disorder. In certain of these embodiments, the method for treatment involves administering to the subject an effective amount of an antisense, RNAi, or siRNA oligonucleotide to reduce the level of a GGA protein or GGA protein complex and thereby, treat the disorder. An exemplary molecule for modulating the level and/or activity of a GGA protein or GGA protein complex is an antisense molecule that is selective for the nucleic acid encoding a GGA protein. Alternatively, the method for treating a subject with a disorder characterized by abnormal levels and/or activity of a GGA protein or GGA protein complex involves administering to the subject an effective amount of a GGA protein (or the nucleic acid that encodes such a protein) that has reduced or no normal GGA protein function to treat the disorder.

In yet another embodiment, the treatment method involves administering to the subject an effective amount of a binding polypeptide (e.g., antibody, or antigen-binding fragment thereof) to modulate binding between one or more proteins of the invention and, thereby, treat the disorder. In some embodiments, the treatment method involves administering to the subject an effective amount of a binding polypeptide to inhibit or enhance the level and/or activity of a GGA protein or GGA protein complex to decrease or increase A$\beta$ production activity, respectively. In certain preferred embodiments, the binding polypeptide is an antibody or an antigen-binding fragment thereof; the antibodies or antigen-binding fragments may be labeled with detectable agent(s) for diagnostic applications.

According to yet another aspect of the invention, expression vectors comprising any of the isolated nucleic acid molecules of the invention, preferably operably linked to a promoter are provided. In a related aspect, host cells transformed or transfected with such expression vectors also are provided. Expression vectors containing all the necessary elements for expression are commercially available and known to those skilled in the art. See, e.g., Sambrook et al., *Molecular Cloning: A Laboratory Manual*, Second Edition, Cold Spring Harbor Laboratory Press, 1989. Cells are genetically engineered by the introduction into the cells of heterologous DNA (RNA) encoding a protein of the invention, fragment, or variant thereof. The heterologous DNA (RNA) is placed under operable control of transcriptional elements to permit the expression of the heterologous DNA in the host cell.

As used herein, a "vector" may be any of a number of nucleic acid molecules into which a desired sequence may be inserted by restriction and ligation for transport between different genetic environments or for expression in a host cell. Vectors are typically composed of DNA although RNA vectors are also available. Vectors include, but are not limited to, plasmids, phagemids and virus genomes. A cloning vector is one which is able to replicate in a host cell, and which is further characterized by one or more endonuclease restriction sites at which the vector may be cut in a determinable fashion and into which a desired DNA sequence may be ligated such that the new recombinant vector retains its ability to replicate in the host cell. In the case of plasmids, replication of the desired sequence may occur many times as the plasmid increases in copy number within the host bacterium or just a single time per host before the host reproduces by mitosis. In the case of phage, replication may occur actively during a lytic phase or passively during a lysogenic phase.

An expression vector is one into which a desired DNA sequence may be inserted by restriction and ligation such that it is operably joined to regulatory sequences and may be expressed as an RNA transcript. Vectors may further contain one or more marker sequences suitable for use in the identification of cells that have or have not been transformed or transfected with the vector. Markers include, for example, genes encoding proteins that increase or decrease either resistance or sensitivity to antibiotics or other compounds, genes that encode enzymes whose activities are detectable by standard assays known in the art (e.g., $\beta$-galactosidase or alkaline phosphatase), and genes that visibly affect the phenotype of transformed or transfected cells, hosts, colonies or plaques (e.g., green fluorescent protein). Preferred vectors are those capable of autonomous replication and expression of the structural gene products present in the DNA segments to which they are operably joined.

As used herein, a coding sequence and regulatory sequences are said to be "operably" joined when they are covalently linked in such a way as to place the expression or transcription of the coding sequence under the influence or control of the regulatory sequences. If it is desired that the coding sequences be translated into a functional protein, two DNA sequences are said to be operably joined if induction of a promoter in the 5' regulatory sequences results in the transcription of the coding sequence and if the nature of the linkage between the two DNA sequences does not (1) result in the introduction of a frame-shift mutation, (2) interfere with the ability of the promoter region to direct the transcription of the coding sequences, or (3) interfere with the ability of the corresponding RNA transcript to be translated into a protein. Thus, a promoter region would be operably joined to a coding sequence if the promoter region were capable of effecting transcription of that DNA sequence such that the resulting transcript might be translated into the desired protein or polypeptide.

The precise nature of the regulatory sequences needed for gene expression may vary between species or cell types, but shall in general include, as necessary, 5' non-transcribed and 5' non-translated sequences involved with the initiation of transcription and translation respectively, such as a TATA box, capping sequence, CAAT sequence, and the like. Especially, such 5' non-transcribed regulatory sequences will include a promoter region that includes a promoter sequence for transcriptional control of the operably joined gene. Regulatory sequences may also include enhancer sequences or upstream activator sequences as desired. The vectors of the invention may optionally include 5' leader or signal sequences. The choice and design of an appropriate vector is within the ability and discretion of one of ordinary skill in the art.

In some embodiments, a virus vector for delivering a nucleic acid molecule encoding a GGA protein of the invention (e.g., GGA1, GGA2, and/or GGA3 proteins), fragment thereof, antisense molecule, RNAi, or siRNA molecule of the invention, is selected from the group consisting of adenoviruses, adeno-associated viruses, poxviruses including vaccinia viruses and attenuated poxviruses, Semliki Forest virus, Venezuelan equine encephalitis virus, retroviruses, Sindbis virus, and Ty virus-like particle. Examples of viruses and virus-like particles which have been used to deliver exogenous nucleic acids include: replication-defective adenoviruses (e.g., Xiang et al., *Virology* 219:220-227, 1996; Eloit et al., *J. Virol.* 7:5375-5381, 1997; Chengalvala et al., *Vaccine* 15:335-339, 1997), a modified retrovirus (Townsend et al., *J. Virol.* 71:3365-3374, 1997), a nonreplicating retrovirus (Irwin et al., *J. Virol.* 68:5036-5044, 1994), a replication defective Semliki Forest virus (Zhao et al., *Proc. Natl. Acad. Sci. USA* 92:3009-3013, 1995), canarypox virus and highly attenuated vaccinia virus derivative (Paoletti, *Proc. Natl. Acad. Sci. USA* 93:11349-11353, 1996), non-replicative vaccinia virus (Moss, *Proc. Natl. Acad. Sci. USA* 93:11341-11348, 1996), replicative vaccinia virus (Moss, *Dev. Biol. Stand.* 82:55-63, 1994), Venzuelan equine encephalitis virus (Davis et al., *J. Virol.* 70:3781-3787, 1996), Sindbis virus (Pugachev et al., *Virology* 212:587-594, 1995), and Ty virus-like particle (Allsopp et al., *Eur. J. Immunol.* 26:1951-1959, 1996). In preferred embodiments, the virus vector is an adenovirus.

Another preferred virus for certain applications is the adeno-associated virus, a double-stranded DNA virus. The adeno-associated virus is capable of infecting a wide range of cell types and species and can be engineered to be replication-deficient. It further has advantages, such as heat and lipid solvent stability, high transduction frequencies in cells of diverse lineages, including hematopoietic cells, and lack of superinfection inhibition thus allowing multiple series of transductions. The adeno-associated virus can integrate into human cellular DNA in a site-specific manner, thereby minimizing the possibility of insertional mutagenesis and variability of inserted gene expression. In addition, wild-type adeno-associated virus infections have been followed in tissue culture for greater than 100 passages in the absence of selective pressure, implying that the adeno-associated virus genomic integration is a relatively stable event. The adeno-associated virus can also function in an extrachromosomal fashion.

In general, other preferred viral vectors are based on non-cytopathic eukaryotic viruses in which non-essential genes have been replaced with the gene of interest. Non-cytopathic viruses include retroviruses, the life cycle of which involves reverse transcription of genomic viral RNA into DNA with subsequent proviral integration into host cellular DNA. Adenoviruses and retroviruses have been approved for human gene therapy trials. In general, the retroviruses are replication-deficient (i.e., capable of directing synthesis of the desired proteins, but incapable of manufacturing an infectious particle). Such genetically altered retroviral expression vectors have general utility for the high-efficiency transduction of genes in vivo. Standard protocols for producing replication-deficient retroviruses (including the steps of incorporation of exogenous genetic material into a plasmid, transfection of a packaging cell lined with plasmid, production of recombinant retroviruses by the packaging cell line, collection of viral particles from tissue culture media, and infection of the target cells with viral particles) are provided in Kriegler, M., "Gene Transfer and Expression, A Laboratory Manual," W.H. Freeman Co., New York (1990) and Murry, E. J. Ed. "Methods in Molecular Biology," vol. 7, Humana Press, Inc., Clifton, N.J. (1991).

Preferably the foregoing nucleic acid delivery vectors: (1) contain exogenous genetic material that can be transcribed and translated in a mammalian cell and that can suppress Aβ accumulation-associated disorders, and preferably (2) contain on a surface a ligand that selectively binds to a receptor on the surface of a target cell, such as a mammalian cell, and thereby gains entry to the target cell.

Various techniques may be employed for introducing nucleic acid molecules of the invention into cells, depending on whether the nucleic acid molecules are introduced in vitro or in vivo in a host. Such techniques include transfection of nucleic acid molecule-calcium phosphate precipitates, transfection of nucleic acid molecules associated with DEAE, transfection or infection with the foregoing viruses including the nucleic acid molecule of interest, liposome-mediated transfection, and the like. For certain uses, it is preferred to target the nucleic acid molecule to particular cells. In such instances, a vehicle used for delivering a nucleic acid molecule of the invention into a cell (e.g., a retrovirus, or other virus; a liposome) can have a targeting molecule attached thereto. For example, a molecule such as an antibody specific for a surface membrane protein on the target cell or a ligand for a receptor on the target cell can be bound to or incorporated within the nucleic acid molecule delivery vehicle. Especially preferred are monoclonal antibodies. Where liposomes are employed to deliver the nucleic acid molecules of the invention, proteins that bind to a surface membrane protein associated with endocytosis may be incorporated into the liposome formulation for targeting and/or to facilitate uptake. Such proteins include capsid proteins or fragments thereof tropic for a particular cell type, antibodies for proteins which undergo internalization in cycling, proteins that target intracellular localization and enhance intracellular half life, and the like. Polymeric delivery systems also have been used successfully to deliver nucleic acid molecules into cells, as is known by those skilled in the art. Such systems even permit oral delivery of nucleic acid molecules.

In addition to delivery through the use of vectors, nucleic acids of the invention may be delivered to cells without vectors, e.g., as "naked" nucleic acid delivery using methods known to those of skill in the art.

The invention will be more fully understood by reference to the following examples. These examples, however, are merely intended to illustrate the embodiments of the invention and are not to be construed to limit the scope of the invention.

EXAMPLES

Example 1

Role of GGA3 on BACE Stabilization/Degradation

We have previously shown that BACE protein levels increase during apoptosis in a number of cell lines. We have also found that the increase in BACE protein levels leads to increased processing of APP by β-secretase. We have also discovered that the elevated activity of β-secretase during apoptosis is the result of increased protein stability of BACE following caspase activation. Caspase inhibition by treatment with zVAD, a broad spectrum caspase inhibitor is able to prevent the stabilization of BACE and the increase in Aβ production. See US published application 2004-0219610.

BACE is Degraded by the Lysosomes

It has been shown that lysosomal inhibitors, chloroquine and $NH_4Cl$, lead to accumulation of endogenous and ectopically expressed BACE in a variety of cell types, including primary neurons (Koh et al., 2005). Furthermore, the inhibition of lysosomal hydrolases results in the redistribution and accumulation of BACE in the late endosomal/lysosomal compartments (lysosome-associated membrane protein 2, LAMP2, positive). In contrast, the BACE LL/AA mutant, in which $Leu^{499}$ and $Leu^{500}$ in the C-terminal sequence (DDIS-LLK) were replaced by alanines, only partially co-localized with LAMP2-positive compartments following inhibition of lysosomal hydrolases. Collectively, these data indicate that BACE is transported to the late endosomal/lysosomal compartments where it is degraded via the lysosomal pathway, and that the di-leucine motif plays a role in sorting BACE to lysosomes.

Cerebral Ischemia Increases Protein Levels of BACE In Vivo

Since previous studies have shown that caspase 3 activation can be detected following cerebral ischemia from 1 to 24 hr after reperfusion both in mice and in rats (Davoli et al., 2002; Namura et al., 1998), we next asked whether caspase activation associated with cerebral ischemia leads to increased levels of BACE protein in vivo. For this purpose, we used both rat and mouse models of cerebral ischemia. Simpkins and coworkers have recently shown that BACE protein levels and activity are increased following cerebral ischemia in rats (Wen et al., 2004).

Figure 4A:
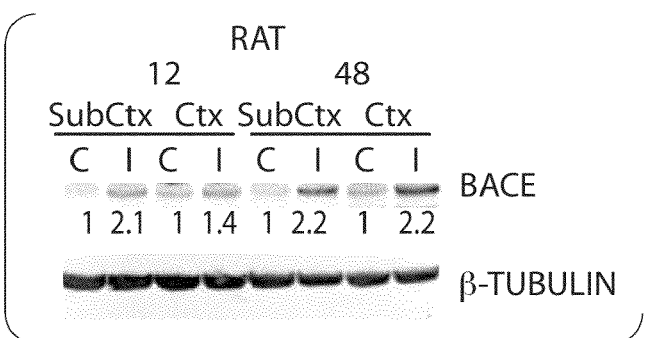
FIG. 4a-b: The number below each bands indicates the fold increase of BACE protein levels in the I hemisphere vs. the C hemisphere. β-tubulin or an aspecific band was used as loading control.

In collaboration with Dr. James Simpkins at the University of North Texas, we confirmed that cerebral ischemia increases BACE protein levels in rats. Female Charles River Sprague-Dawley rats (250 g, Wilmington, Mass.) were acclimatized for three days before surgery. Bilateral ovariectomy was performed 2 weeks before the occlusion of the middle cerebral artery (MCAO). The University of North Texas Health Science Center Animal Care and Use Committee approved all animal procedures. Ischemic stroke was induced by MCAO as described before (Liu et al., 2002). Briefly, animals were anesthetized by intraperitoneal injection of ketamine (60 mg/kg) and xylazine (10 mg/kg). Rectal temperature was maintained at 37.5±0.5° C. during the procedure. The left MCA was occluded by a 3-0 monofilament suture, which was introduced via internal carotid artery. After one-hour MCAO, the suture was withdrawn for reperfusion. The animals were anesthetized and decapitated at the desired time after the onset of reperfusion (12, 24 and 48 hr). The brains were harvested, separated into ischemic and non-ischemic hemisphere, dissected in cortex (Ctx) and sub-cortex (Sub-Ctx), and frozen in liquid nitrogen. Then, the samples were homogenized in RIPA buffer and analyzed by Western Blot. Quantification was performed using a Versadoc Imager and analyzed using QuantityOne software (BioRad) (FIG. 4a). BACE protein levels were significantly increased (>2-fold) in the ischemic (ipsilateral) cortical and sub-cortical hemispheres (but not in the contralateral hemispheres) at 12 and 48 hr following induction of cerebral ischemia.

Figure 4B:

To confirm these findings, in collaboration with Dr. Michael Moskowitz at Massachusetts General Hospital, we also measured BACE protein levels following induction of cerebral ischemia in a murine model utilizing transient MCAO. We chose to utilize this model of reversible ischemia because injury tends to be milder, and apoptosis is more prominent (Bonfoco et al., 1995). Dr. Moskowitz has extensively shown that in this model caspase activation occurs (Namura et al., 1998) and that intracerebroventricular injection of z-VAD.FMK or zDEVD.FMK before ischemia and immediately after reperfusion significantly reduces ischemic and excitotoxic neuronal damage (Hara et al., 1997). Focal cerebral ischemia was induced by MCAO using the intraluminal filament technique (Namura et al., 1998) in male C57BL/6 mice (20-25 g). The occlusion of MCA was performed for 1 hour, and then the filament was removed to allow reperfusion. Mice were sacrificed after 6, 12, 24, and 48 hours. Lysates were prepared from the ispilateral (ischemic) and contralateral (non-ischemic) hemispheres as described above. Protein levels of BACE were determined by quantitative Western Blot analysis (FIG. 4b). As observed in the ischemic rat model, BACE protein levels were significantly increased in the ischemic (ipsilateral) but not the contralateral hemispheres following MCAO. In agreement with the in vitro studies, in the mouse ischemia model, increases in BACE levels were observed as early as 6 hours after ischemia was induced.

Figure 4C:
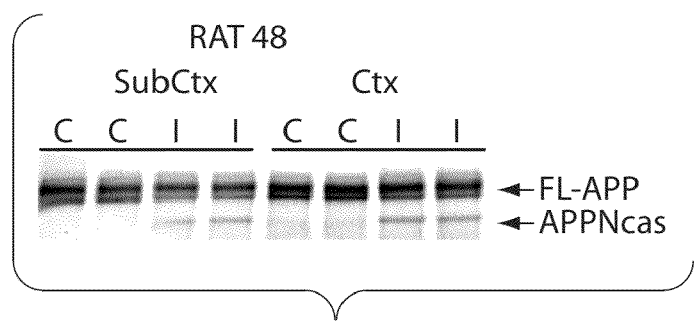
FIG. 4c: WB with an anti-APP-CTF antibody (A8717, Sigma) revealed an APP caspase-derived fragment in the rat ischemic hemisphere (samples were run in duplicate) after 48 hr of reperfusion.

Several studies have shown cerebral ischemia to upregulate APP messages containing the Kunitz-type protease inhibitor domain, between 1 and 21 days after reperfusion (Abe et al., 1991; Kim et al., 1998; Koistinaho et al., 1996; Shi et al., 2000). APP protein levels were increased between 1 and 10 weeks after reperfusion (Banati et al., 1995; Kalaria et al., 1993; Stephenson et al., 1992; Wakita et al., 1992). Thus, we have studied protein levels of APP in the rat brain following ischemia and found that APP protein levels are not increased but actually slightly decreased owing to the processing of full-length APP in a fragment of roughly 90 kDa after 48 hours of reperfusion (FIG. 4c). We have previously reported that caspase-mediated cleavage of APP generates a similar fragment in cells during apoptosis (Tesco et al. JBC 2003). These new data indicate that caspase activation/apoptosis is occurring following ischemia in our animal model.

Example 2

GGA3 is Cleaved During Apoptosis and Experimental Cerebral Ischemia In Vivo

Figure 5A:
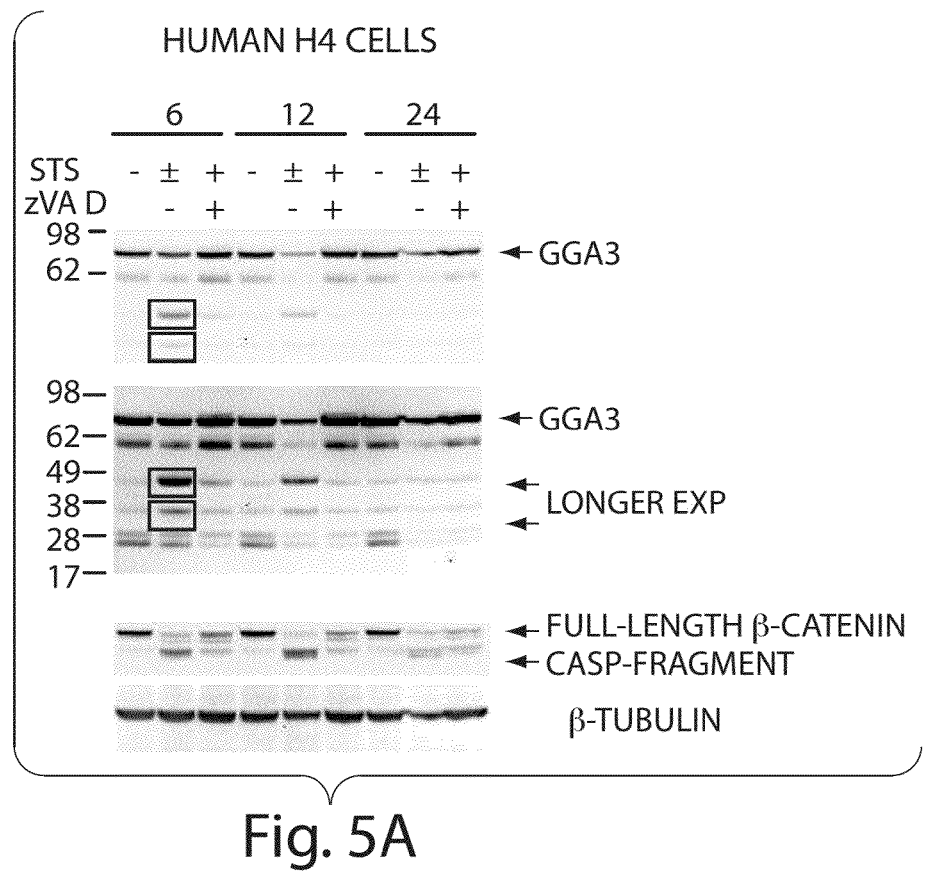
FIG. 5a: Western blot analysis with an anti-GGA3 antibody revealed cleavage of GGA3 in two major fragments in apoptotic H4 cells, which was prevented by caspase inhibition (zVAD).

We have found that GGA3 is cleaved during apoptosis and that its cleavage is inhibited by zVAD (FIG. 5). H4 cells were treated with staurosporine (STS) during time course experiments. Western Blot analysis with anti-GGA3 Ab (Transduction Laboratories) revealed that full length GGA3 was cleaved in two major fragments of ~48 and ~37 kDa during apoptosis. Interestingly, β-catenin, which is a caspase substrate (Brancolini et al., 1998), is cleaved in H4 cells with a pattern similar to GGA3 (FIG. 5a).

Figure 5B:
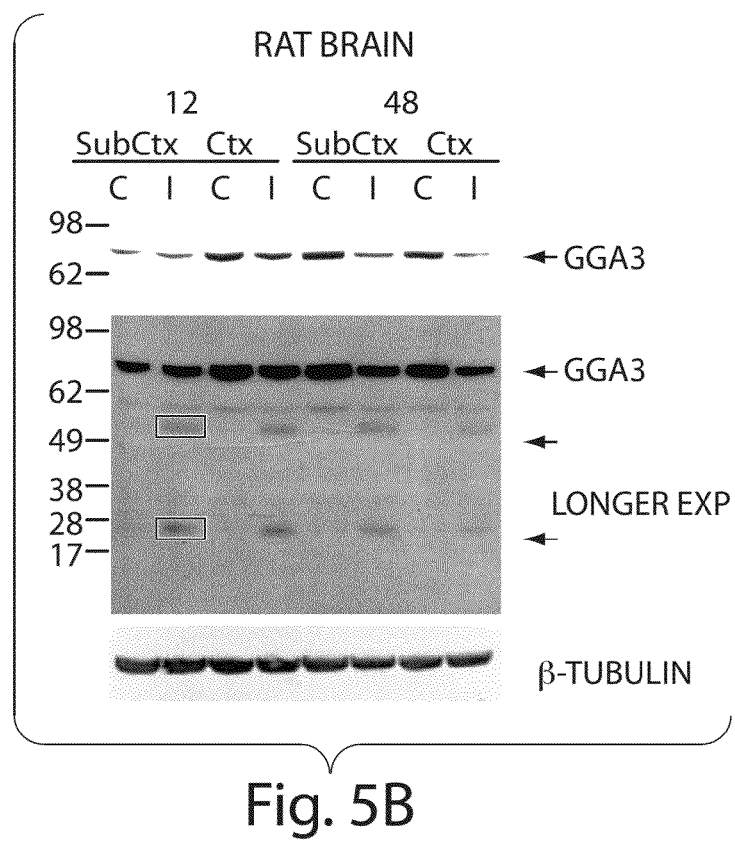
FIG. 5b: rat brain samples from the experiment described in FIG. 7. WB analysis with anti-GGA3 antibody revealed a decrease in GGA3 full-length and a longer exposure two fragments of GGA3 generated during ischemia (C=contralateral hemisphere; I=ipsilateral hemisphere; SubCtx=subcortex; Ctx=cortex).
Figure 5C:
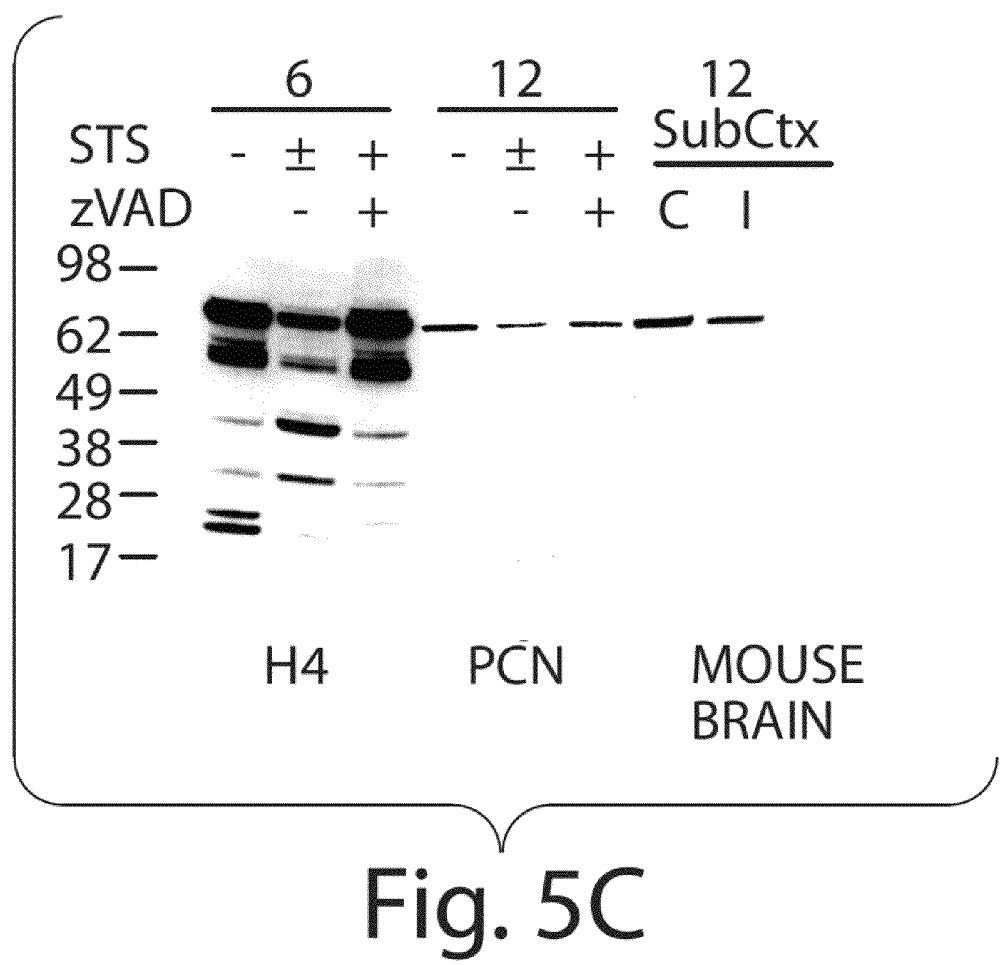
FIG. 5c: H4 and primary cortical neurons (PCN) were treated with STS for 12 hr. WB with anti-GGA3 antibody detected a decrease in full length GGA3 in PCN and in the ischemic (I) hemisphere of mouse brain.

We next asked whether GGA3 undergoes a similar cleavage during cerebral ischemia. We found that GGA3 is also cleaved during cerebral ischemia in both rats and in mice with a temporal pattern similar to the one observed for the increase in BACE protein levels (FIG. 5b, FIG. 5c). GGA3 full length was decreased both in the rat and in mouse ischemic hemisphere samples. Two cleaved fragments, fragment 1 of ~50 kDa and fragment 2 of ~28 kDa, were detected in the ischemic rat hemisphere, while in the mouse ischemic hemisphere no fragment was detected, most likely because the fragment levels are below the level of detection. The difference in size of the two fragments in human H4 cells and in rat brain could be due to the variation of amino acid sequence in the rat versus human GGA3 protein. However, the sequence for the rat GGA3 is not available in GenBank. We have found that GGA3 is also cleaved in primary neuronal cultures as indicated by the decrease of full length GGA3, however the cleaved fragments were not detected, most likely because their levels are below the level of detection (FIG. 5c).

Example 3

Caspase 3 Cleaves GGA3 at Three Major Sites Including D313

Figure 6A:
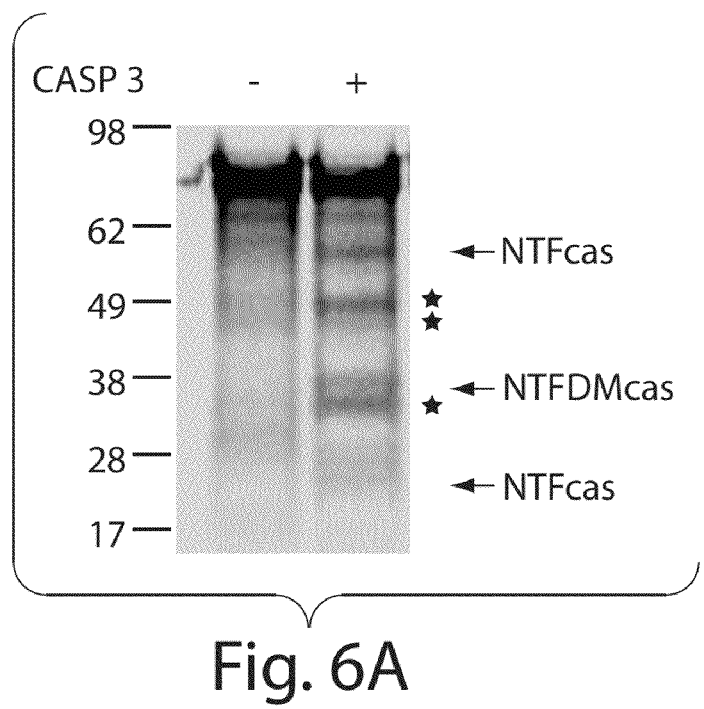
FIG. 6a: recombinant caspase 3 cleaves in vitro translated GGA3 (labeled with [$^{35}$S] methionine) in several fragments.

Since during apoptosis and ischemia many proteases are activated, we used an in vitro cell-free assay to determine whether caspases are the protease responsible for the cleavage of GGA3. GGA3 was in vitro translated (IVT) in the presence of [$^{35}$S]-labeled methionine using TNT Quick Coupled Transcription/Translation Systems as indicated by the manufacturer (Promega). 5 μL of IVT reaction were incubated with or without 200 ng of recombinant caspase 3 (Pharmingen) in caspase reaction buffer (sucrose 20%, NaCl 100 mM, HEPES (pH 7.4) 20 mM, CHAPS 0.1%, DTT 10 mM, EDTA 1 mM) at 37° for 2 hr. The reactions were separated by SDS-page (4-12% Bis-tricine gel with MES running buffer, Invitrogen). The gel was fixed, dried and exposed to a phosphorimager screen. The images were acquired with a FX phosphorimager (Bio-Rad). Recombinant caspase 3 cleaved in vitro translated GGA3 in several fragments (FIG. 6a).

Figure 6B:
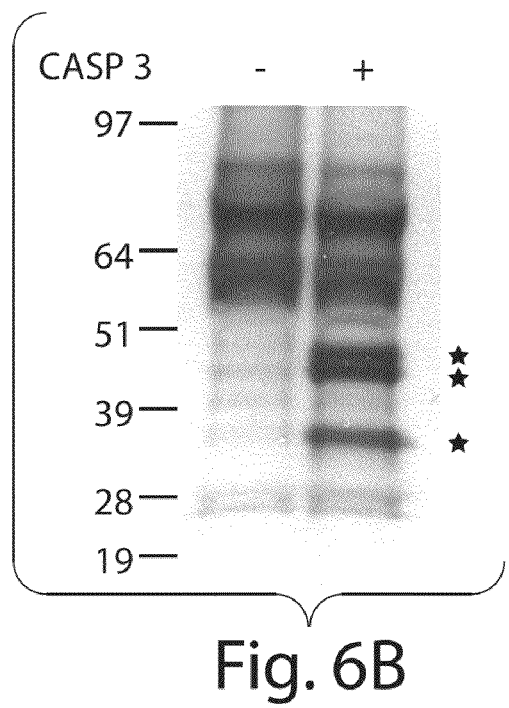

In order to determine which of these fragments correspond to the ones detected in the apoptotic lysates by Western Blot analysis, GGA3 was in vitro translated in the presence of cold methionine. Then, 5 μL of IVT reaction were incubated with or without 200 ng of recombinant caspase 3 overnight at 37° C. The reactions were separated by SDS-PAGE. In order to better separate the bands generated by caspase 3 cleavage we used 12% Bis-tricine gel and MOPS running buffer (Invitrogen). Then, the proteins were transferred to PVDF membrane. Western Blot analysis with anti-GGA3 antibody (Ab) revealed that recombinant caspase 3 cleaves in vitro translated GGA3 (cold methionine) in three fragments (FIG. 6b). Therefore, the additional caspase 3-derived fragments detected only in the autoradiography are N-terminal fragments (FIG. 6a).

Figure 6C:
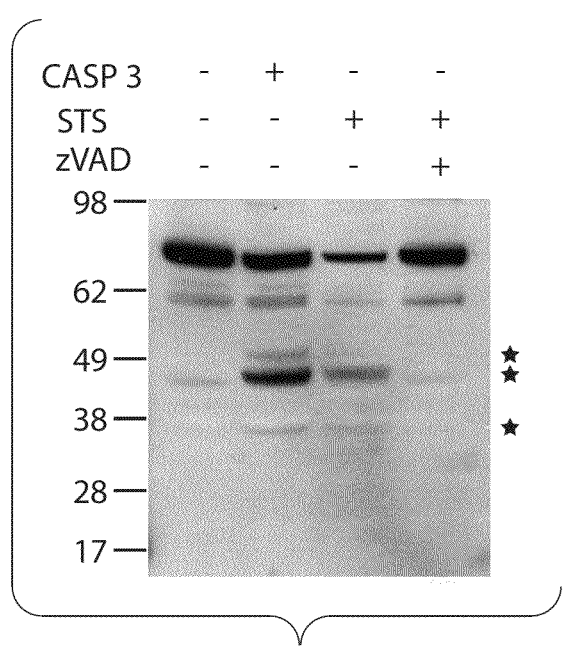
FIG. 6c: recombinant caspase 3 cleaves endogenous GGA3 from lysates of control cells with a pattern similar to the one observed in H4 apoptotic lysates.
Figure 6D:
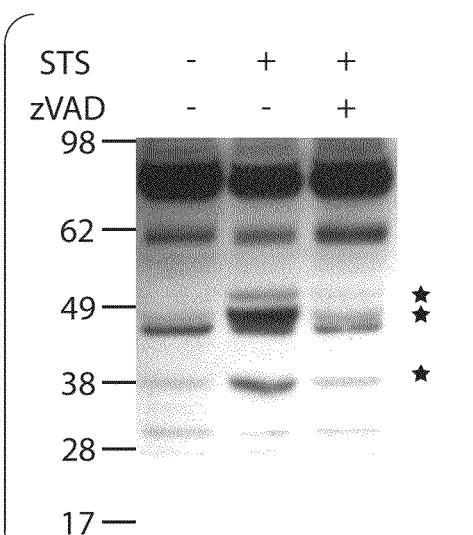
FIG. 6d: apoptosis induced in H4 cells overexpressing GGA3 produces a cleavage of GGA3 identical to the one produced by recombinant caspase 3.

We next asked whether recombinant caspase 3 cleaves endogenous GGA3 with a pattern similar to the one observed in apoptotic cells. Lysates of control cells were incubated with 200 ng of recombinant caspase 3 at 37° C. for 2 hr. Western Blot analysis with the anti-GGA3 Ab revealed that recombinant caspase 3 cleaves endogenous GGA3 with a pattern identical to the one observed in the in vitro assay (three fragments). However, the highest fragment (fragment 1) was not detected in H4 apoptotic lysates. One possible explanation is that its levels were below the levels of detection (FIG. 6c). To address this possibility apoptosis was induced by STS treatment in H4 cells overexpressing GGA3. We found that caspase activation produces a cleavage of GGA3 identical to the one produced by recombinant caspase 3 in both WT and endogenous GGA3 proteins (FIG. 6d). These data indicate that caspase 3 cleaves GGA3 during apoptosis.

Figure 6E:
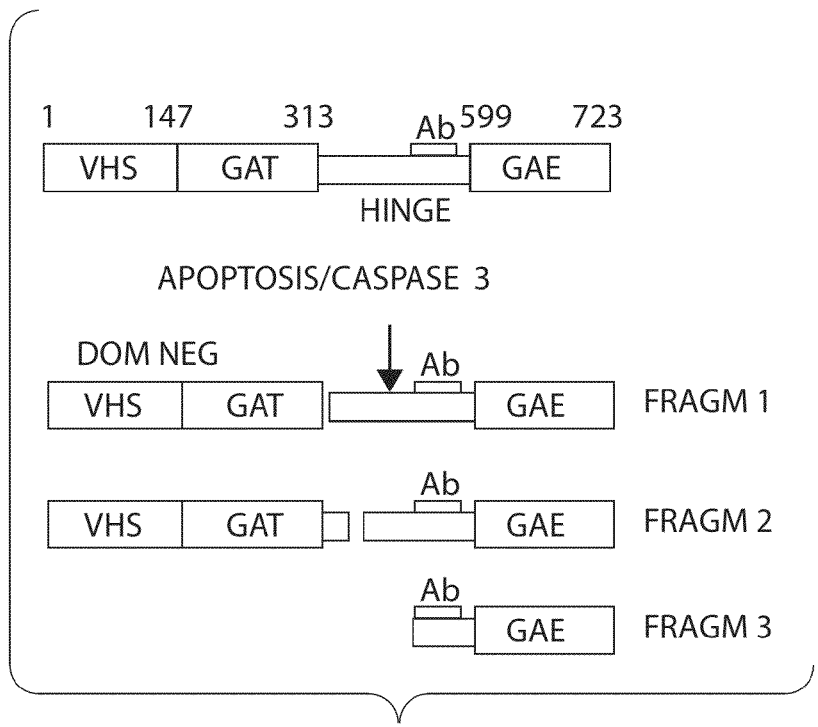
FIG. 6e: Schematic representation of GGA3 caspase cleavage.
Figure 6F:
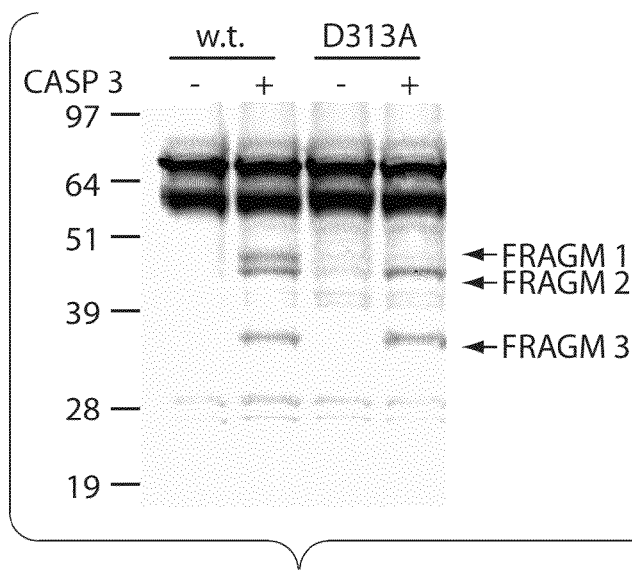
FIG. 6f: Site-directed mutagenesis of D313 to alanine prevents the caspase 3-mediated cleavage of in vitro translated GGA3 (cold) at one of the three major sites (WB with anti-GGA3 Ab).

Given that the anti-GGA3 antibody was raised against amino acids 424-542 and the size of the fragments generated during apoptosis/ischemia, we predict that caspase-mediated cleavage of GGA3 occurs in the hinge domain (FIG. 6e). In support of this, several putative caspase consensus sites, conserved in the GGA3 sequence of several mammals, can be identified in the hinge domain (FIG. 6g). Interestingly, the sequence $^{310}$TLPD$^{313}$ (SEQ ID NO:3) in GGA3 is a caspase site previously identified in the Golgi resident protein, GRASP65 (Lane et al., 2002). Thus, we performed site-directed mutagenesis of D313 to alanine using QuickChange site-directed mutagenesis kit accordingly to manufacturer's instructions (Stratagene). The mutagenesis was confirmed by sequencing. Then, GGA3 wild type (w.t.) and D313A were in vitro translated in the presence of cold methionine and tested in the in vitro caspase 3 cleavage assay as described above. Western Blot analysis with anti-GGA3 Ab revealed that the D313A mutation prevents the generation of the caspase-derived fragment termed Fragm 1 (FIG. 6f). It has been previously shown that the moderate expression of a truncated GGA construct lacking the Hinge and GAE domain (GGA1 VHS+GAT) behaves as a dominant negative (Puertollano et al., 2001b). Thus, our new results showing that GGA3 is cleaved by caspase 3 at D313 would indicate that, during apoptosis, not only is GGA3 removed but the proteolytic products generated in the process may also inhibit the function of the remaining GGA3 molecules. This would be expected to dramatically impair the degradation of BACE, thereby increasing BACE levels and activity, resulting in increased production of Aβ.

Example 4

GGA3 Regulates BACE Protein Levels

Figure 7A:
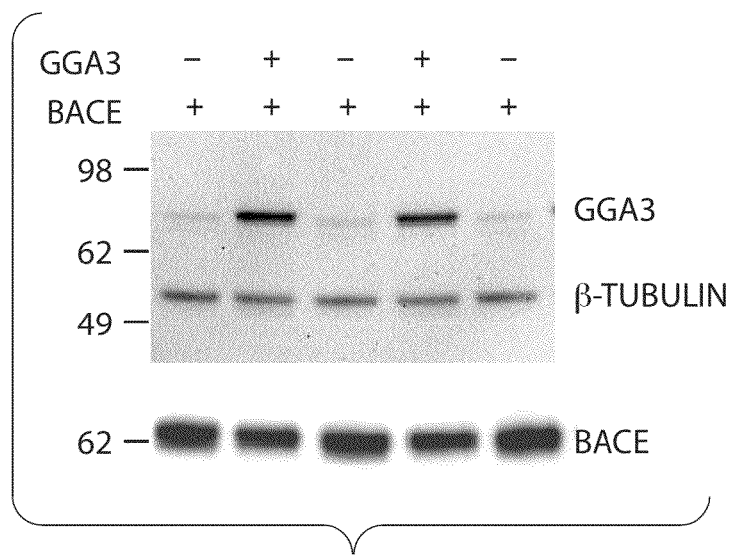
FIG. 7a: Steady state levels of BACE protein were detected in H4 cells overexpressing GGA3 and BACE, or BACE alone.
Figure 7B:
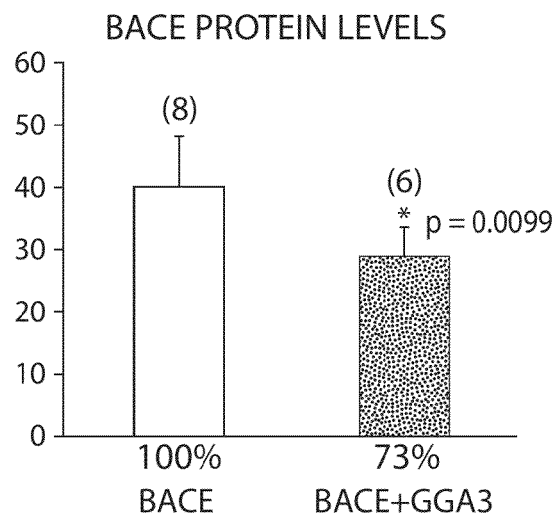
FIG. 7b: The graph represents density values after normalization against β-tubulin. T-test was used for statistical analysis. BACE mRNA levels were measured by real time PCR.
Figure 7C:
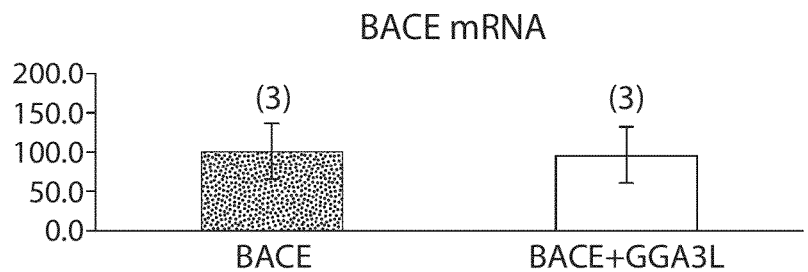
FIG. 7c: The graph represents value after normalization with GAPDH mRNA levels.

To determine whether GGA3 plays a role in BACE degradation we have established H4 cell lines expressing ectopic BACE and GGA3. We have found that the overexpression of GGA3 leads to a significant decrease of steady state levels of BACE protein while BACE mRNA levels remains unchanged in H4 human neuroglioma cells (FIG. 7). Total RNA was extracted using RNeasy Mini Kit (Qiagen). Equal quantities of DNAse-treated RNA samples were subjected to cDNA synthesis using Superscript III Reverse Transcriptase (Invitrogen). Subsequently, SYBR Green Master PCR Mix (Applied Biosystems) and target-specific PCR primers for BACE (5'-ATGGGTGAGGTTACCAACCA-3' (SEQ ID NO:4) and 5'-GACAACGTAGAAGCCCTCCA-3'(SEQ ID NO:5)) and GAPDH (5'-GGTCTCCTCTGACTTCAACA-3' (SEQ ID NO:6) and 5'-GTGAGGGTCTCTCTCTTCCT-3' (SEQ ID NO:7)) were used for amplification of cDNA samples with iCycler real time PCR machine (Bio-Rad). PCR primers were designed to amplify a region flanking two different exons and the target specificity of PCR products were confirmed by sequencing. Standard curve method was used to obtain GAPDH normalized BACE values.

Figure 8:
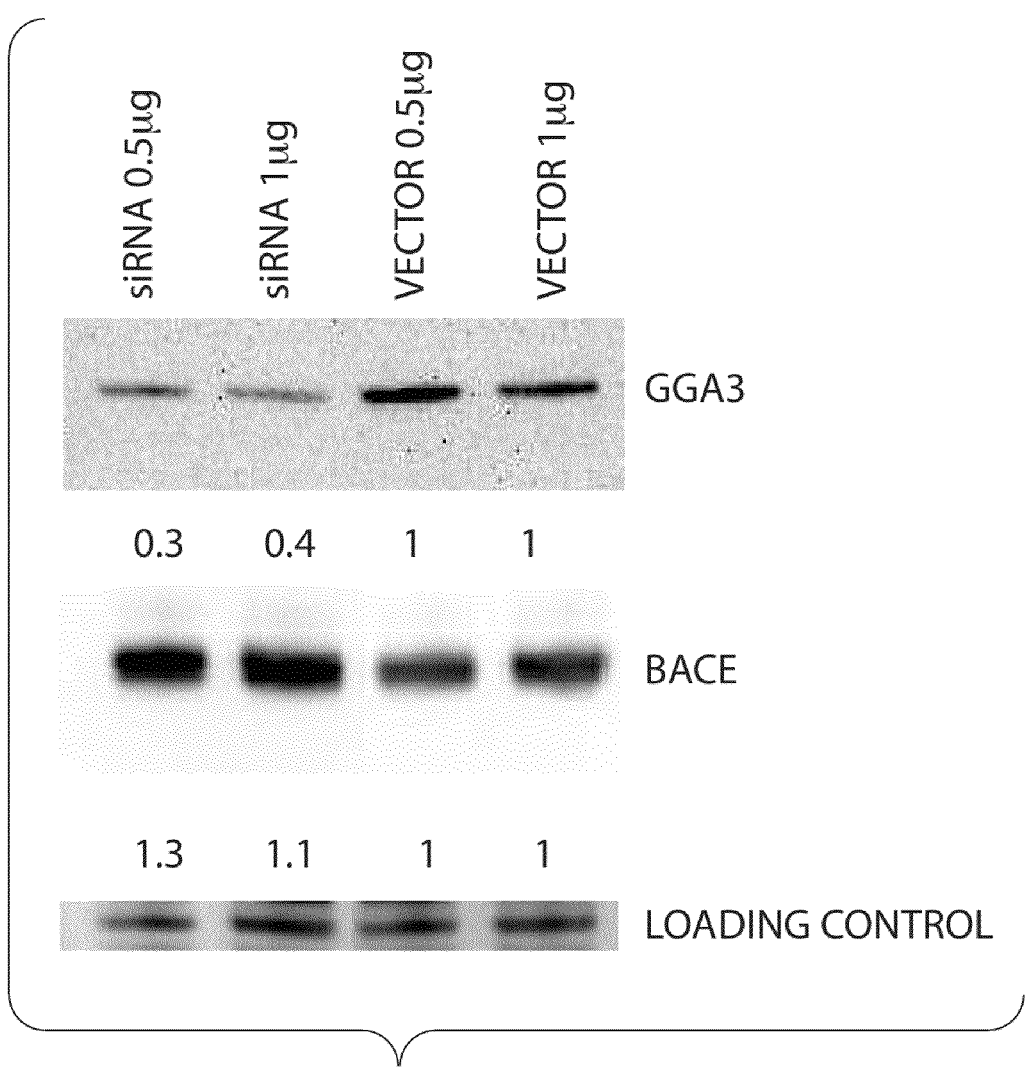
FIG. 8 shows that downregulation of GGA3 increases BACE protein levels. H4-BACE-myc cells were transfected with different concentration of pSuperGGA3 plasmid twice every 72 hr. GGA3 protein levels were measured using Versadoc imager (Bio-Rad) and normalized against a loading control. siRNA reduced GGA3 levels to 30 and 40% of the corresponding controls (transfected with vector alone). BACE protein levels increased 30% in the 0.5 μg samples (normalized against loading control).

We next assessed the effects of GGA3 downregulation on BACE protein levels using plasmid-based RNAi techniques (Brummelkamp et al., 2002; Ghosh et al., 2003). He et al. (2005) have already successfully used this technique to study the effect of GGA1, 2, and 3 on BACE trafficking. The down regulation of endogenous GGA3 was obtained transfecting H4-BACE-myc cells twice (every 72 hr) with different concentration of pSuperGGA3 plasmid (kindly provided by Dr. Kornfeld, Washington University School of Medicine, St. Louis, Mo.). GGA3 protein levels were measured using Versadoc imager (Bio-rad) and normalized against a loading control. Plasmid-mediated siRNA reduced GGA3 levels to 30 and 40% of the corresponding controls (cells transfected with vector alone). BACE protein levels increased by 30% in the cells transfected with 0.5 µg of pSuperGGA3 (normalized against loading control) (FIG. 8). These findings support the hypothesis that GGA3 plays a role in modulating BACE turnover/stability under normal conditions most likely by interfering with BACE lysosomal degradation.

Example 5

Levels of GGA3 Protein are Decreased in AD Brains with Increased Levels of BACE

Our findings are in line with increasing evidence that BACE is a stress-induced protease. BACE levels increase after noxious stimuli, including oxidative stress (Tamagno et al., 2002; Tamagno et al., 2003; Tamagno et al., 2005; Tong et al., 2005), traumatic brain injury (Blasko et al., 2004), ischemia (Wen et al., 2004), impaired energy metabolism (Velliquette et al., 2005) and in AD brains (Fukumoto et al., 2002; Holsinger et al., 2002; Li et al., 2004; Tyler et al., 2002; Yang et al., 2003). The mechanism underlying these increases remains unresolved.

Thus, we have investigated whether decreased GGA3 protein levels may account for increased BACE levels and beta-secretase activity in AD brains. We have analyzed 20 AD and 19 ND (non-demented control) that have already been shown to have increased BACE levels and β-secretase activity (Fukumoto et al., 2002; Holsinger et al., 2002; Li et al., 2004; Tyler et al., 2002; Yang et al., 2003). Western Blot analysis was performed using SECB1 antibody, which recognizes amino acids 296-310 of BACE amino terminus (Fukumoto et al., 2002; Holsinger et al., 2002; Li et al., 2004; Tyler et al., 2002; Yang et al., 2003). GGA3 was detected by anti-GGA3 antibody (BD Tranduction Laboratories). GAPDH was used as loading control (Chemicon). BACE and GGA3 levels were quantified using a Versadoc Imager and QuantityOne software (Biorad). BACE and GGA3 densitometry values were normalized against GAPDH. At least triplicate of each samples were analyzed. The graphs represent mean±SEM of 19 ND and 20 AD. Unpaired t-test and unpaired t-test with Welch correction ware used to perform statistical analysis of BACE and GGA3 levels, respectively.

Figure 9A:
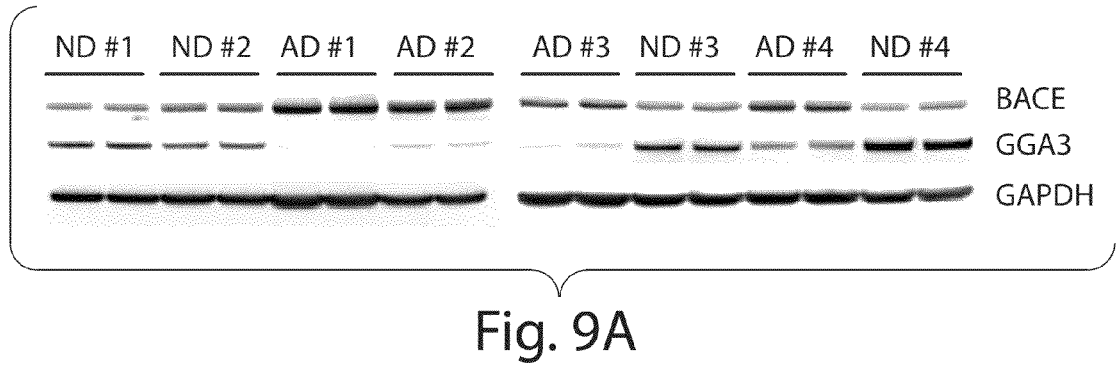
FIGS. 9a,b: BACE protein levels are significantly increased in the AD brains.
Figure 9B:
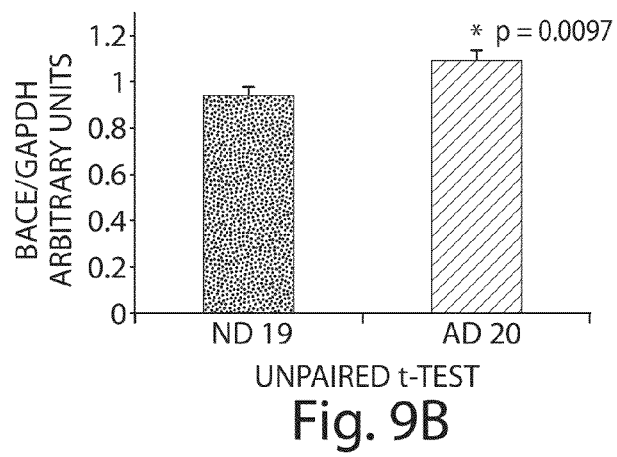
FIG. 9 examines the BACE protein levels in AD patients.
FIGS. 9d,e: the levels of GGA3 are inversely correlated with BACE levels in the AD group but not in the ND group.
FIG. 9f: the decrease in GGA3 protein levels is not due to decreased transcription but most likely occurs at the translational or post-translational level.
FIG. 9g: caspase 3 is activated in the AD but not in ND brains.
Figure 9C:
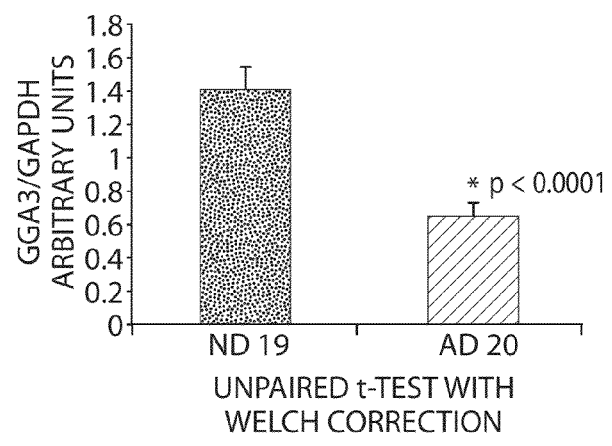
Figure 9D:
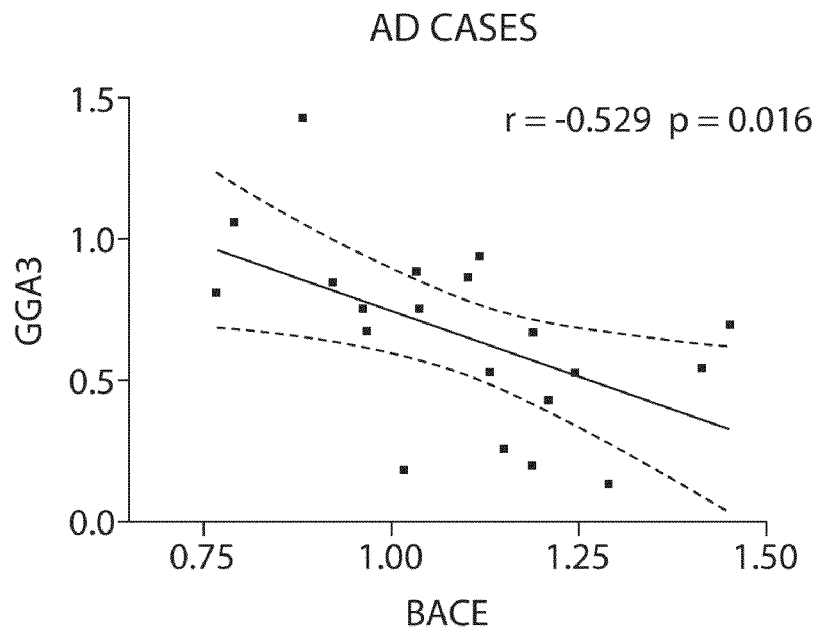
Figure 9E:
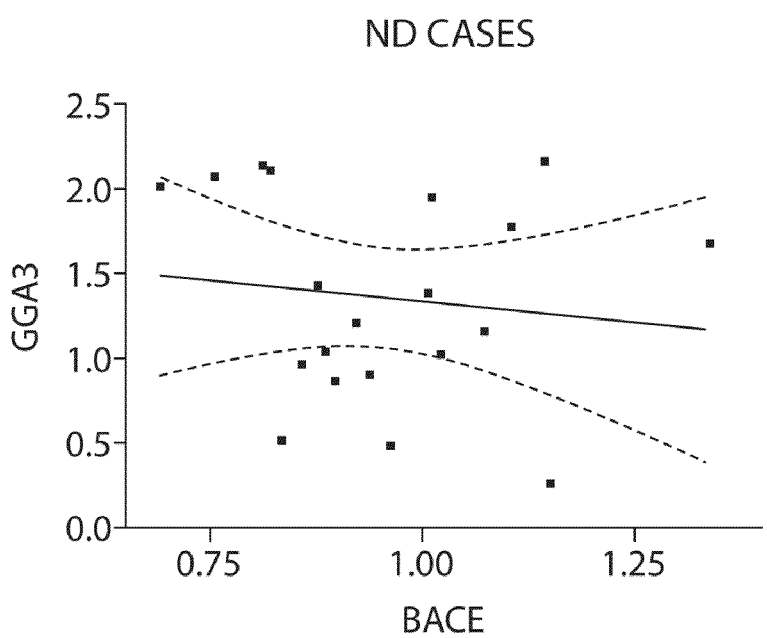
Figure 9F:
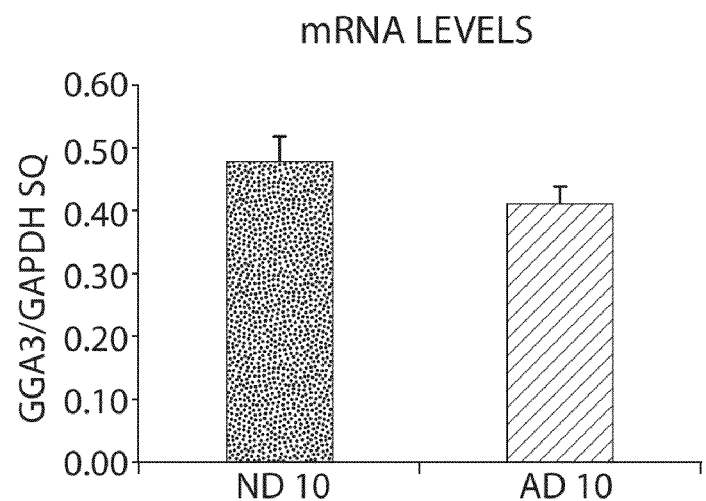
Figure 9G:
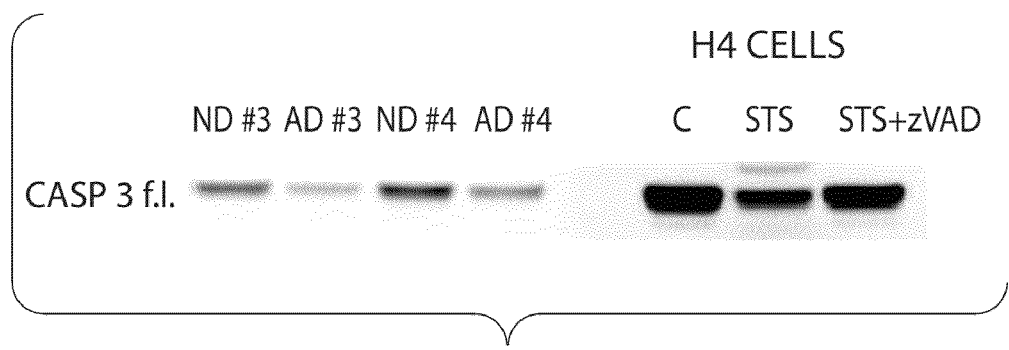

We have confirmed that BACE protein levels are significantly increased in the AD brains (FIG. 9A, B). More importantly, we have found that GGA3 protein levels are significantly decreased in the same AD brains (FIG. 9A, C). Furthermore, the levels of GGA3 are inversely correlated with BACE levels in the AD group but not in the ND group (FIG. 9D, E). Quantification of GGA3 mRNA levels by real-time PCR in 10 AD and 10 ND showed that the decrease in GGA3 protein levels is not due to decreased transcription (FIG. 9F) but most likely occurs at the translational or post-translational level. A possible mechanism of degradation of GGA3 is caspase 3-mediated. Accordingly, we have found that caspase 3 is activated in the AD but not in ND brains as shown by the decrease of caspase 3 full length (f.l.) similar to the one observed in H4 cells treated with staurosporine (STS) (FIG. 9G).

Overall, these new findings provide additional in vivo support for our cell-based experiments showing that GGA3 modulates BACE turnover/stability. Moreover, our studies provide further support for our hypothesis that this process is disturbed in the AD brain leading to increased BACE protein levels. Together with our cell-based studies, these data implicate GGA3 as a key player regulating lysosomal degradation of BACE in its capacity as a chaperone molecule.

REFERENCES

Abe, K., Tanzi, R. E., and Kogure, K. (1991). Selective induction of Kunitz-type protease inhibitor domain-containing amyloid precursor protein mRNA after persistent focal ischemia in rat cerebral cortex. Neurosci Lett 125, 172-174.

Banati, R. B., Gehrmann, J., Wiessner, C., Hossmann, K. A., and Kreutzberg, G. W. (1995). Glial expression of the beta-amyloid precursor protein (APP) in global ischemia. J Cereb Blood Flow Metab 15, 647-654.

Benjannet, S., Elagoz, A., Wickham, L., Mamarbachi, M., Munzer, J. S., Basak, A., Lazure, C., Cromlish, J. A., Sisodia, S., Checker, F., et al. (2001). Post-translational processing of beta-secretase (beta-amyloid-converting enzyme) and its ectodomain shedding. The pro- and transmembrane/cytosolic domains affect its cellular activity and amyloid-beta production. J Biol Chem 276, 10879-10887.

Blasko, I., Beer, R., Bigl, M., Apelt, J., Franz, G., Rudzki, D., Ransmayr, G., Kampfl, A., and Schliebs, R. (2004). Experimental traumatic brain injury in rats stimulates the expression, production and activity of Alzheimer's disease beta-secretase (BACE-1). J Neural Transm 111, 523-536.

Bonfoco, E., Krainc, D., Ankarcrona, M., Nicotera, P., and Lipton, S. A. (1995). Apoptosis and necrosis: two distinct events induced, respectively, by mild and intense insults with N-methyl-D-aspartate or nitric oxide/superoxide in cortical cell cultures. Proc Natl Acad Sci USA 92, 7162-7166.

Bonifacino, J. S., and Traub, L. M. (2003). Signals for sorting of transmembrane proteins to endosomes and lysosomes. Annu Rev Biochem 72, 395-447.

Brancolini, C., Sgorbissa, A., and Schneider, C. (1998). Proteolytic processing of the adherens junctions components beta-catenin and gamma-catenin/plakoglobin during apoptosis. Cell Death Differ 5, 1042-1050.

Brummelkamp, T. R., Bernards, R., and Agami, R. (2002). A system for stable expression of short interfering RNAs in mammalian cells. Science 296, 550-553.

Buxbaum, J. D., Liu, K. N., Luo, Y., Slack, J. L., Stocking, K. L., Peschon, J. J., Johnson, R. S., Castner, B. J., Cerretti, D. P., and Black, R. A. (1998). Evidence that tumor necrosis factor alpha converting enzyme is involved in regulated alpha-secretase cleavage of the Alzheimer amyloid protein precursor. J Biol Chem 273, 27765-27767.

Citron, M. (2004). Beta-secretase inhibition for the treatment of Alzheimer's disease—promise and challenge. Trends Pharmacol Sci 25, 92-97.

Davoli, M. A., Fourtounis, J., Tam, J., Xanthoudakis, S., Nicholson, D., Robertson, G. S., Ng, G. Y., and Xu, D. (2002). Immunohistochemical and biochemical assessment of caspase-3 activation and DNA fragmentation following transient focal ischemia in the rat. Neuroscience 115, 125-136.

De Strooper, B., and Annaert, W. (2000). Proteolytic processing and cell biological functions of the amyloid precursor protein. J Cell Sci 113 (Pt 11), 1857-1870.

Fukumoto, H., Cheung, B. S., Hyman, B. T., and Irizarry, M. C. (2002). Beta-secretase protein and activity are increased in the neocortex in Alzheimer disease. Arch Neurol 59, 1381-1389.

Ghosh, P., Griffith, J., Geuze, H. J., and Kornfeld, S. (2003). Mammalian GGAs act together to sort mannose 6-phosphate receptors. J Cell Biol 163, 755-766.

Haass, C. (2004). Take five-BACE and the gamma-secretase quartet conduct Alzheimer's amyloid beta-peptide generation. Embo J 23, 483-488.

Hara, H., Friedlander, R. M., Gagliardini, V., Ayata, C., Fink, K., Huang, Z., Shimizu-Sasamata, M., Yuan, J., and Moskowitz, M. A. (1997). Inhibition of interleukin 1beta converting enzyme family proteases reduces ischemic and excitotoxic neuronal damage. Proc Natl Acad Sci USA 94, 2007-2012.

He, X., Chang, W. P., Koelsch, G., and Tang, J. (2002). Memapsin 2 (beta-secretase) cytosolic domain binds to the VHS domains of GGA1 and GGA2: implications on the endocytosis mechanism of memapsin 2. FEBS Lett 524, 183-187.

He, X., Zhu, G., Koelsch, G., Rodgers, K. K., Zhang, X. C., and Tang, J. (2003). Biochemical and structural characterization of the interaction of memapsin 2 (beta-secretase) cytosolic domain with the VHS domain of GGA proteins. Biochemistry 42, 12174-12180.

He, X., Li, F., Chang, W. P., and Tang, J. (2005) GGA proteins mediate the recycling pathway of memapsin 2 (BACE). J Biol. Chem. 280, 11696-11703.

Holsinger, R. M., McLean, C. A., Beyreuther, K., Masters, C. L., and Evin, G. (2002). Increased expression of the amyloid precursor beta-secretase in Alzheimer's disease. Ann Neurol 51, 783-786.

Huse, J. T., Pijak, D. S., Leslie, G. J., Lee, V. M., and Doms, R. W. (2000). Maturation and endosomal targeting of beta-site amyloid precursor protein-cleaving enzyme. The Alzheimer's disease beta-secretase. J Biol Chem 275, 33729-33737.

Hussain, I., Hawkins, J., Shikotra, A., Riddell, D. R., Faller, A., and Dingwall, C. (2003). Characterization of the ectodomain shedding of the beta-site amyloid precursor protein-cleaving enzyme 1 (BACE1). J Biol Chem 278, 36264-36268.

Kalaria, R. N., Bhatti, S. U., Palatinsky, E. A., Pennington, D. H., Shelton, E. R., Chan, H. W., Perry, G., and Lust, W. D. (1993). Accumulation of the beta amyloid precursor protein at sites of ischemic injury in rat brain. Neuroreport 4, 211-214.

Kim, H. S., Lee, S. H., Kim, S. S., Kim, Y. K., Jeong, S. J., Ma, J., Han, D. H., Cho, B. K., and Suh, Y. H. (1998). Post-ischemic changes in the expression of Alzheimer's APP isoforms in rat cerebral cortex. Neuroreport 9, 533-537.

Koistinaho, J., Pyykonen, I., Keinanen, R., and Hokfelt, T. (1996). Expression of beta-amyloid precursor protein mRNAs following transient focal ischaemia. Neuroreport 7, 2727-2731.

Lammich, S., Kojro, E., Postina, R., Gilbert, S., Pfeiffer, R., Jasionowski, M., Haass, C., and Fahrenholz, F. (1999). Constitutive and regulated alpha-secretase cleavage of Alzheimer's amyloid precursor protein by a disintegrin metalloprotease. Proceedings of the National Academy of Sciences of the United States of America 96, 3922-3927.

Lane, J. D., Lucocq, J., Pryde, J., Barr, F. A., Woodman, P. G., Allan, V. J., and Lowe, M. (2002). Caspase-mediated cleavage of the stacking protein GRASP65 is required for Golgi fragmentation during apoptosis. J Cell Biol 156, 495-509.

Li, R., Lindholm, K., Yang, L. B., Yue, X., Citron, M., Yan, R., Beach, T., Sue, L., Sabbagh, M., Cai, H., et al. (2004). Amyloid beta peptide load is correlated with increased beta-secretase activity in sporadic Alzheimer's disease patients. Proc Natl Acad Sci USA 101, 3632-3637.

Liu, R., Yang, S. H., Perez, E., Yi, K. D., Wu, S. S., Eberst, K., Prokai, L., Prokai-Tatrai, K., Cai, Z. Y., Covey, D. F., et al. (2002). Neuroprotective effects of a novel non-receptorbinding estrogen analogue: in vitro and in vivo analysis. Stroke 33, 2485-2491.

Namura, S., Zhu, J., Fink, K., Endres, M., Srinivasan, A., Tomaselli, K. J., Yuan, J., and Moskowitz, M. A. (1998). Activation and cleavage of caspase-3 in apoptosis induced by experimental cerebral ischemia. J Neurosci 18, 3659-3668.

Pastorino, L., Ikin, A. F., Nairn, A. C., Pursnani, A., and Buxbaum, J. D. (2002). The carboxyl-terminus of BACE contains a sorting signal that regulates BACE trafficking but not the formation of total A(beta). Mol Cell Neurosci 19, 175-185.

Puertollano, R., Aguilar, R. C., Gorshkova, I., Crouch, R. J., and Bonifacino, J. S. (2001a). Sorting of mannose 6-phosphate receptors mediated by the GGAs. Science 292, 1712-1716.

Puertollano, R., and Bonifacino, J. S. (2004). Interactions of GGA3 with the ubiquitin sorting machinery. Nat Cell Biol 6, 244-251.

Puertollano, R., Randazzo, P. A., Presley, J. F., Hartnell, L. M., and Bonifacino, J. S. (2001b). The GGAs promote ARF-dependent recruitment of clathrin to the TGN. Cell 105, 93-102.

Shi, J., Yang, S. H., Stubley, L., Day, A. L., and Simpkins, J. W. (2000). Hypoperfusion induces overexpression of beta-amyloid precursor protein mRNA in a focal ischemic rodent model. Brain Res 853, 1-4.

Sinha, S., Anderson, J. P., Barbour, R., Basi, G. S., Caccavello, R., Davis, D., Doan, M., Dovey, H. F., Frigon, N., Hong, J., et al. (1999). Purification and cloning of amyloid precursor protein beta-secretase from human brain. Nature 402, 537-540.

Stephenson, D. T., Rash, K., and Clemens, J. A. (1992). Amyloid precursor protein accumulates in regions of neurodegeneration following focal cerebral ischemia in the rat. Brain Res 593, 128-135.

Tamagno, E., Bardini, P., Obbili, A., Vitali, A., Borghi, R., Zaccheo, D., Pronzato, M. A., Danni, O., Smith, M. A., Perry, G., and Tabaton, M. (2002). Oxidative stress increases expression and activity of BACE in NT2 neurons. Neurobiol Dis 10, 279-288.

Tamagno, E., Guglielmotto, M., Bardini, P., Santoro, G., Davit, A., Di Simone, D., Danni, O., and Tabaton, M. (2003). Dehydroepiandrosterone reduces expression and activity of BACE in NT2 neurons exposed to oxidative stress. Neurobiol Dis 14, 291-301.

Tamagno, E., Parola, M., Bardini, P., Piccini, A., Borghi, R., Guglielmotto, M., Santoro, G., Davit, A., Danni, O., Smith, M. A., et al. (2005). Beta-site APP cleaving enzyme up-regulation induced by 4-hydroxynonenal is mediated by stress-activated protein kinases pathways. J Neurochem 92, 628-636.

Tong, Y., Zhou, W., Fung, V., Christensen, M. A., Qing, H., Sun, X., and Song, W. (2005). Oxidative stress potentiates BACE1 gene expression and Abeta generation. J Neural Transm 112, 455-469.

Tyler, S. J., Dawbarn, D., Wilcock, G. K., and Allen, S. J. (2002). alpha- and beta-secretase: profound changes in Alzheimer's disease. Biochem Biophys Res Commun 299, 373-376.

Vassar, R., Bennett, B. D., Babu-Khan, S., Kahn, S., Mendiaz, E. A., Denis, P., Teplow, D. B., Ross, S., Amarante, P., Loeloff, R., et al. (1999). Beta-secretase cleavage of Alzheimer's amyloid precursor protein by the transmembrane aspartic protease BACE. Science 286, 735-741.

Velliquette, R. A., O'Connor, T., and Vassar, R. (2005). Energy inhibition elevates beta-secretase levels and activity and is potentially amyloidogenic in APP transgenic mice: possible early events in Alzheimer's disease pathogenesis. J Neurosci 25, 10874-10883.

Wakita, H., Tomimoto, H., Akiguchi, I., Ohnishi, K., Nakamura, S., and Kimura, J. (1992). Regional accumulation of amyloid beta/A4 protein precursor in the gerbil brain following transient cerebral ischemia. Neurosci Lett 146, 135-138.

Wen, Y., Onyewuchi, O., Yang, S., Liu, R., and Simpkins, J. W. (2004). Increased beta-secretase activity and expression in rats following transient cerebral ischemia. Brain Res 1009, 1-8.

Yang, L. B., Lindholm, K., Yan, R., Citron, M., Xia, W., Yang, X. L., Beach, T., Sue, L., Wong, P., Price, D., et al. (2003). Elevated beta-secretase expression and enzymatic activity detected in sporadic Alzheimer disease. Nat Med 9, 3-4.

Example 6

Depletion of GGA3 Stabilizes BACE and Enhances β-Secretase Activity

A key neuropathological event in Alzheimer's disease (AD) is the cerebral accumulation of an ~4 kDa peptide termed Aβ, the principle component of senile plaques. The Aβ peptide is derived by serial proteolysis of APP by β-secretase at the N-terminus followed by γ-secretase at the C-terminus (De Strooper and Annaert, 2000). β-secretase has been identified as a novel membrane-tethered member of the aspartyl proteases, termed BACE (Sinha et al., 1999; Vassar et al., 1999). BACE is an N-glycosylated type 1 transmembrane protein that undergoes constitutive N-terminal processing in the Golgi apparatus. The ectodomain contains four glycosylation sites and two signature sequences typically associated with aspartyl proteases (DT/SGT/S). BACE is targeted through the secretory pathway to the plasma membrane where it can be internalized to endosomes (Citron, 2004). The BACE-C-terminal fragment (CTF) contains a specific di-leucine (DXXLL) sorting signal that is present in several transmembrane proteins (e.g. cation-dependent and cation-independent mannose-6-phosphate receptor, CD- and CI-MRP) and that regulates endocytosis and ultimately lysosomal degradation (Bonifacino and Traub, 2003). Mutagenesis of LL to AA results in retention of BACE at the plasma membrane (Huse et al., 2000; Pastorino et al., 2002). Furthermore, the di-leucine motif may play a role in BACE degradation since BACE LL/AA mutations increase protein levels of BACE (Pastorino et al., 2002). More recently, we reported that BACE is normally degraded in lysosomes, and that mutagenesis of the di-leucine motif in the BACE CTF prevents accumulation of BACE in the lysosomes following inhibition of lysosomal hydrolases (Koh et al., 2005). The BACE acidic di-leucine motif has been shown to bind GGA1, 2, and 3 (Golgi-localized γ-ear-containing ARF binding proteins) and phosphorylation of BACE-S498 appears to increase their binding (He et al., 2002; He et al., 2003; Shiba et al., 2004; von Arnim et al., 2004; Wahle et al., 2005). GGA1, 2, and 3 are monomeric adaptors that are recruited to the trans-Golgi network by the Arf1-GTPase. They consist of four distinct segments: a VHS (VPS27, Hrs, and STAM) domain that binds the acidic di-leucine sorting signal, DXXLL; a GAT (GGA and Tom1) domain which binds Arf: GTP; a hinge region which recruits clathrin; and a GAE (gamma-adaptin ear homology) domain which exhibits sequence similarity to the ear region of γ-adaptin and recruits a number of accessory proteins. GGAs are necessary for the sorting of acid hydrolases to the lysosomes. Newly synthesized acid hydrolases modified with mannose 6-phosphate groups bind to mannose 6-phosphate receptors (MPRs). MPRs bind to the VHS domain of GGAs via the DXXLL motif (Bonifacino, 2004). GGAs are likely involved in the transport from the Golgi complex to the endosome of proteins containing the DXXLL signal. However, Puertollano et al. (Puertollano and Bonifacino, 2004) have recently reported that the GGA3 GAT domain binds ubiquitin, and that ubiquinated GGA3 is necessary for the delivery of activated epithelial growth factor receptor (EGFR) to lysosomes. RNAi silencing of GGA3, but not GGA1 or GGA2, resulted in the accumulation of EGFRs in enlarged early endosomes and partially blocked their delivery to lysosomes where they are normally degraded. These findings indicate that GGAs may be involved in the delivery of endosomal cargoes to lysosomes. Recently, it has also been shown (He et al., 2005) that RNAi silencing of GGA1, 2, and, 3 significantly increases the levels of BACE in endosomes.

Increasing evidence suggest that BACE is a stress-induced protease. BACE levels increase in cells exposed to oxidative stress (Tamagno et al., 2002; Tamagno et al., 2003; Tamagno et al., 2005; Tong et al., 2005), in in vivo animal models following traumatic brain injury (TBI) (Blasko et al., 2004), cerebral ischemia (Wen et al., 2004) and impaired energy metabolism (Velliquette et al., 2005), and in AD brains (Fukumoto et al., 2002; Holsinger et al., 2002; Li et al., 2004a; Tyler et al., 2002; Yang et al., 2003). The mechanisms underlying such increases remain unknown. In the current study, we report that BACE protein levels and consequently, β-secretase cleavage of APP, are potentiated during apoptosis. In exploring the mechanism underlying this novel apoptotic event, we found that the elevation in BACE following caspase activation is due to post-translational stabilization owing to a significant impairment in the degradation and turnover of BACE. Given our previous findings that BACE is normally degraded in the lysosomes and since the C-terminal di-leucine motif is required for trafficking to lysosomes, we next investigated the fate of GGA3 during apoptosis. We discovered that GGA3 is a novel caspase 3 substrate that is cleaved during apoptosis. This was shown both in vitro, in cell cultures, and in vivo, in a rat model of cerebral ischemia. Moreover, we observed that as GGA3 is removed by caspase cleavage, BACE is stabilized leading to elevated β-secretase cleavage of APP. In further support of our hypothesis that GGA3 plays a key role in BACE degradation, we show that RNAi silencing of GGA3 increases levels of BACE, APP-C99, and Aβ. Finally, to begin to investigate whether decreased GGA3 protein levels may account for increased BACE levels and β-secretase activity in AD brains (Fukumoto et al., 2002; Holsinger et al., 2002; Li et al., 2004a; Tyler et al., 2002; Yang et al., 2003), we measured levels of BACE and GGA3 in a series of AD and non-demented (ND) control brain samples. While BACE protein levels were significantly increased in the AD temporal cortex, in contrast, GGA3 protein levels were significantly decreased and were inversely correlated with BACE levels in the AD group, but not in the ND control group. These data suggest that depletion of GGA3 is responsible for enhanced BACE levels and β-secretase activity during ischemia and in AD brain.

Results

Caspase Activation Increases BACE and APP-C99 Levels

Figure 10A:
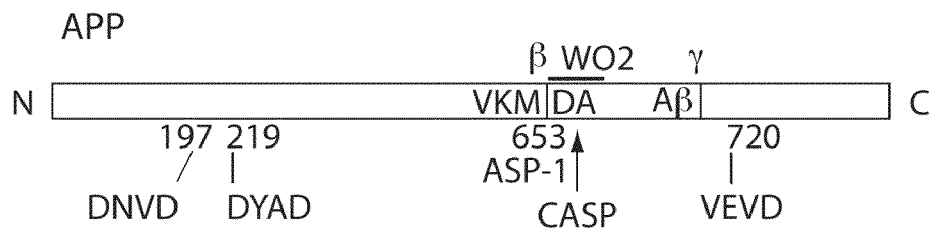
FIG. 10: Caspase Activation Increases BACE and APP-C99 Levels.
A: Schematic representation of APP caspase sites, and antibody recognition sites.
B: Apoptosis was induced in human H4 neuroglioma cells expressing APP751 by STS treatment. Western blot analysis performed with WO2 antibody revealed APP-C99 and APP-C99ΔC31 during time-course experiments. Western blot analysis with anti-caspase 3 active fragment antibody showed caspase 3 activation as early as 6 hr during STS treatment. Limited caspase activity and a small increase of APP-C99 in the untreated cells at time point 12 (horizontally compressed band) and 24 hr was also detected in the control sample owing to the fact that the control cells were grown in serum-free media. C: WB analysis with an antibody, ASP-1 (Oncogene), that recognizes only the first aspartyl residue of Aβ region confirmed that the 12 kDa APP fragment increasing following caspase activation is APP-C99 in the cells H4-APP751, and also in human SH-SY5Y and murine N2A cells expressing only endogenous APP. D-E: Western blot analysis with anti-BACE antibody revealed increased BACE protein levels following apoptosis induced by STS or etoposide treatment, respectively. Cu,Zn—SOD or β-tubulin were used as a loading control. Densitometry analysis was performed using NIH image software. The graphs represent BACE levels expressed as percentage increase versus BACE levels in control cells (100%). Each bar represents the mean±SEM of at least three experiments.
Figure 10B:
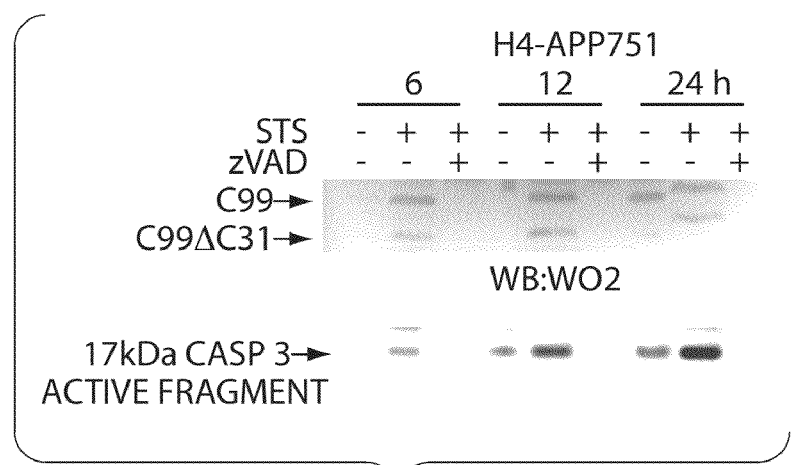

Apoptosis has been shown to enhance Aβ levels in neuronal and non-neuronal cells (Barnes et al., 1998; Galli et al., 1998; Gervais et al., 1999; Guo et al., 2001; LeBlanc, 1995; Sodhi et al., 2004; Tesco et al., 2003). Gervais and colleagues (Gervais et al., 1999) proposed that caspase-mediated cleavage of APP at APPD720 was responsible for increased Aβ generation associated with apoptosis. We subsequently showed that increased levels of Aβ following induction of apoptosis in CHO cells, did not require caspase-mediated cleavage of APP at either its C-terminal (D720) and/or N-terminal caspase sites (Tesco et al., 2003) (FIG. 1A). In that same study we reported that 6 hr treatment with STS significantly increased Aβ1-total production compared to untreated cells. The Aβ ELISA measured Aβ1-total using biotinylated 3D6, which specifically recognizes the aspartate in position 1 of Aβ, as a reporter antibody. The ELISA data demonstrated that the increase in Aβ following caspase activation is exclusively due to β-secretase cleavage at position 1 and does not involve other Aβ species starting at other residues (e.g. at position 2 as expected from a caspase cleavage in the β-secretase region). Here, we investigated whether apoptosis-mediated increases in Aβ levels may be due to enhanced cleavage of APP by BACE, the protease responsible for β-secretase cleavage of APP (Vassar et al., 1999). For this purpose, we tested whether apoptosis/caspase activation leads to increased levels of APP-C99, the C-terminal fragment generated by β-secretase cleavage of APP. Western blot (WB) analysis with the antibody WO2, (raised against amino acids 1-17 of Aβ region), revealed that apoptosis induced by staurosporine (STS) resulted in increased levels of C99 in H4 human neuroglioma cell lines expressing APP751 (H4-APP751) (FIG. 10B). Western blot analysis with an antibody recognizing the caspase 3 active fragment showed that caspase 3 activation occurs as early as 6 hr following treatment with STS. It should be noted that we also observed a small increase of APP-C99 and activated caspase fragment in untreated cells after 12 and 24 hr, most likely due to marginal caspase activity triggered by serum deprivation, which is known to activate caspases in cells of neuronal origin. The loading control for caspase 3 and WO2 blots is the same as that shown in FIG. 10D.

Figure 10C:
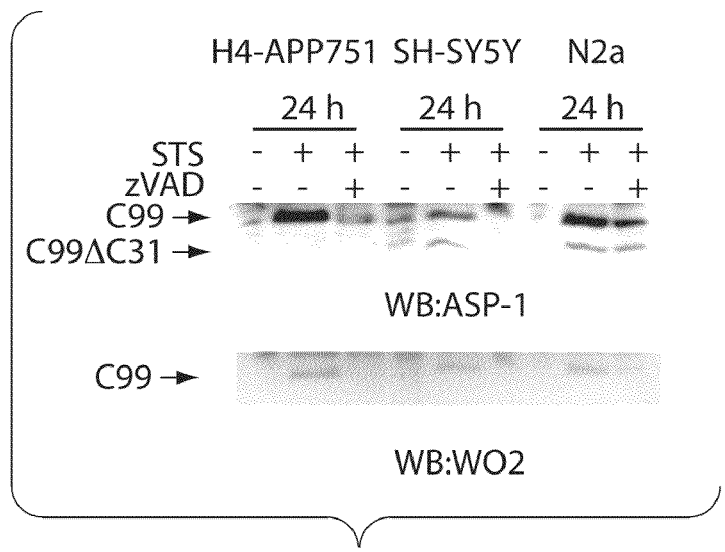

A 6.5 kDa fragment corresponding to caspase cleavage at D720 (APP-C99ΔC31) was also detected in apoptotic H4-APP751 as previously described (Tesco et al., 2003). These data agree with those of LeBlanc and colleagues (LeBlanc et al., 1999) who reported that the generation of a 6.5 kDa fragment precedes the increased production of both secreted and intracellular Aβ in apoptotic neurons. However, LeBlanc et al. (1999) proposed that the 6.5 kDa fragment was generated by caspase-mediated cleavage at D653 (FIG. 10A). A caspase 6-like site (VKMD) has been identified at D653 in the β-secretase region of APP (Gervais et al., 1999; LeBlanc et al., 1999) and it has been reported that the APP Swedish mutation KM/NL improves the likelihood that caspase 6 can cleave at this site (Gervais et al., 1999). Caspase cleavage between D653 and A654 is expected to generate a novel APP-CTF that could be termed C98 starting with A654. In contrast, β-secretase generates APP-C99 starting with D653. Western Blot analysis with an antibody, ASP-1 (Oncogene), that recognizes only the first aspartyl residue of Aβ region confirmed that the 12 kDa APP fragment increasing following caspase activation is APP-C99. This was shown to be the case in the cells H4-APP751, and also in human SH-SY5Y and murine N2A cells expressing only endogenous APP (FIG. 10C).

Figure 10D:
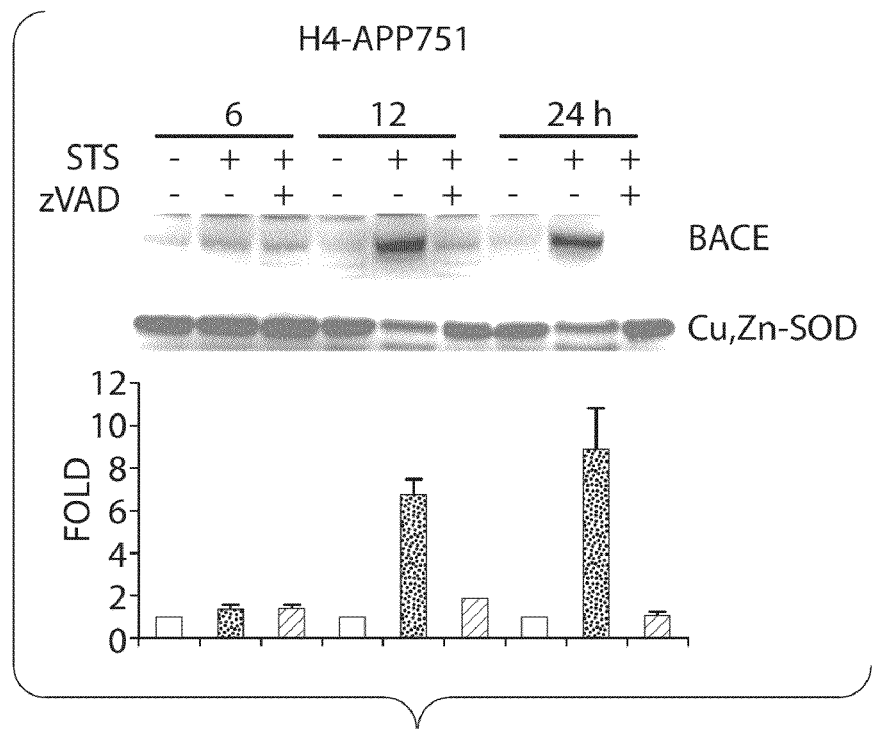
Figure 10E:
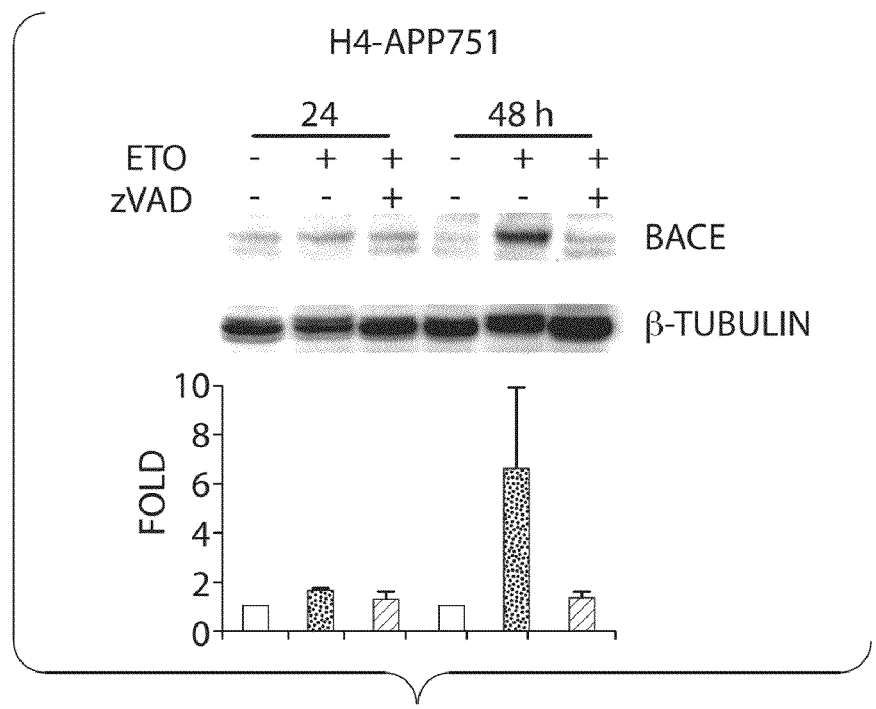

We next asked whether the increased levels of APP-C99 was due to increased levels of endogenous BACE in the H4-APP751 cells. We found that BACE protein levels were increased ~6-fold and ~9 fold after 12 or 24 hr of STS treatment, respectively (FIG. 10D). Next, to confirm that increased BACE protein levels were the result of caspase activation, we used a different apoptotic inducer, etoposide. Apoptosis induced by etoposide also increased BACE protein levels, albeit with a different time course (FIG. 10E). Inhibition of caspase activity by zVAD prevented BACE accumulation in both treatments (FIG. 10D-E). As a control for protein loading, the same blots were reprobed with anti-Cu, Zn—SOD and anti-β-tubulin antibodies, respectively. We chose to use unrelated proteins for which sensitive antibodies were available (and worked best), as loading controls, for each set of experiments. The use of two different loading controls serves to confirm our findings. Using the anti-BACE antibody currently available, detection of steady state levels of BACE is not as robust as detection of steady state levels of APP-C99. Thus, the apparent discrepancy between the increase in C99 levels at 6 hr and absence of increase of BACE levels is most likely due to the difference in the sensitivity of the antibodies used for detection of BACE versus APP-C99. However, we cannot rule out the possibility that generation of the C99 fragment earlier (6 hr) in the STS model is BACE-independent, but caspase-dependent. These findings were also confirmed in CHO cells expressing BACE and APP 751 and in primary neuronal cultures obtained from E15 embryos of transgenic mice expressing human APP with the "Swedish" mutation (KM670/671NL) (SWE) (data not shown). These results indicate that caspase activation increases protein levels of BACE and potentiates β-secretase-mediated processing of APP in neuronal and non-neuronal cell cultures.

Caspase Activation Increases the Half-Life of BACE

Figure 11A:
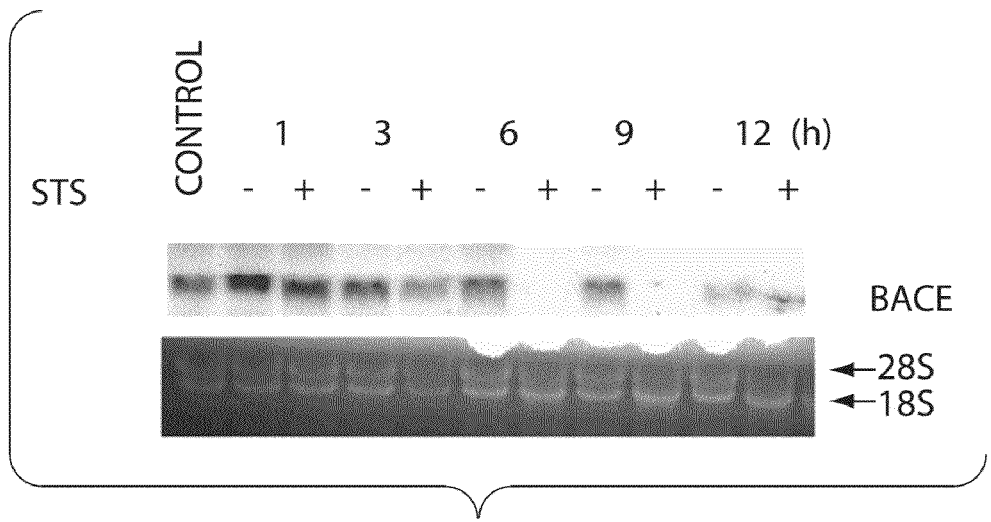
FIG. 11: Caspase Activation Increases the Half-Life of BACE.
A: Northern Blot analysis: H4-APP751 cells were treated with STS during time course experiments. Total RNA was extracted, and 20 μg of the resulting RNA were analyzed by northern blotting with BACE cDNA. Ethidium staining of the gel (lower panel) confirmed equal RNA loading and absence of non-specific degradation. B: Pulse-chase analysis. H4-APP751 cells were transiently transfected with BACE-Myc cDNA and were metabolically labeled after 24 hr. Lysates from each time point were immunoprecipitated with anti-Myc antibody. C: Protein amounts were quantified by phosphorimager and represented in the graph. The mean±SEM of at least three experiments is shown. D-E-F: For the TACE and APP pulse-chase, H4-APP751 cells were metabolically labeled. Lysates from each time point were immunoprecipitated wither with anti-TACE or anti-APP (A8717) antibody. Protein amounts were quantified by phosphorimager and represented in the graph. The mean±SEM of at least three experiments is shown. D: Cycloheximide degradation time-course: BACE, TACE, and APP proteins were detected by Western blot at various times after addition of CHX (40 μg/ml) only or STS+CHX in H4-APP751 cells. The degradation of BACE was decreased while the degradation of TACE and APP was unchanged during the apoptosis.

We next asked whether apoptosis increases protein levels of BACE via increased gene expression. BACE mRNA levels were not increased, but were virtually undetectable after only 6 hr of STS treatment in the H4-APP751 cells (FIG. 11A). The preservation of 28S and 18S ribosomal RNA ruled out non-specific RNA degradation (FIG. 11A). This led us to ask whether BACE protein levels were increased during apoptosis due to decreased degradation.

Figure 11B:
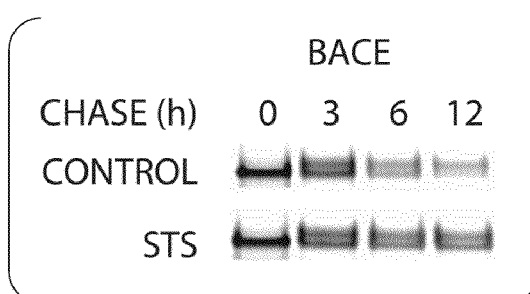
Figure 11C:
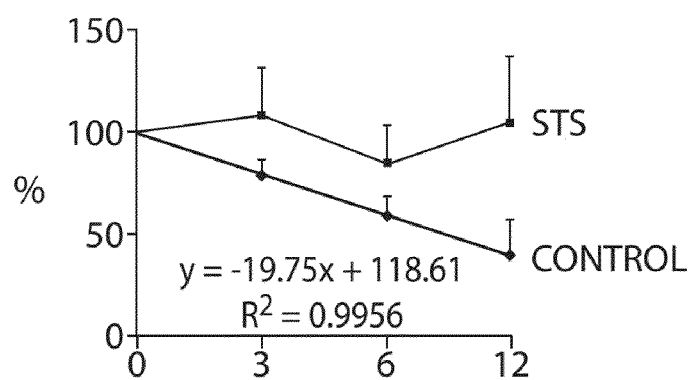
Figure 11D:
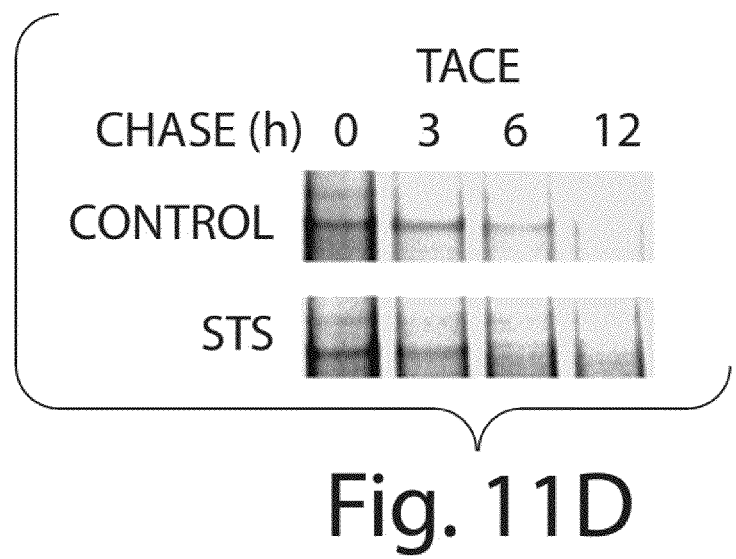
Figure 11E:
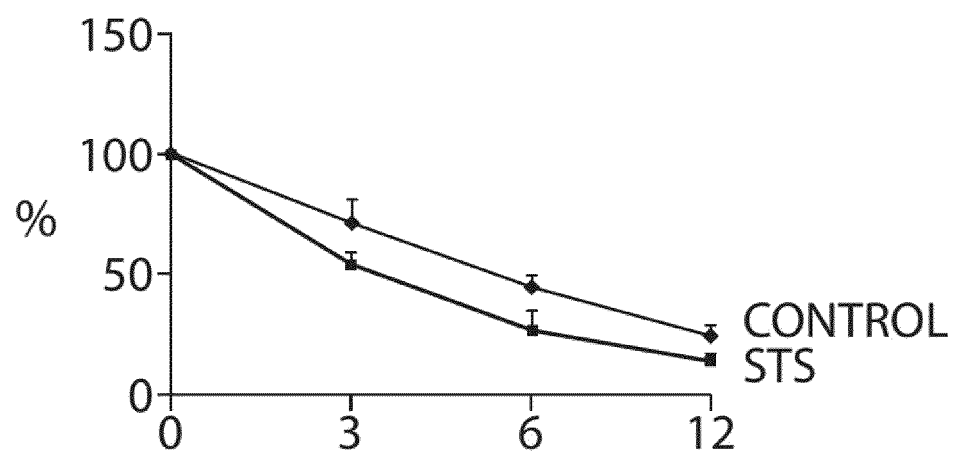
Figure 11F:
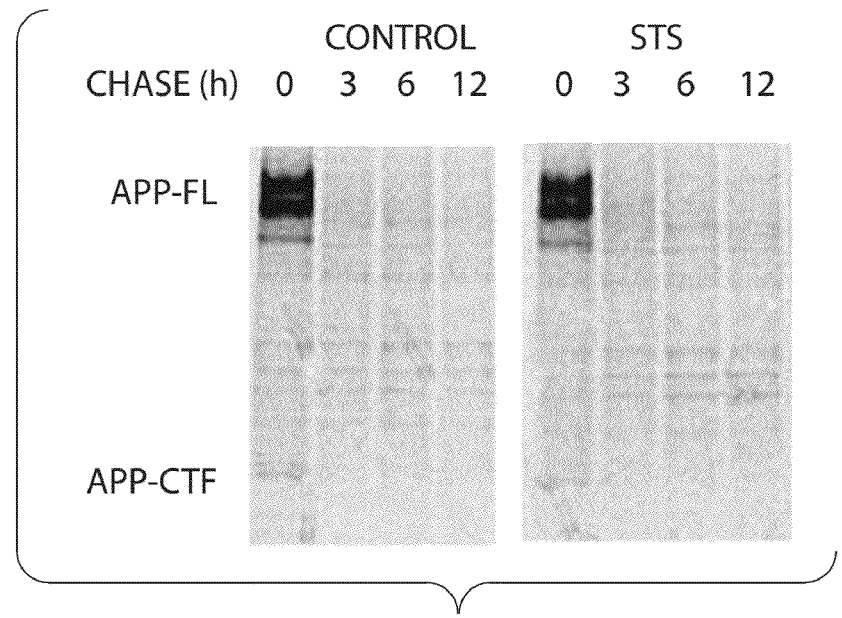
Figure 11G:
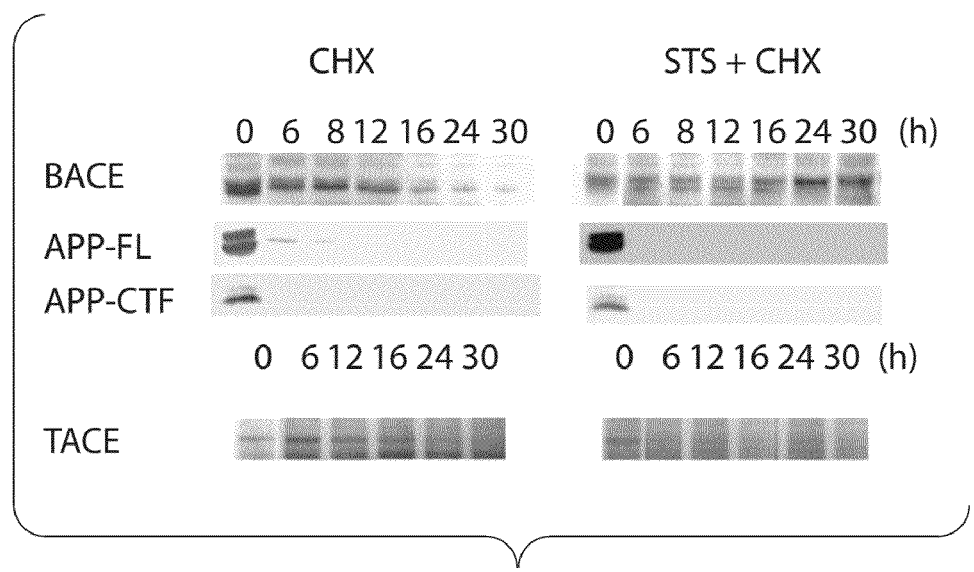

Pulse-chase analyses revealed that the approximate half-life of BACE was ~9 hr under normal conditions. However, following caspase activation, BACE levels did not significantly decrease (FIG. 11B-C). In contrast, the half-lives of tumor necrosis factor-alpha (TNF) converting enzyme (TACE) (FIG. 11D-E) and full-length APP (and APP-CTFs) (FIG. 2F) were not increased during apoptosis. In confirmation of these findings, the approximate half-life of endogenous BACE was roughly 10 hr under normal conditions in cycloheximide (CHX) time course experiments. However, following caspase activation, BACE levels did not significantly decrease even after 30 hr into the time-course. Given that BACE is stabilized during apoptosis, while many other proteins are degraded at normal or accelerated rates (e.g., APP and TACE), the apparent increase of BACE protein levels at the latest time points of the CHX+STS time course was most likely due to a relative increase of stabilized BACE when normalized for equal amounts of total protein. The half-life of the negative control, TACE, and APP were somewhat decreased during apoptosis (FIG. 11G). A possible explanation for the apparent discrepancy between BACE half-life (9-10 hr) and a 6 fold increase in BACE protein levels after 12 hr treatment with STS is that BACE levels in these studies are relative to total protein during the apoptotic time-course. As measured, BACE levels are determined relative to equal amounts of total protein loaded throughout the time course. Thus, absolute BACE levels are not increasing during apoptosis, BACE levels are only increasing as a percentage of total cellular protein. Since BACE is being stabilized during apoptosis, while many other proteins are succumbing to caspase cleavage, e.g. SOD and GGA3, BACE levels remain fairly constant in the cell during apoptosis due to a significantly longer half-life. This translates into the detection of increased levels of BACE/total cell protein during the apoptosis time course.

The BACE Trafficking Molecule GGA3 is Cleaved by Caspase 3 During Apoptosis

We have previously reported that endogenous BACE is normally degraded by lysosomal hydrolases (Koh et al., 2005). Thus, we hypothesized that caspase activation leads to BACE stabilization by interfering with its degradation in the lysosomes. We previously reported that the BACE di-leucine motif, the binding site for GGAs, plays a role in targeting BACE to the lysosomes (Koh et al., 2005). Since GGA3 has been shown to be necessary for lysosomal degradation of EGFR (Puertollano and Bonifacino, 2004), we hypothesized that GGA3 may play a role in the sorting of BACE to the lysosomes and that caspase cleavage of GGA3 during apoptosis may impair the degradation of BACE.

Figure 12A:
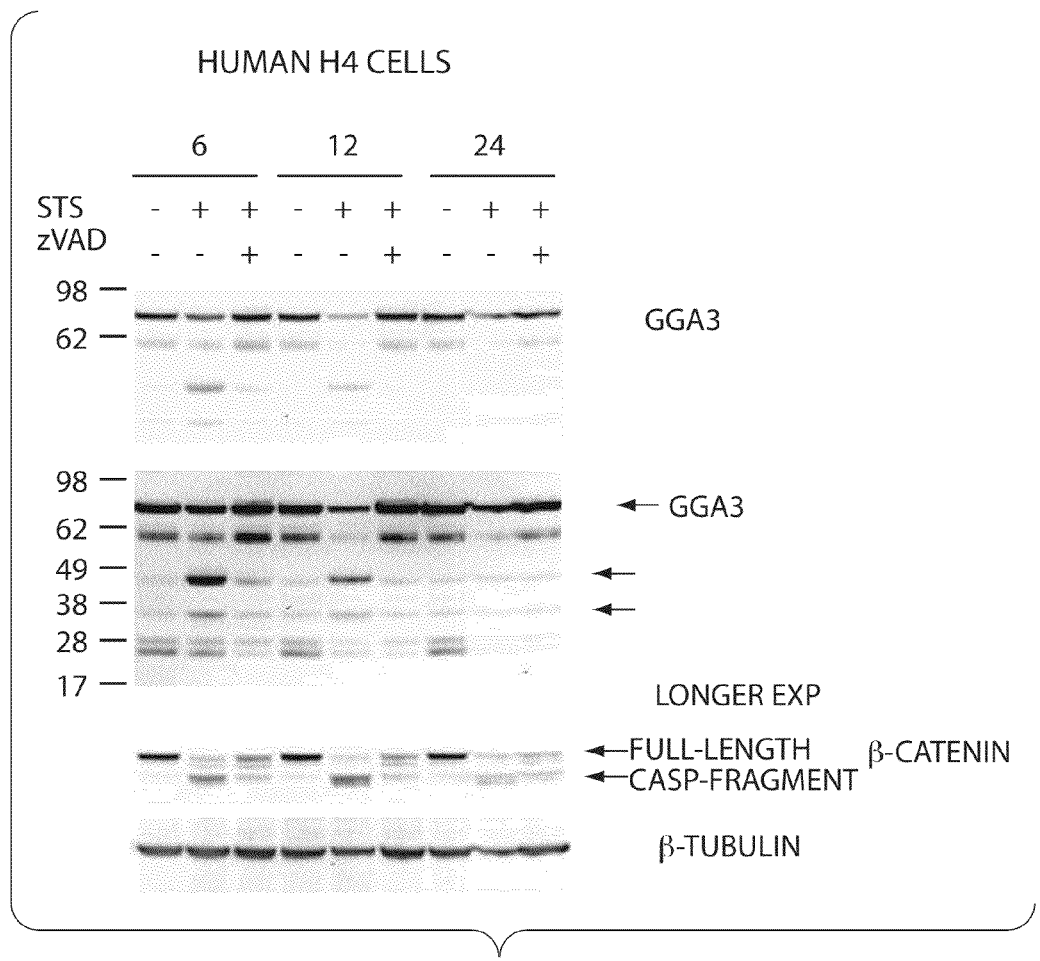
FIG. 12: The BACE Trafficking Molecule GGA3 Is Cleaved by Caspase-3 during Apoptosis.
A: Apoptosis was induced in H4-APP751 cells by STS treatment during time course experiments. Western blot analysis with an anti-GGA3 antibody revealed cleavage of GGA3 in two major fragments of ~48 and ~37 kDa (indicated by the arrows) in apoptotic H4 cells, which was prevented by caspase inhibition (zVAD). A longer exposure (Long exp) better evidentiates the caspase-derived fragments. Western Blot analysis with anti-β-catenin antibody revealed that β-catenin was cleaved by caspase (casp-fragment) in the H4-APP751 cells with a temporal pattern similar to that observed for GGA3. B: recombinant caspase 3 cleaves in vitro translated GGA3 (labeled with [$^{35}$S] methionine) in several fragments. The stars indicate the fragments detected by WB in FIG. 3A. The additional fragments most likely are caspase-derived N-terminal fragments (NTFca). C: recombinant caspase 3 cleaves in vitro translated GGA3 (cold methionine) in three fragments detected in WB by anti-GGA3 antibody (stars indicate the fragments). D: recombinant caspase 3 cleaves endogenous GGA3 from lysates of control cells with a pattern similar to the one observed in H4 apoptotic lysates (stars indicate the fragments). E: apoptosis induced in H4 cells stably overexpressing GGA3 produces a cleavage of GGA3 identical to the one produced by recombinant caspase 3 (stars indicate the fragments). Non-specific bands are also detected just below the ~48 kDa fragment and in correspondence of the ~37 kDa fragment (N.S.). F: Schematic representation of GGA3 caspase cleavage.
Figure 12B:
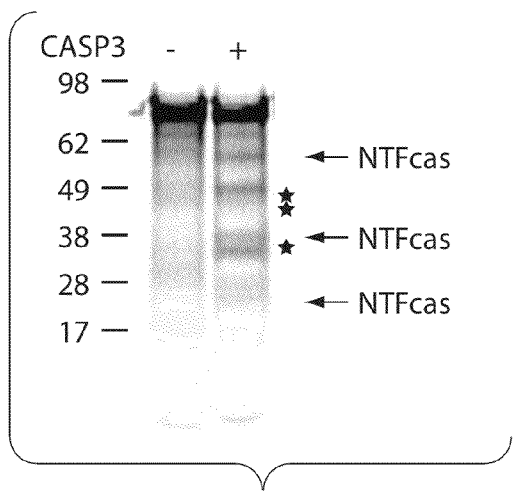
Figure 12C:
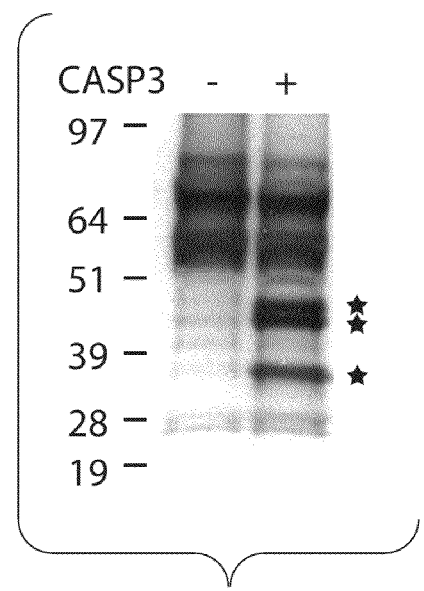
Figure 12D:
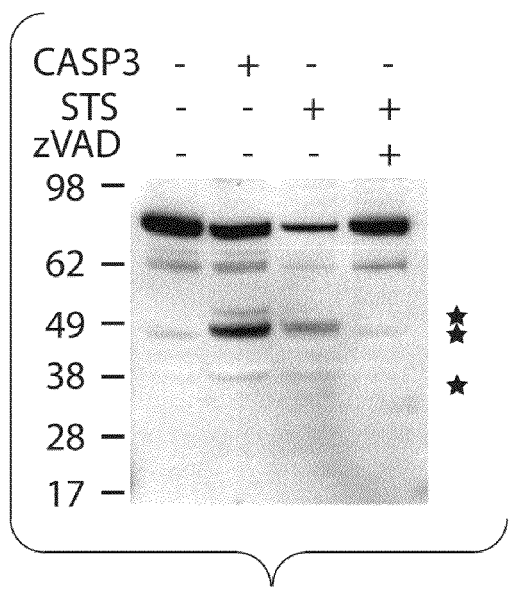
Figure 12E:
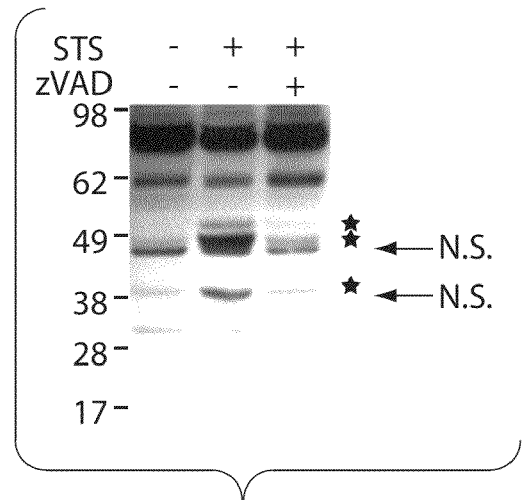
Figure 12F:
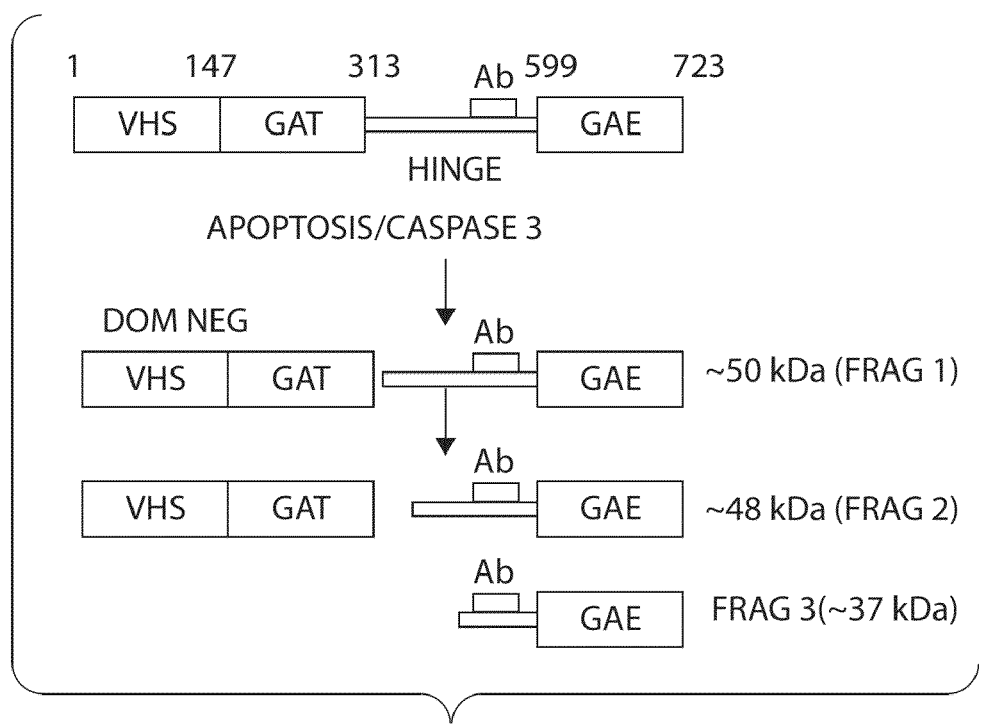

We first asked whether GGA3 is cleaved by caspases during apoptosis. For this purpose, H4-APP751 cells were treated with STS during time course experiments. Western Blot analysis with an anti-GGA3 antibody, targeted to a portion (amino acids 424-542) of the hinge domain of GGA3 (FIG. 12F), revealed that full length GGA3 is cleaved into two major fragments of ~48 and ~37 kDa during apoptosis. β-catenin, which is a known caspase 3 substrate (Brancolini et al., 1998), was cleaved in the H4-APP751 cells with a temporal pattern similar to that observed for GGA3 (FIG. 12A). It is important to note that the fragments were not detected at the 24 hr time point. The latter is most likely due to their degradation during the progression of apoptosis. Since many proteases are activated during apoptosis, we next employed an in vitro cell-free assay to determine whether caspase 3 is capable of cleaving of GGA3 to produce ~48 and ~37 kDa fragments. Recombinant caspase 3 cleaved in vitro translated [$^{35}$S]-labeled GGA3 into several fragments (FIG. 12B). To determine which of these fragments corresponded to the ones detected by WB analysis of the apoptotic lysates, GGA3 was in vitro translated in the presence of cold methionine and then incubated with recombinant caspase 3. Western Blot analysis with anti-GGA3 antibody revealed that recombinant caspase 3 cleaves in vitro translated GGA3 (cold methionine) into three major fragments, the ~48 and ~37 kDa bands along with a third band at ~50 kDa (FIG. 12C). Meanwhile, the additional caspase 3-derived fragments detected in the autoradiography are most likely N-terminal fragments based on the epitope of the anti-GGA3 antibody (FIG. 12F).

Then we assessed whether recombinant caspase 3 cleaves endogenous GGA3 from normal cell lysates and in vitro translated GGA3 to produce similar sets of fragments. Lysates of control cells were incubated with recombinant caspase 3 at 37° for 2 hr. WB analysis with the anti-GGA3 antibody revealed that recombinant caspase 3 cleaves endogenous GGA3 to generate a pattern of fragments similar to that observed in the in vitro assay (three fragments). Treatment of cell lysates with recombinant caspase 3 generated an ~50 kDa GGA3 fragment (FIG. 12D), which was not observed in the H4 apoptotic lysates (FIG. 12A). One possible explanation is that its levels were below the levels of detection in the apoptotic cells. To address this possibility, H4 cells stably overexpressing GGA3 were treated with STS to induce caspase activation. This led to cleavage of GGA3 into a pattern of fragments (FIG. 12E) that was identical to that produced by recombinant caspase 3 cleavage of both in vitro translated GGA3 (FIG. 12C) and endogenous GGA3 in cell lysates (FIG. 12D). Collectively, these data indicate that caspase 3 cleaves GGA3 at three major sites. Given that the anti-GGA3 antibody epitope and the size of the fragments generated during apoptosis, we predicted that caspase-mediated cleavage of GGA3 occurs within the hinge domain (FIG. 12F) to produce three fragments of ~50 kDa (Frag. 1), ~48 kDa (Frag. 2), and ~37 kDa (Frag. 3).

Figure 13B:
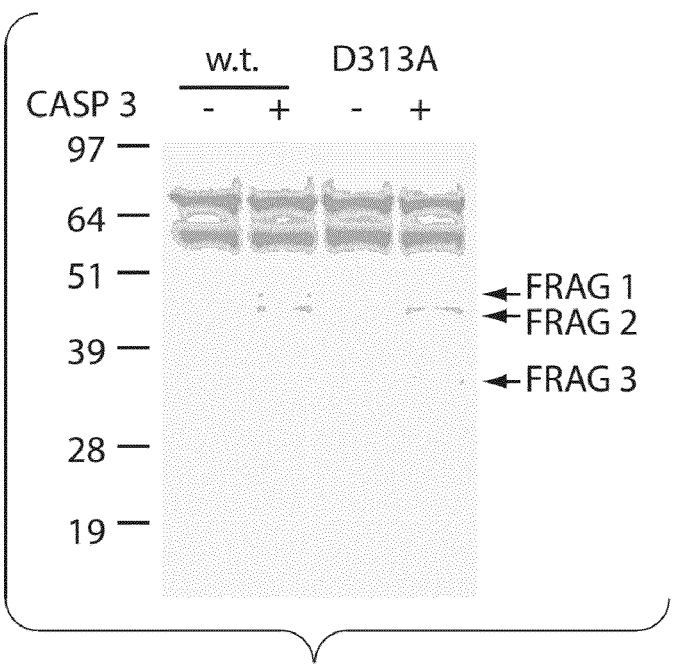
FIG. 13: Site-Directed Mutagenesis of GGA3 at D313/D328/D333/D428 Prevents the Generation of the Three Major Caspase-Derived Fragments.
A: Multiple sequence alignment of human (NP_619525), *mus musculus* (NP_766636), *Bos taurus* (XP_587687) and *canis familiaris* (XP_540429) GGA3. Putative caspase consensus sequence in the hinge and GAE domain are in box. The red bar indicates the epitope recognized by the anti GGA3 antibody. The Hinge domain starts at D313 and ends at V599. The yellow and pink background indicates GAT and GAE domain, respectively. B: Site-directed mutagenesis of D313 to alanine prevents the caspase 3-mediated cleavage of in vitro translated GGA3 (cold) at one of the three major sites (WB with anti-GGA3 Antibody). C: H4 cells were transiently transfected with empty vector, GGA3 wild type (w.t.), and GGA3D313A/D328A/D333A/D428A. The overexpression of GGA3 w.t. induced an artefactual caspase-mediated cleavage (stars indicate the fragments). The cleavage was inhibited when cells were treated with zVAD during the transfection. The caspase-derived fragments were not detected in the GGA3D313A/D328A/D333A/D428A when cells where treated with STS. However zVAD treatment, but not GGA3D313A/D328A/D333A/D428A, preserved full-length GGA3.

Site-Directed Mutagenesis of GGA3 at D313/D328/D333/D428 Prevents the Generation of the Three Major Caspase-Derived Fragments Several putative caspase consensus sites, conserved in the GGA3 sequence of mammals, can be identified in the hinge domain (FIG. 13A). Since the motif $^{310}$TLPD$^{313}$ in GGA3 has previously been shown to serve as a caspase site in the Golgi resident protein, GRASP65 (Lane et al., 2002), we performed site-directed mutagenesis of D313 to alanine. Next, wild type GGA3 (w.t.) and mutated GGA3 (D313A) were in vitro translated in the presence of cold methionine and subjected to the in vitro caspase 3 cleavage assay as described above. Western Blot analysis with anti-GGA3 antibody revealed that the D313A mutation prevented the generation of the caspase-derived ~50 kDa fragment 1 (FIG. 13B).

Figure 13C:
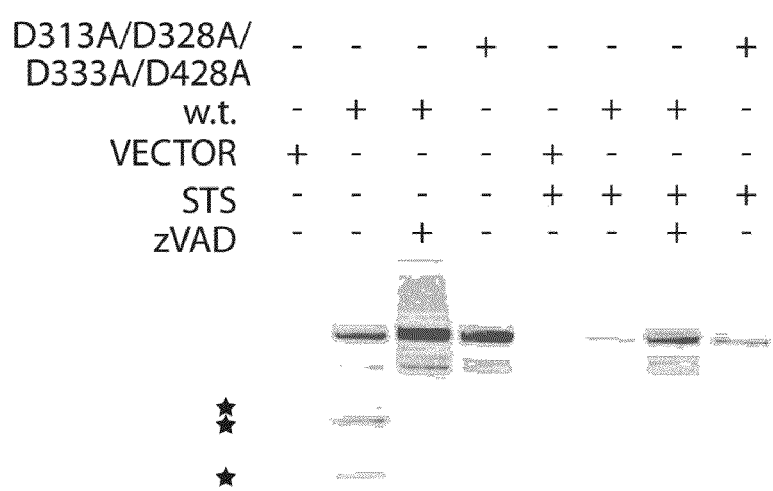

Subsequently, we mutagenized aspartates downstream of D313 and found that D328A/D333A prevented the generation of fragment 2, while D428A prevented the generation of fragment 3 in the in vitro caspase 3-cleavage assay as described above (data not shown). We next tested whether all four mutations D313A/D333A/D328A/D428A could prevent caspase cleavage of GGA3 during apoptosis. H4 cells were transiently transfected with GGA3 w.t. and GGA3-D313A/D328A/D333A/D428A, and then apoptosis was induced by STS treatment. Overexpression of GGA3 w.t. in H4 cells artefactually induced GGA3 caspase cleavage, which was prevented by treatment with zVAD (FIG. 12I). As expected, the GGA3-D313A/D328A/D333A/D428A did not produce fragments 1-3 following caspase activation (FIG. 13C). However, levels of full-length GGA3-D313A/D328A/D333A/D428A were decreased under these conditions, suggesting that GGA3 hosts additional cleavage sites that render it susceptible to its degradation during apoptosis.

Caspase-Mediated Cleavage of GGA3 at D313 Generates a Dominant Negative Molecule It has been previously shown that the moderate expression of a truncated GGA construct lacking the Hinge and GAE domain (GGA1 VHS+GAT) operates as a dominant negative (DN), that blocks the clathrin-dependent transport of the cation-independent MPR from the TGN to the endosomes (Puertollano et al., 2001). Thus, cleavage of GGA3 D313 at the border of the hinge domain would not only reduce active GGA3 molecules during apoptosis, but also potentially generate the equivalent of a dominant negative form of GGA3.

Figure 14A:
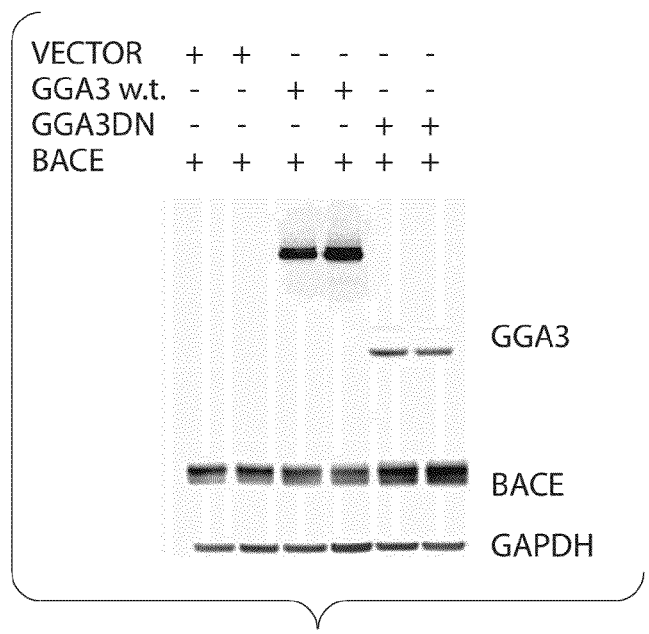
FIG. 14: Caspase-Mediated Cleavage of GGA3 at D313 Generates a Dominant-Negative Molecule.
Figure 14B:
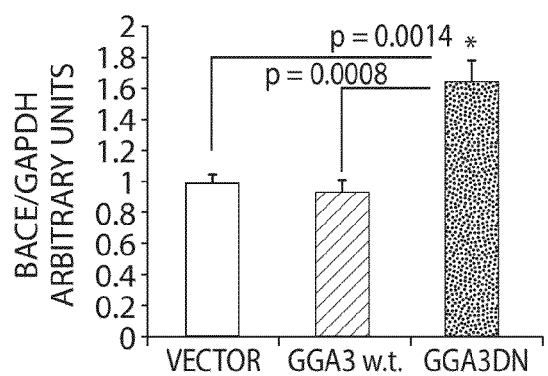
Figure 14C:
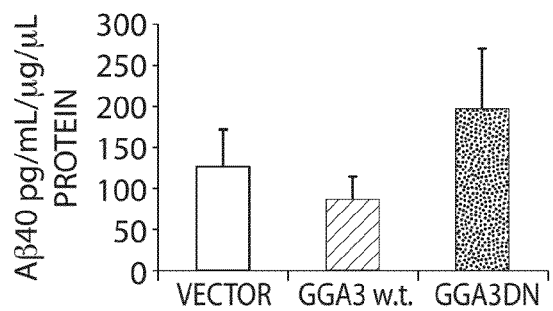

To address this possibility we engineered a HA-tagged GGA3 N-terminal fragment 1-313 mimicking the N-terminal caspase-derived fragment generated by cleavage at D313 (GGA3DN). Then we co-transfected GGA3DN, HA-tagged GGA3 w.t. or vector alone with myc-tagged BACE in H4-APP751 cells (FIG. 14A) and found that BACE levels were increased in the cells expressing GGA3DN compared to cells expressing vector alone or GGA3 (FIG. 14A-B). Levels of secreted Aβ40 also increased in cells expressing GGA3DN (FIG. 14C). However, the increase was not statistically significant because the GGA3DN most likely did not completely inhibit the endogenous GGA3. During apoptosis, however, caspase-mediated cleavage of GGA3 results not only in the production of GGA3DN but also the degradation of GGA3.

RNAi Silencing of GGA3 Increases Levels of BACE, APP-C99, and Aβ

Figure 15A:
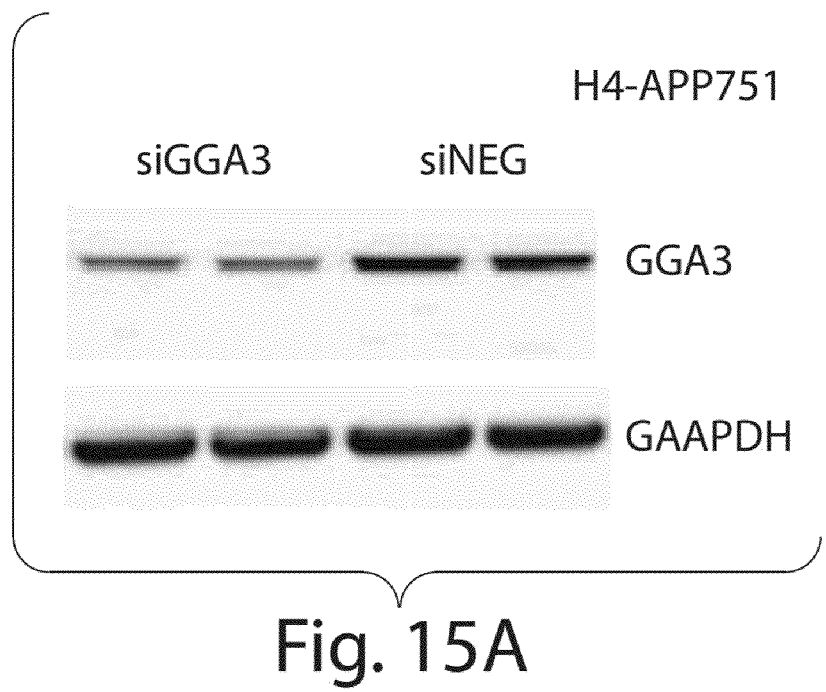
Figure 15B:
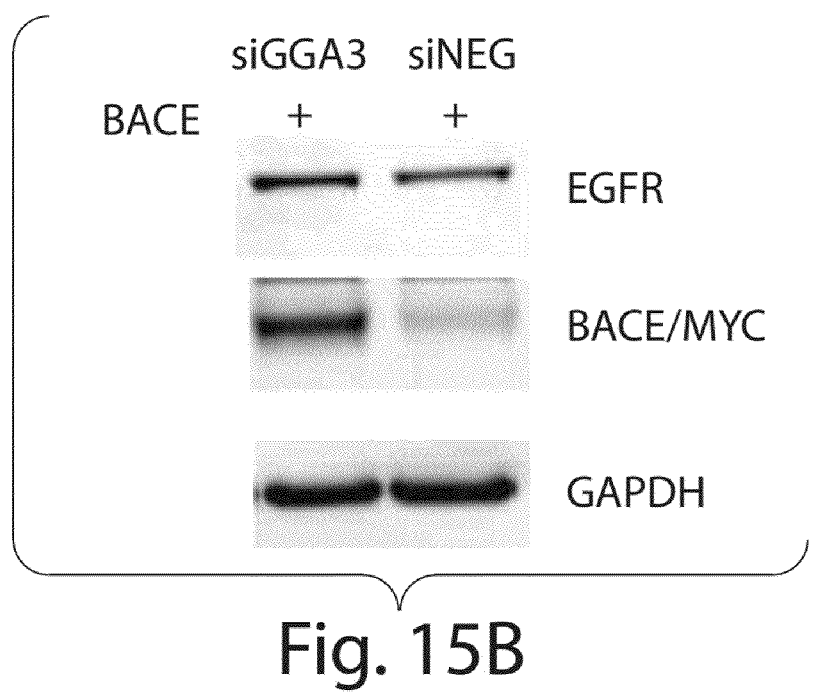
Figure 15C:
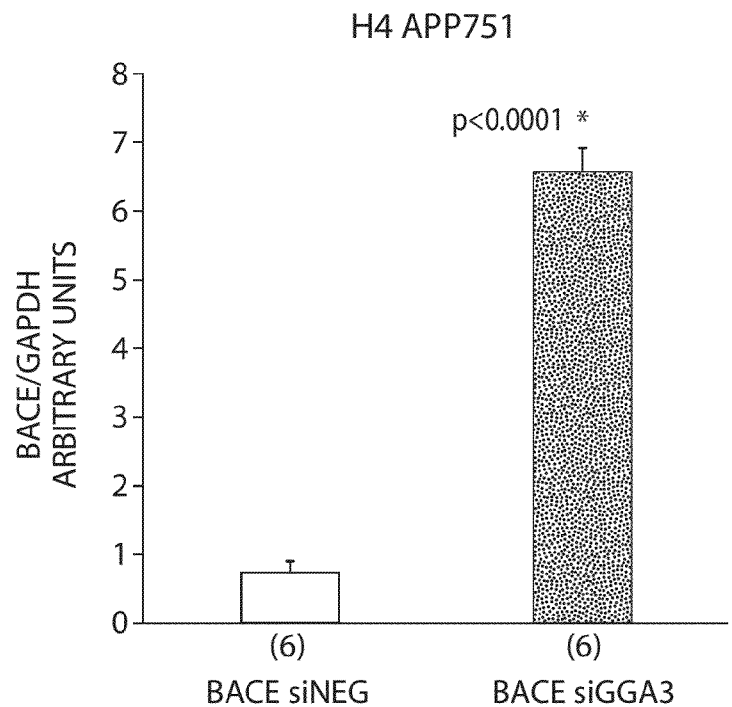
Figure 15D:
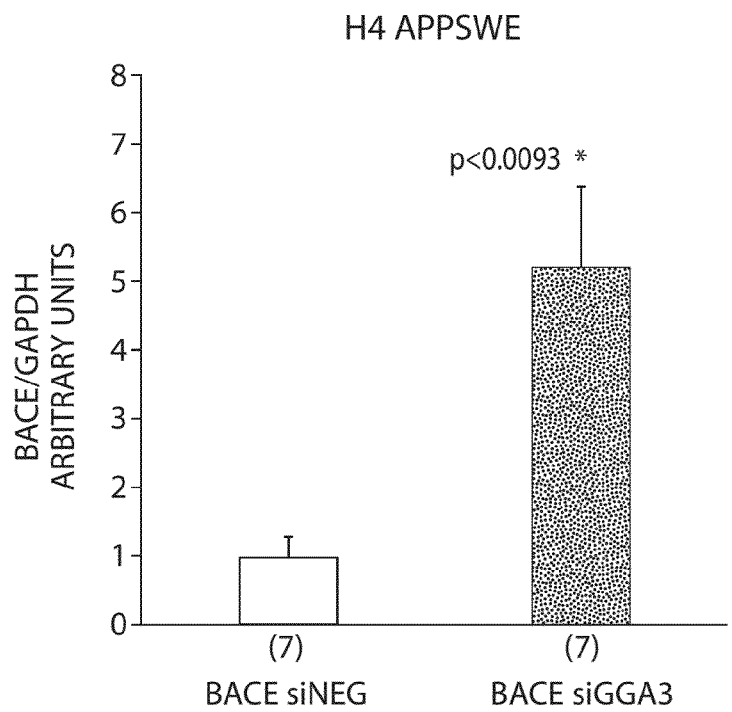
Figure 15E:
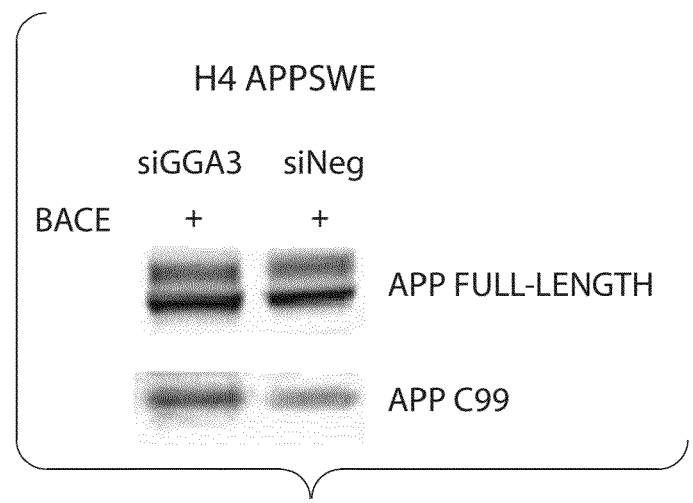
Figure 15F:
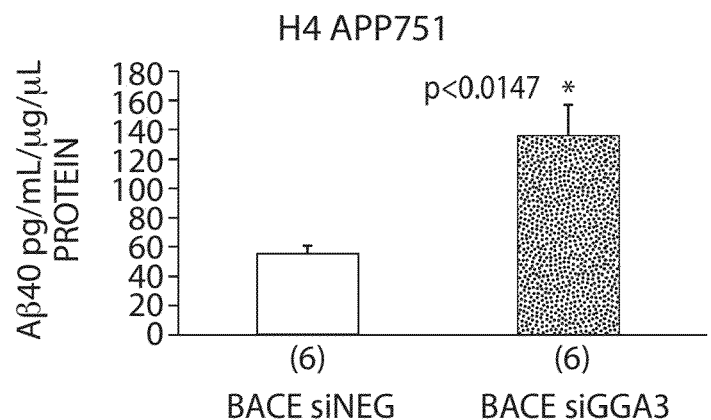
Figure 15G:
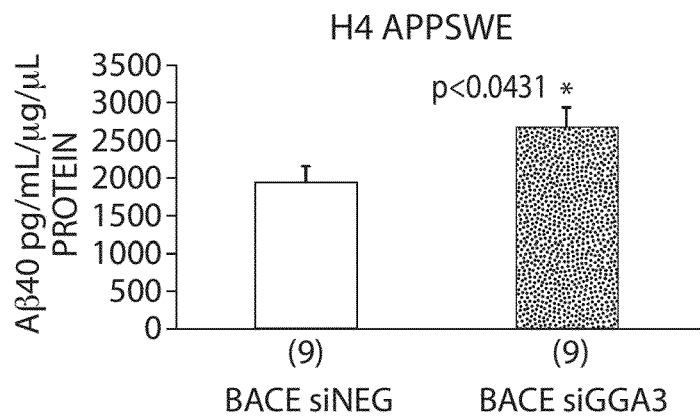
Figure 18B:
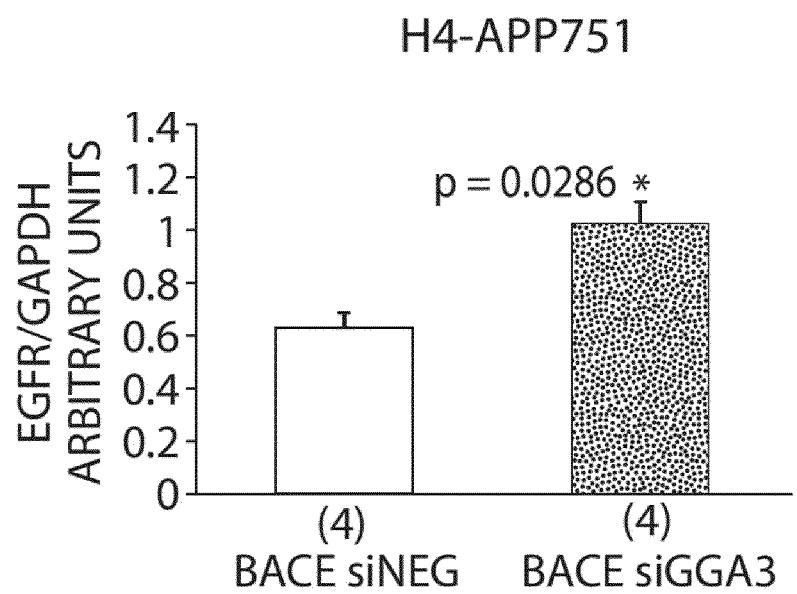
Figure 19A:
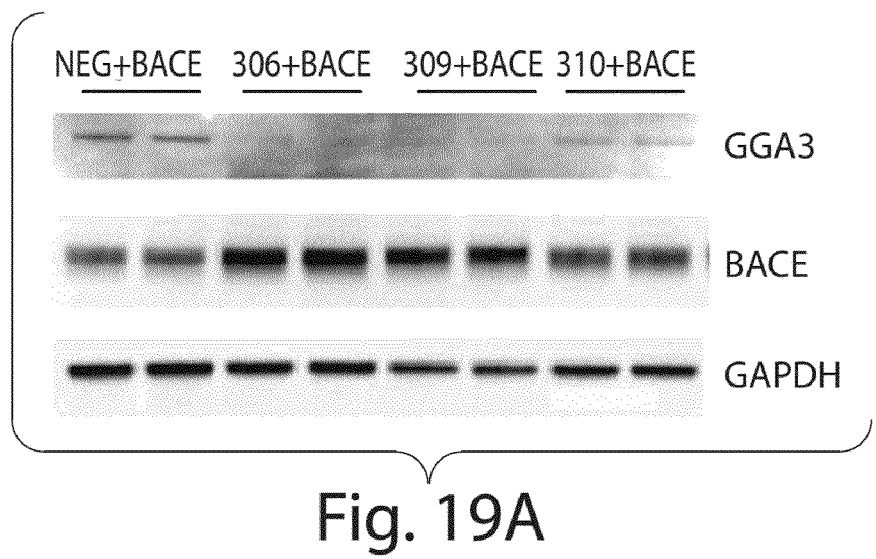
Figure 19B:
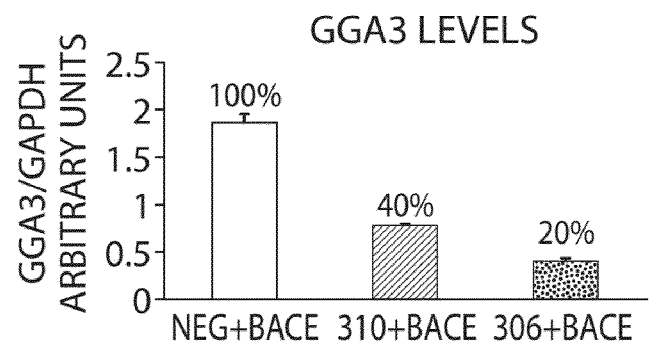
Figure 19C:
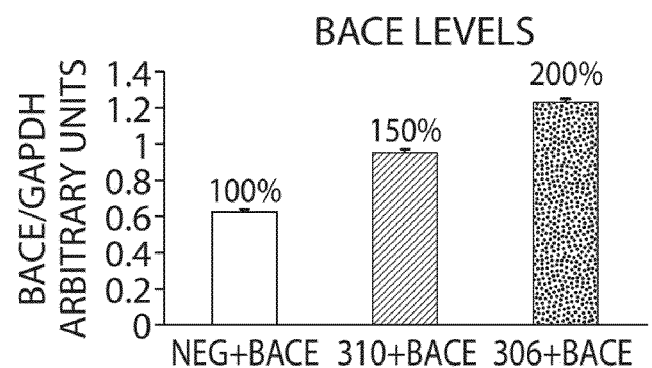
Figure 19D:
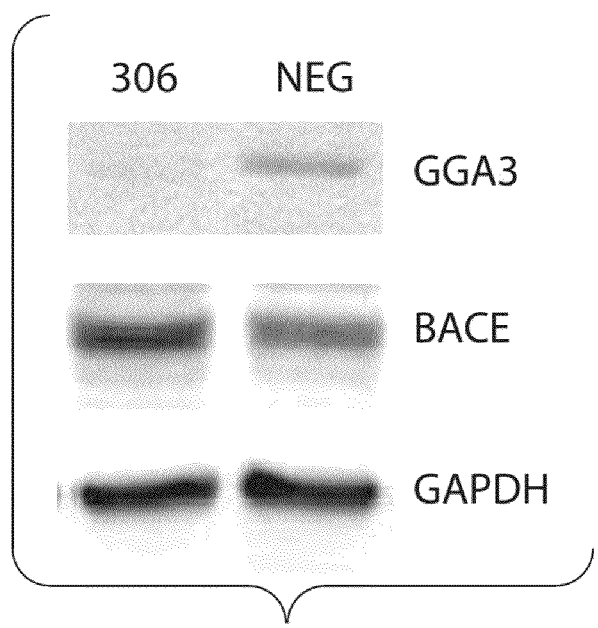
Figure 19E:
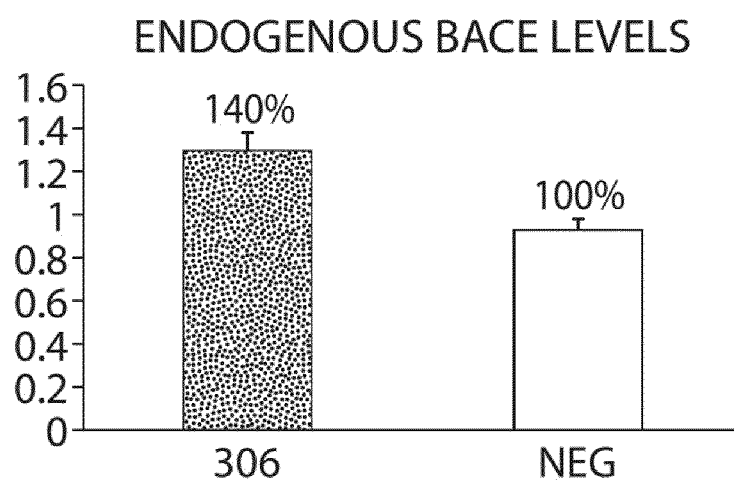

To determine whether GGA3 depletion plays a role in BACE degradation, we assessed the effects of RNAi silencing of GGA3 on BACE and Aβ levels (as measure of β-secretase activity). H4 cells stably expressing wild type APP751 or APP containing the Swedish FAD mutation (APPSwe) were transfected with 200 nM siGGA3 to deplete GGA3. A 19 bp scrambled sequence was used as negative control for siRNA (siNeg). 72 hr later, we measured GGA3 levels and found that endogenous GGA3 was decreased by 50% (FIG. 15A; FIG. 18). At this same time point, a sister plate of the same cells was co-transfected with myc-tagged BACE and either siGGA3 or siNeg. The media was changed after 48 hr. Cells and media were collected 72 hr after co-transfection, and BACE levels were determined by WB using anti-myc antibody. BACE levels were increased by ~7 and ~4 fold in H4-APP751 and H4 APPSWE, respectively (FIG. 15B-C-D). Since degradation of EGFR has previously been shown to be impaired in cells depleted of GGA3, as a positive control, we determined the effect of siRNA silencing of GGA3 on EGFR in these same cells. As expected, decreased levels of GGA3 resulted in increased levels of EGFR protein (FIG. 15B; FIG. 18B). Meanwhile, as a negative control, downregulation of GGA3 had no effect on levels of GAPDH, which was also used as a loading control (FIG. 15B). Similar results were observed in H4 APPSWE cells (data not shown). In accord with these data, levels of APP-C99, detected by WO2 antibody, were increased while levels of full length APP were unchanged in H4-APPSWE cells depleted of GGA3 (FIG. 14E). These data indicate enhanced β-secretase activity. Next, we measured Aβ40 levels in the media (conditioned for 24 hr) by ELISA. Downregulation of GGA3 increased Aβ40 levels by >2 fold in H4-APP751 (FIG. 14F) and by 50% in H4 APPSWE cells (FIG. 15G). As previously reported (Vassar et al., 1999), increased levels of BACE enhance Aβ production to a lesser extent in cells expressing APPSWE than in cells expressing APP wild type. However, increased levels of Aβ corresponded well with the increase in BACE levels in these experiments (FIG. 15B). Similar results were observed when H4 cells stably expressing myc-tagged BACE were co-transfected with siGGA3 and either w.t. APP or APPSWE (data not shown). Our aim was to assess β-secretase activity, and since increases in BACE activity have previously been shown to increase both Aβ40 and Aβ42 (Sinha et al., 1999; Vassar et al., 1999; Yan et al., 1999), we did not measure Aβ42 in these experiments. We confirmed that downregulation of GGA3 increases BACE levels in murine N2A cells using lentiviral vectors expressing shRNA for mouse GGA3. Three shRNA lentiviral vectors downregulated GGA3 to different degree (FIG. 19A-B). Levels of ectopically expressed BACE inversely correlated with GGA3 levels (FIG. 19A-C). Moreover, endogenous BACE also increased upon downregulation of GGA3 (FIG. 19D-E). To determine whether downregulation of GGA3 also affects γ-secretase, GGA3 RNAi has been performed in H4 cells expressing either APP-751 or the APP-CTF (APP105) using lentiviral vectors expressing shRNA for human GGA3 (FIG. 20A). We have found that downregulation of GGA3 produces an increase in Aβ40 generation in full-length APP-751-expressing cell lines but not in the APP-C105-expressing cell lines (FIGS. 20B and C, respectively). These results indicate that depletion of GGA3 affects APP processing independently of 7-secretase activity. It is important to note that BACE levels increase when depletion of GGA3 is achieved with both synthetic RNAi duplex and lentiviral vector expressing shRNA targeting different region of GGA3 gene. Collectively, these findings show that downregulation of GGA3 serves to increase levels of BACE, APP-C99, and Aβ. These data also support the hypothesis that GGA3 normally plays a role in modulating BACE turnover and stability most likely by sorting BACE to lysosomes (based on our earlier findings; (Koh et al., 2005)).

Figure 16A:
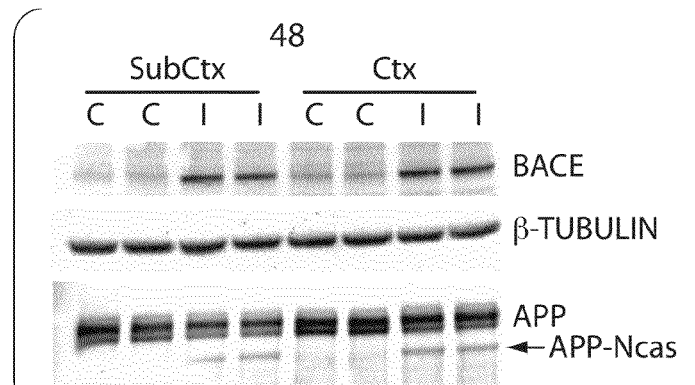
Figure 16B:
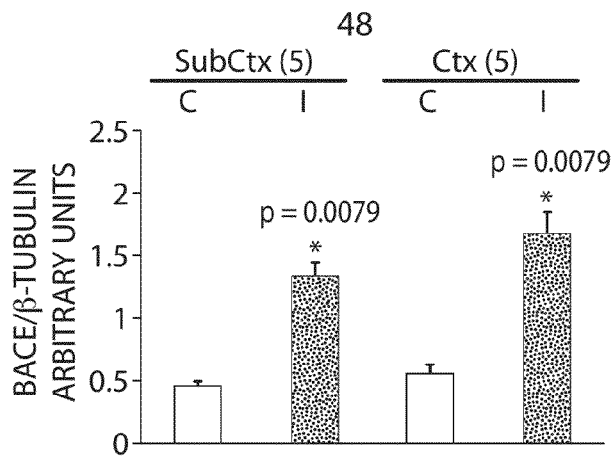

GGA3 is Degraded During Cerebral Ischemia Concurrently with Caspase Activation and Increases in BACE Levels BACE protein levels and activity have previously been shown to be elevated following cerebral ischemia in a rat model (Wen et al., 2004). Previous studies have also shown that caspase 3 activation can be detected following cerebral ischemia from 1 to 24 hr after reperfusion in both mice and in rats (Davoli et al., 2002; Namura et al., 1998). We thus asked whether caspase activation induced by cerebral ischemia leads to degradation of GGA3 and increased levels of BACE protein in the same rat model of cerebral ischemia used by Wen et al. (2004). Ischemic stroke was induced by middle cerebral artery occlusion (MCAO) in rats as previously described (Liu et al., 2002). At 48 hr of reperfusion following induction of cerebral ischemia, BACE protein levels were significantly increased (>2-fold) in the ischemic (ipsilateral) cortical and sub-cortical hemispheres, but not in the contralateral hemispheres (FIG. 16A-B). Increased levels of BACE were detected as early as 12 hr post-reperfusion (data not shown). Unfortunately, we were unable to detect caspases in the rat homogenates by WB. One possible explanation is that the anti-caspase antibodies are human specific and thus unable to detect rat caspases. It is also likely that caspase-3 activation occurs much earlier than the 48 hr time point. Since APP is also a substrate for caspase cleavage (Barnes et al., 1998; Gervais et al., 1999; LeBlanc et al., 1999; Pellegrini et al., 1999; Weidemann et al., 1999), we tested whether APP undergoes caspase-mediated cleavage in the rat brain following ischemia. At 48 hr of reperfusion following induction of cerebral ischemia, full-length APP protein levels were slightly decreased owing to the processing of full-length APP into a fragment of roughly 90 kDa (FIG. 16A), that we have previously reported to be the N-terminal APP caspase fragment in cells undergoing apoptosis (Tesco et al., 2003). Based on APP, caspase activation occurred concomitant with the increase in BACE levels.

Figure 16C:
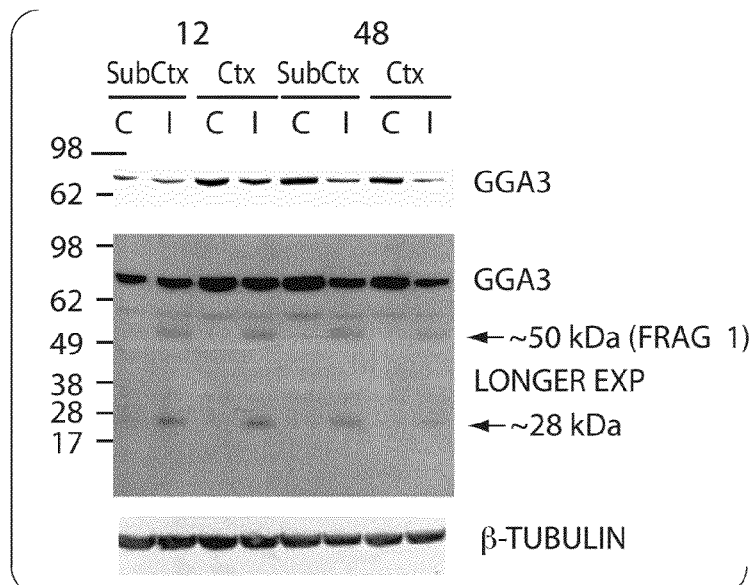

We next determined whether GGA3 undergoes caspase-mediated cleavage during cerebral ischemia. At 12 and 48 hr of reperfusion following induction of cerebral ischemia, GGA3 was cleaved with a temporal pattern similar to that observed for the increase in BACE protein levels (FIG. 16C). GGA3 full length was decreased in the rat ischemic hemisphere samples and two cleavage fragments were detected in the ischemic rat hemisphere: a fragment of ~50 kDa most likely corresponding to fragment 1 generated by cleavage at D313 (FIG. 12C) and a second fragment of ~28 kDa. The origin of the second fragment is not clear; however, one possible explanation is that the 28 kDa fragment may be the result of degradation of the larger fragments detected in the in vitro experiments (FIGS. 11 and 12). In any event, these data indicate that full-length GGA3 is cleaved and depleted following ischemia. Moreover, depletion of GGA3 occurs concurrently with caspase activation (based on caspase cleavage of APP) and increasing levels of BACE in the rat model of cerebral ischemia.

Figure 17A:
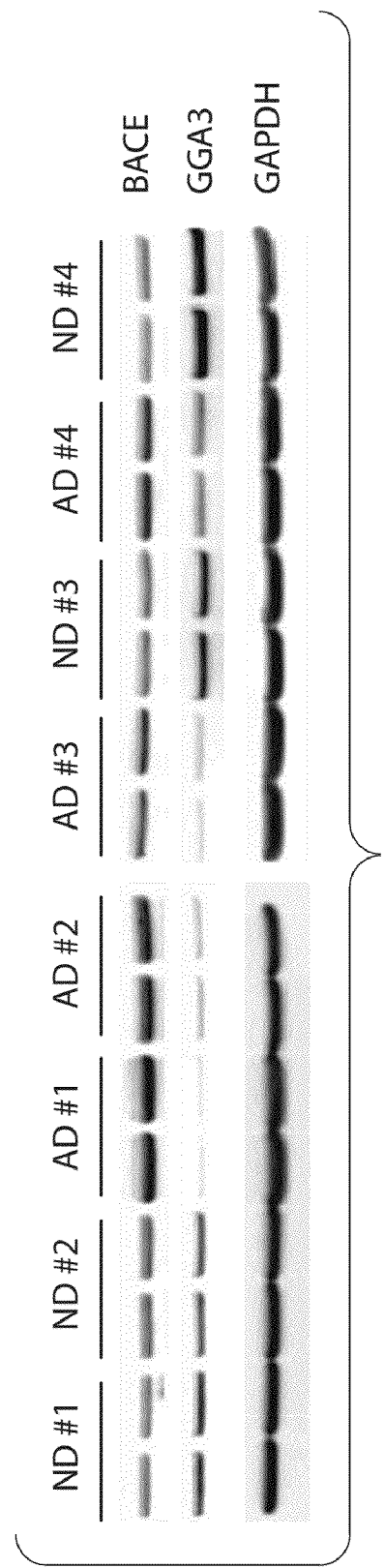
Figure 17B:
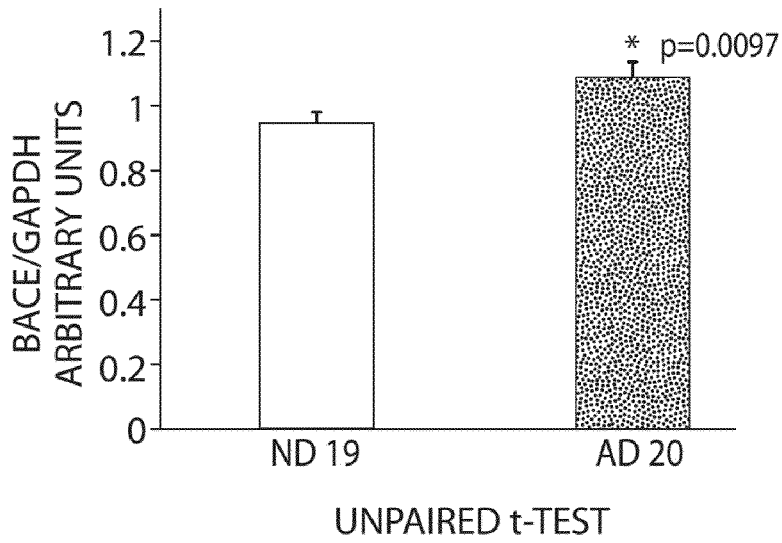
Figure 17C:
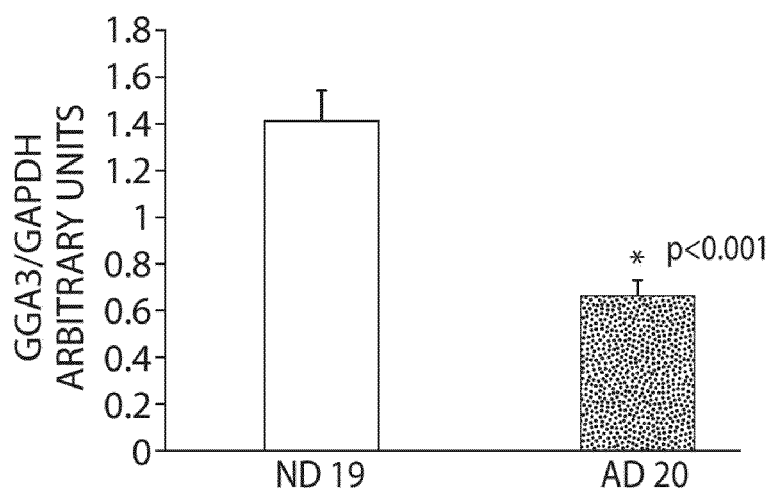
Figure 17D:
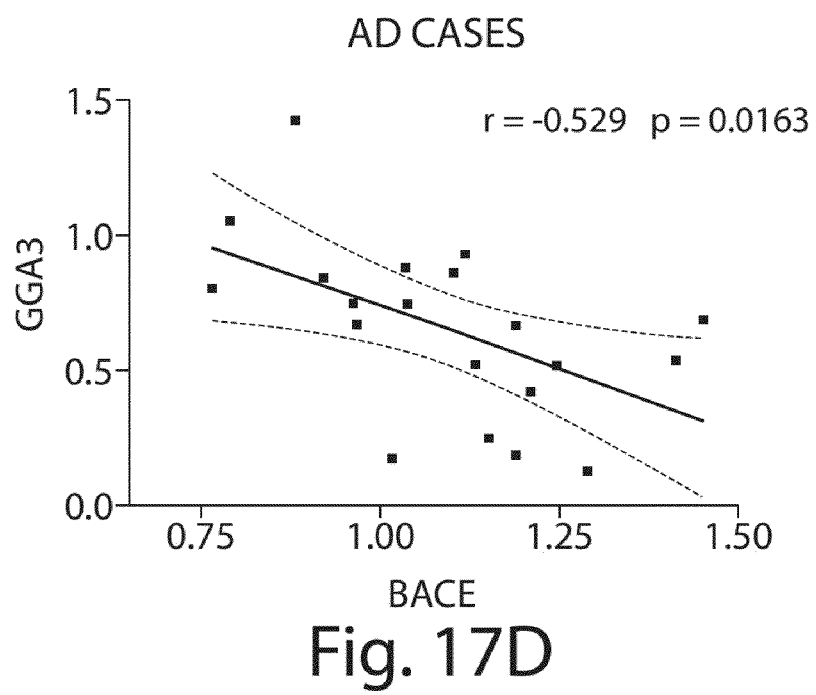
Figure 17E:
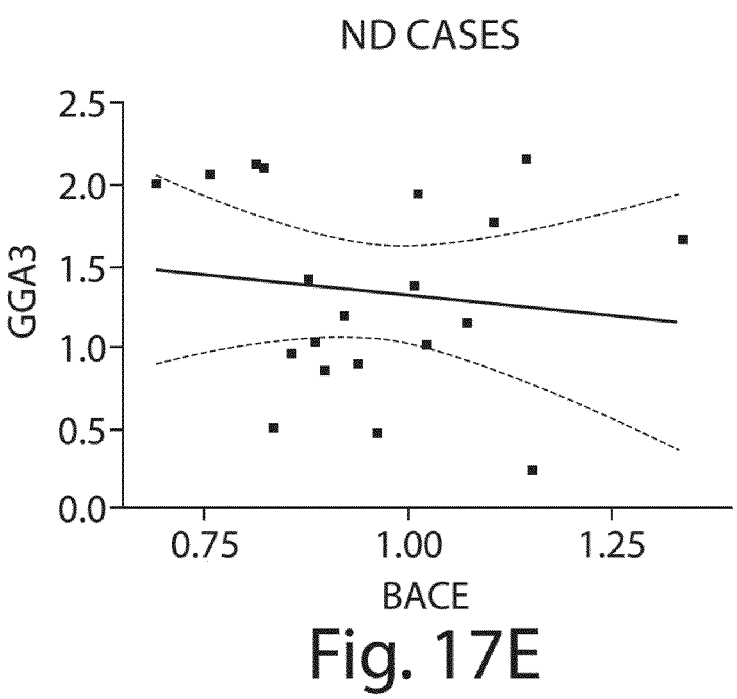
Figure 17F:
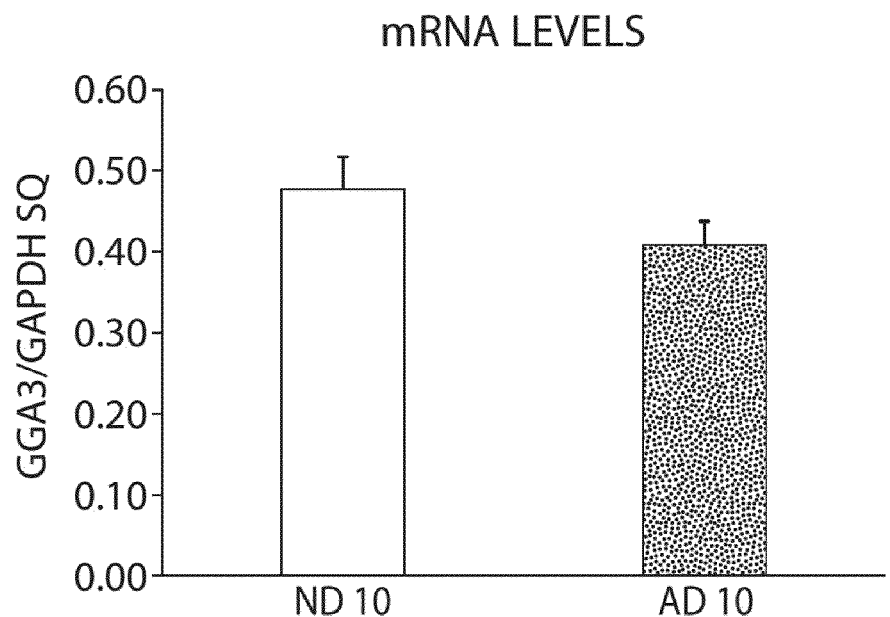
Figure 17G:
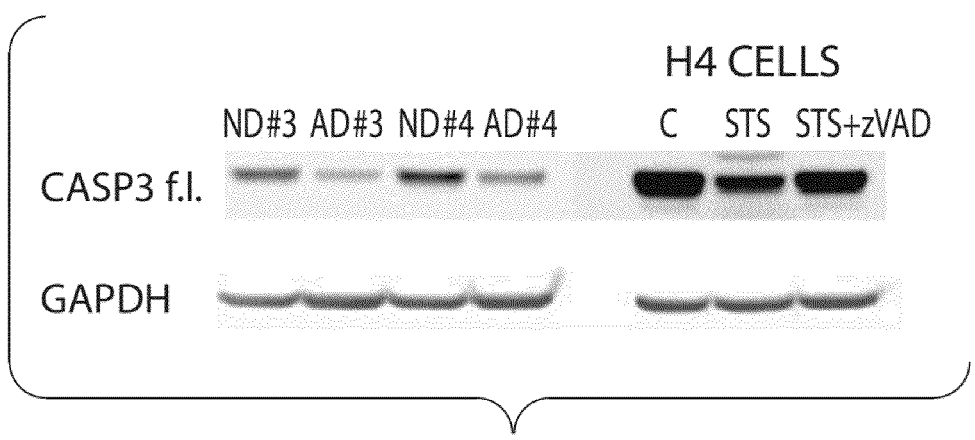
Figure 21A:
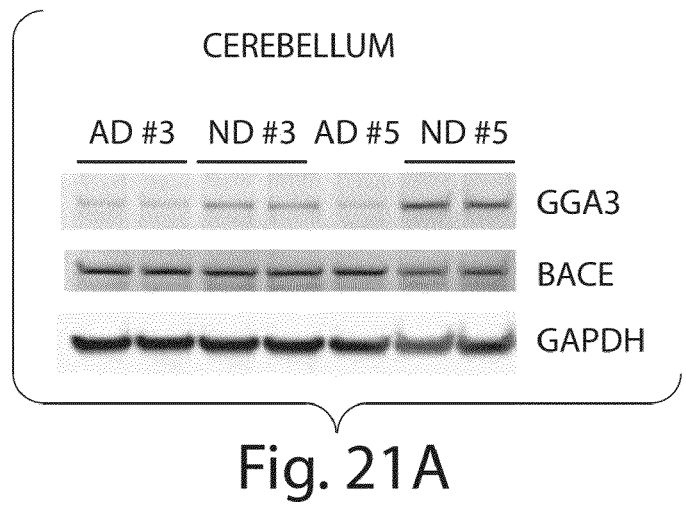
Figure 21B:
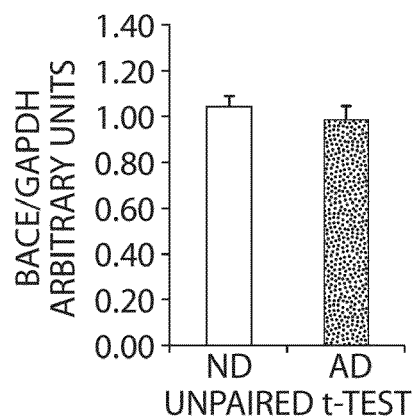
Figure 21C:
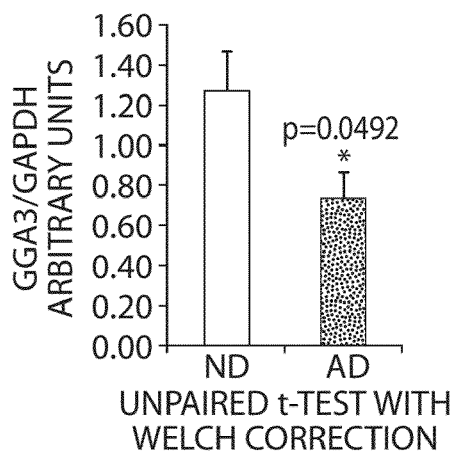
Figure 21D:
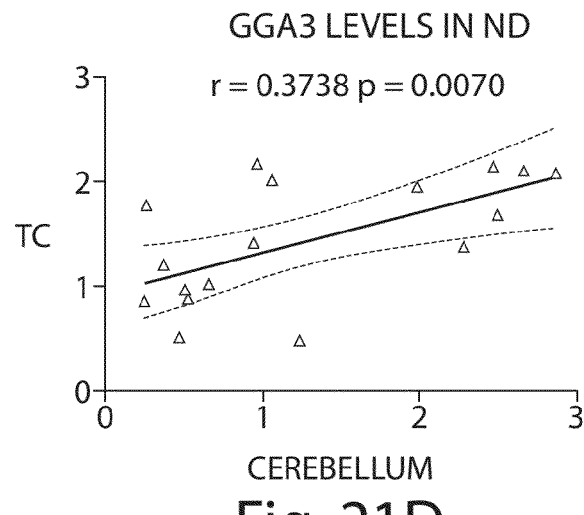
Figure 21E:
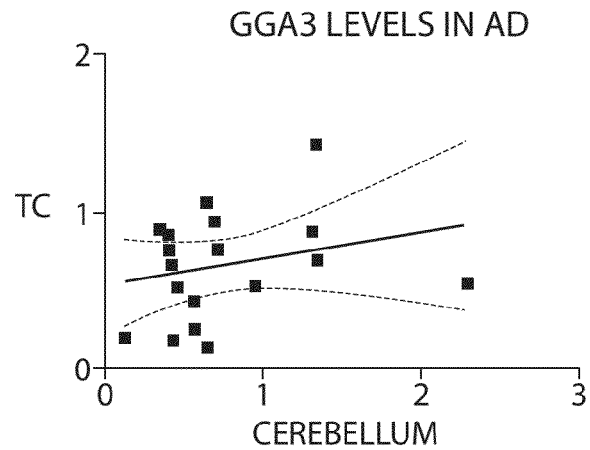
Figure 21F:
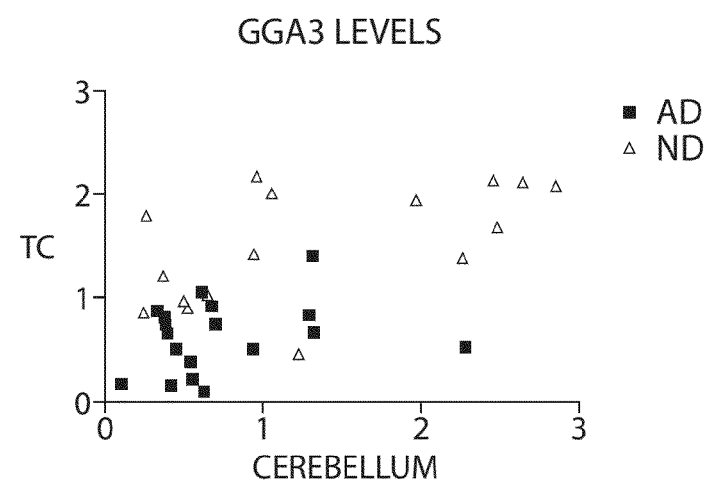

Levels of GGA3 are Decreased and Inversely Correlated with Increased Levels of BACE in AD Temporal Cortex Several studies have shown that BACE protein levels and β-secretase activity are increased in AD brains (Fukumoto et al., 2002; Holsinger et al., 2002; Li et al., 2004a; Tyler et al., 2002; Yang et al., 2003). However, the molecular mechanism underlying these increases remains unresolved. The data presented in this study raise the possibility that increased BACE levels in AD brains may be at least partly due to decreased levels of GGA3. To test this hypothesis, we measured GGA3 and BACE protein levels in 19 non-demented (ND) versus 20 AD brain (temporal cortex) samples that have already been shown to possess increased BACE levels and β-secretase activity (Li et al., 2004a; Tyler et al., 2002). We first confirmed that BACE protein levels are significantly increased in the AD temporal cortex (FIG. 17A-B) as shown by WB analysis using the SECB1 antibody (Li et al., 2004a; Tyler et al., 2002). Next, we found that GGA3 protein levels were significantly decreased in the same set of AD brains (FIG. 17A-C). Moreover, the decreased levels of GGA3 were inversely correlated with the increased BACE levels in the AD group, but not in the ND group (FIG. 17D-E). Quantification of GGA3 mRNA levels by real-time PCR showed that the decrease in GGA3 protein levels is not due to reduced gene expression (FIG. 17F) but most likely occurs at the translational or post-translational level. We next asked whether reduced levels of GGA3 in the AD brains could be due to degradation by caspase 3. Levels of full-length caspase 3 were decreased in the AD (but not ND) brains, most likely because of increased activation as shown to occur in apoptotic H4 cells (STS) (FIG. 17G). However, we were unable to detect either the active caspase 3 fragment or the caspase-derived GGA3 fragments in these brains. One possible explanation is that the caspase-generated fragments were readily degraded in these post-mortem tissues. On the other hand, the GGA3 caspase-derived fragments were also not detectable in cells during advanced apoptosis (FIG. 12A). To further investigate the mechanism underlying our observed depletion of GGA3 in the AD brains, we have analyzed BACE and GGA3 levels not only in the temporal cortex, but also in the cerebellum, which is usually spared of AD pathology (FIG. 21). GGA3 levels were decreased in the cerebellum of AD as compared to control subjects by 40% (FIG. 21C). However, the decrease was more pronounced in the temporal cortex (55%) (FIG. 17). Moreover, while decreased levels of GGA3 inversely correlated with BACE levels in the temporal cortex, BACE levels were not increased in the cerebellum of AD as compared to control subjects (FIG. 21A-B), suggesting that the levels of GGA3 were sufficient for a normal degradation of BACE. The generation of GGA3 null mice, currently not available, will be useful for determining the threshold level of GGA3 depletion required to impair BACE degradation in vivo. While GGA3 levels in the TC correlate with GGA3 levels in the cerebellum in ND (FIG. 21D), such correlation is lost in the AD patients in which the levels of GGA3 are further reduced in the TC (FIG. 21E). These data suggest that subjects with lower levels of GGA3 (FIG. 21F) could be at risk of developing AD in conditions associated with caspase activation e.g. cerebral ischemia or Aβ toxicity, now, selectively in affected brain regions. These findings lend further support to the hypothesis that that GGA3 normally plays a role in modulating BACE turnover and stability, and that pathological conditions in which GGA3 levels are reduced lead to increased levels of BACE and β-secretase activity.

Discussion

Recent studies have revealed BACE as a stress-related protease that is upregulated in the brains of AD patients (Fukumoto et al., 2002; Holsinger et al., 2002; Li et al., 2004a; Tyler et al., 2002; Yang et al., 2003). BACE levels have also been shown to increase following ischemia (Wen et al., 2004); however, the molecular mechanism responsible has remained elusive. Here, we show that caspase activation elevates BACE levels and β-secretase activity owing to post-translational stabilization of BACE. Using a rat ischemia model, we found that levels of GGA3, an adaptor molecule implicated in BACE trafficking, are reduced in a temporally coordinated manner with caspase activation and increases in BACE proteins levels. In cell-based studies, RNAi silencing of GGA3 directly led to increased BACE protein levels and β-secretase activity as evidenced by enhanced APP-C99 and Aβ levels. Together, these data suggest a model in which apoptosis, e.g. induced by ischemia, drives the depletion of GGA3, which, in turn, leads to the stabilization of BACE and increased β-secretase activity. We also analyzed brain samples of AD patients in which BACE levels and β-secretase activity have previously been shown to be elevated in the temporal cortex. In further support of our model of GGA3-dependent degradation/stabilization of BACE, in the brains of AD patients, GGA3 protein levels were significantly decreased. Moreover, this decrease was inversely correlated with increased BACE levels in the temporal cortex.

Decreased levels of GGA3 most likely engender an increase in BACE protein levels by interfering with the sorting of BACE to lysosomes where it is degraded (Koh et al., 2005). GGA3 has previously been demonstrated to target cargo (e.g. EGFR) to lysosomes (Puertollano and Bonifacino, 2004). RNAi silencing of GGA3 resulted in the accumulation of EGFRs in enlarged early endosomes and partially blocked their delivery to lysosomes where they are normally degraded. These studies indicate that GGA3 is involved in the delivery of endosomal cargoes to lysosomes. Recently, He et al. (2005) showed that RNAi silencing of GGAs significantly increases the levels of BACE in endosomes. They also proposed that GGAs are necessary for BACE and MPRs to be transported back to TGN. However, BACE turnover was not assessed in that study, and the accumulation of BACE in endosomes could also be due to decreased degradation resembling the effect of GGA3 downregulation on EGFR degradation (Puertollano and Bonifacino, 2004). The mechanism by which GGA3 targets some cargo (e.g. EGFR) to lysosomes has been shown to be ubiquitin-dependent (Puertollano and Bonifacino, 2004). While there is some evidence that BACE is ubiquitinated (Qing et al., 2004), future studies will be required to determine whether GGA3-dependent degradation of BACE requires ubiquitination, or whether it occurs via an alternate mechanism (e.g. the binding to GGA3-VHS domain).

We have shown that caspase-mediated degradation of GGA3 occurs following cerebral ischemia and propose that it may explain our and others' observations of elevated β-secretase levels (and activity) following cerebral ischemia. As shown in the Nun Study (Kalaria, 2000; Nolan et al., 1998; Snowdon et al., 1997), and recently confirmed in additional prospective autopsy studies (Petrovitch et al., 2005; Riekse et al., 2004), individuals with AD and cerebrovascular pathologies show greater cognitive impairment than those exhibiting either pathology alone. These studies indicate that there is an additive or synergistic interaction between AD and cerebrovascular pathologies. Furthermore, evidence is accumulating that stroke and transient ischemic attacks significantly increase the risk of AD in elderly individuals (Honig et al., 2003; Zlokovic, 2002). A recent family-based study has shown that stroke increases the risk of AD to a similar extent as the presence of an APOE-ϵ4 allele in Latinos (Rippon et al., 2006). Thus, stroke may represent either a precipitating or a triggering event in AD.

While there is an increasing body of knowledge indicating a strong association between cerebrovascular disease and AD (Honig et al., 2003; Rippon et al., 2006), the potential role of apoptosis and cerebral ischemia in AD pathogenesis has remained unclear. Apoptosis has been firmly established to enhance Aβ production in neuronal and non-neuronal cells (Barnes et al., 1998; Galli et al., 1998; Gervais et al., 1999; Guo et al., 2001; LeBlanc, 1995; Sodhi et al., 2004; Tesco et al., 2003). Thus, apoptotic events in the brain, e.g. induced by stroke and ischemia could increase risk for, or trigger AD by driving cerebral Aβ accumulation. Several studies have shown cerebral ischemia to upregulate APP messages containing the Kunitz-type protease inhibitor domain, between 1 and 21 days after reperfusion (Abe et al., 1991; Kim et al., 1998; Koistinaho et al., 1996; Shi et al., 2000). Additionally, APP protein levels were increased between 1 and 10 weeks after reperfusion (Banati et al., 1995; Kalaria et al., 1993; Stephenson et al., 1992; Wakita et al., 1992). BACE protein levels and β-secretase activity have also been shown to be increased in animal models of traumatic brain injury, including cerebral ischemia (Wen et al., 2004) and head injury, which is also a risk factor for AD (Blasko et al., 2004; Chen et al., 2004). More recently, caspase inhibition therapy has been shown to prevent brain trauma-induced increases in Aβ peptide (Abrahamson et al., 2006). Collectively, these findings, taken together with our current data, suggest that accumulative insults to the brain over one's lifetime would progressively increase risk for AD by elevating cerebral Aβ accumulation via BACE stabilization owing to caspase-mediated depletion of GGA3. Furthermore, the effect of BACE stabilization on Aβ levels could also be amplified by other events (e.g. upregulation of APP levels at much later time points, e.g. several days after the ischemic event).

We have also shown that GGA3 levels are reduced both in the temporal cortex and cerebellum of AD patients (versus controls). The decrease in GGA3 levels was more pronounced in the temporal cortex versus cerebellum, which is relatively spared of AD pathology. Importantly, decreased levels of GGA3 were inversely correlated with increased levels of BACE only in the temporal cortex, which is strongly impacted by AD pathology. In contrast, BACE levels were not significantly increased in the cerebellum of AD patients as compared to control subjects. These findings suggest that some subjects have lower levels of GGA3 independently of AD pathology, e.g. in cerebellum. Subjects with lower levels of GGA3 may be at risk of developing AD given that conditions associated with caspase activation e.g. stroke, which is a risk factor for AD, may further decrease GGA3 levels triggering or precipitating AD pathology.

The contribution of apoptosis to the etiology and pathogenesis of AD remains unclear largely due to the difficulties involved in identifying classic apoptotic markers in vivo (for review see (Cribbs et al., 2004; LeBlanc, 2005). This is most likely due to the long duration of AD and the very rapid clearance of apoptotic cells. Contradictory results could be at least partially due to the use of post-mortem tissues. Many factors (e.g. length of agonal state, collection of tissue at the end point of the disease and time interval before freezing the tissue) may significantly affect the analysis of enzymatic activities. It is also possible that many senile plaques, which can take many years to form, are no longer surrounded by apoptotic neurons by the time of autopsy. On the other hand genetic evidence for sporadic AD, such as the disease associations with DAPK1 (Li et al., 2006), GAPD (Li et al., 2004b) and LOC439999 (Grupe et al., 2006) variants, also point to apoptosis as a disease-relevant process. While there is increasing evidence for caspase activation in AD brain (for review see (Cribbs et al., 2004; LeBlanc, 2005), we cannot rule out the possibility that genetic factors and/or other post-translational mechanisms (e.g. other proteases) may contribute to GGA3 depletion in AD brain.

In summary, our studies suggest that elevated BACE protein levels found in AD patients and animal models of traumatic brain injury including ischemia and acute head trauma, may be at least partly due to impaired degradation and stabilization of BACE. This would then lead to increased production of the Aβ peptide, thereby contributing to AD pathogenesis. Since Aβ has also been reported to induce apoptosis, this could result in a vicious cycle that autopotentiates Aβ generation and cell death. Finally, our in vivo and in vitro data implicate GGA3 as the key player in regulating degradation of BACE in its capacity as a trafficking molecule that delivers BACE to the endosomal-lysosomal system.

Experimental Procedures

Aβ ELISA

Secreted Aβ40 was measured in the conditioned media using an Aβ40-specific sandwich ELISA (BioSource International, Camarillo, Calif.). Aβ concentration was normalized against the concentration of protein in the cell lysates.

Cycloheximide Degradation Time-Course

H4-APP751 cells were treated with CHX (40 μg/ml) only or STS (1 μM)+CHX during a 30 hr time-course. Lysates from each time point were immunoblotted with the specific antibodies, anti-BACE, anti-TACE, and the anti-APP antibody A8717.

In Vitro Translation and Recombinant Caspase 3 Cleavage Assay

The HA-GGA3 pcDNA4 plasmid was a generous gift from Dr. Waguri. GGA3 was in vitro translated (IVT) in the presence of [$^{35}$S]-labeled methionine using TNT Quick Coupled Transcription/Translation Systems as indicated by the manufacturer (Promega, Madison Wis.). 5 μL of IVT reaction were incubated with or without 200 ng of recombinant caspase 3 (Pharmingen, San Diego, Calif.) in caspase reaction buffer (sucrose 20%, NaCl 100 mM, HEPES (pH 7.4) 20 mM, CHAPS 0.1%, DTT 10 mM, EDTA 1 mM) at 37° for 2 hr. The reactions were separated by SDS-page (4-12% Bis-tricine gel with MES running buffer, Invitrogen Carlsbad, Calif.). The gel was fixed, dried and exposed to a phosphorimager screen. The images were acquired with a FX phosphorimager (Bio-Rad, Hercules Calif.). GGA3 in vitro translation was also performed in the presence of cold methionine. Then, 5 μL of IVT reaction were incubated with or without 200 ng of recombinant caspase 3 overnight at 37°. The reactions were separated by SDS-page. In order to better separate the bands generated by caspase 3 cleavage we used 12% Bis-tricine gel and MOPS running buffer (Invitrogen). Then, the proteins were transferred to PVDF membrane and WB analysis with anti-GGA3 antibody was performed.

GGA3 RNAi Silencing

H4 cells stably expressing wild-type APP-751 or APP containing the Swedish FAD mutation (APPSwe) were transfected with 200 nM siGGA3 (ID #36847, Ambion, Austin Tex.) or a 19 bp scrambled sequence was used as negative control for siRNA (Silencer Negative control #1 siRNA, Ambion) using oligofectamine following manufacturer's instructions (Invitrogen). 72 hr later, GGA3 levels were determined by WB analysis with anti-GGA3 antibody (Transduction Laboratories). At the same time point, a sister plate of the same cells was co-transfected with myc-tagged BACE plasmid and siGGA3 or siNeg. After 48 hr the media was replaced. Cells and media were collected after 72 hr following the co-transfection.

Human Brain Samples, Protein and RNA Extraction

20AD and 19ND temporal cortex were obtained from the Brain Donation Program, Sun Health Research Institute, Sun City, Ariz., USA. Human tissue was collected with informed consent of subjects or next of kin and with ethical approval from the Sun Health IRB. Brain Total RNA was obtained by RNA mini column kit (Qiagen) by following the manufactory's instruction. For protein extraction, small piece of temporal cortex was homogenized by 1×RIPA buffer plus PMSF and proteinase inhibitors mix (Sigma), and protein concentration were measured by protein assay kit (Bio-Rad).

Densitometry and Statistical Analysis

Densitometry analysis was performed on a Macintosh computer using the public domain NIH Image program (developed at the U.S. National Institutes of Health and available on the Internet at rsb.info.nih.gov/nih-image/) or using a Versadoc Imager and QuantityOne software (BioRad). Statistical analysis was performed using Instat3 software. Unpaired T-test was employed for data sets that passed normality test. Unpaired T-test with Welch correction was employed for data set that passed normality test but had different standard deviations. Mann-Whitney test was employed for data set that did not pass normality test.

Chemicals and Antibodies

Staurosporine, cycloheximide, and zVAD were purchased from Calbiochem (La Jolla, Calif.). Recombinant caspase 3 was purchased from Pharmingen (San Diego, Calif.). The anti-caspase 3 active fragment, anti-caspase 3, anti-EGFR, anti-HA, anti-Myc antibodies were purchased from Cell Signaling (Danvers, Mass.). The anti-BACE C-terminal antibody was purchased from Affinity Bioreagents (ABR, Golden, Colo.). The polyclonal antibody A8717, raised against the C-terminus of APP, and the anti-β-tubulin antibody were purchased from Sigma (St Louis, Mo.). The monoclonal antibody, WO2, raised against 1-17 amino acids of Aβ region was a gift from Dr. Beyreuther. The Asp-1 antibody was purchased from Oncogene (Cambridge Mass.). The anti-TACE antibody was purchased from Santa Cruz (Santa Cruz, Calif.). The anti-Cu,Zn—SOD antibody was a gift from Dr. Naoyuki Taniguchi. The monoclonal antibodies anti-GGA3 and anti-β-catenin were purchased from Transduction Laboratories (Newington, N.H.). BACE was detected in human brains by SECB1, which recognizes amino acids 296-310 of BACE amino terminus (Li et al., 2004; Yang et al., 2003). The GAPDH antibody was purchased from Chemicon, Temecula Calif.

Cell Culture, Western Blot Analysis, and Induction of Apoptosis

H4 human neuroglioma cells expressing APP751 (H4-APP751) and APP-SWE (H4-APPSWE) were grown in DMEM containing 10% FBS, 200 µg/mL G418, 250 µg/mL zeocin, 2 mM L-glutamine, 100 U/ml penicillin, 100 µg/mL streptomycin. For the induction of apoptosis, we used staurosporine or etoposide (Calbiochem). For time-course experiments, cells were seeded at a density of $2 \times 10^6$ cells per 100 mm dish and treated with STS (1 µM) or etoposide (100 µg/mL). In order to inhibit caspase activation a sister plate of cells was pretreated with zVAD (100 µM, Calbiochem) for 1 hr before STS treatment. At different time points (0, 3, 6, 9, 12, and 24 hr), the cells were scraped, centrifuged, and then lysed in buffer containing 1% NP40. Western blot analysis was performed as previously described (Tesco et al., 2003). Densitometry analysis was performed on a Macintosh computer using the public domain NIH Image program (developed at the U.S. National Institutes of Health and available on the Internet at rsb.info.nih.gov/nih-image/) or using a Versadoc Imager and QuantityOne software (BioRad).

RNA Isolation and Northern Blot Analysis

Total RNA was extracted using TRIZOL (Invitrogen). Northern blot analysis was performed as previously described (Koh et al., 2001). Human cDNA of BACE was labeled with [γ-32P]dCTP (PerkinElmer, Norwalk Conn.) using random hexanucleotide primers (Prime-a-gene labeling system; Promega Madison Wis.).

Metabolic Labeling and Pulse-Chase Experiments

H4-APP751 cells were preincubated in methionine/cysteine-free (starve) medium for 30 min, after which they were incubated in starve medium supplemented with 1 mCi of [$^{35}$S]methionine/cysteine (Amersham, Piscataway N.J.) per well for 60 min (pulse). Then, cells were incubated in the presence of excess amounts of cold methionine/cysteine for indicated time (chase). The cells were then washed, lysed in radioimmunoprecipitation assay (RIPA) buffer (1% sodium deoxycholate, 0.1% SDS, 1% Triton X-100, 5 mM EDTA, 50 mM Tris, pH 8, 150 mM NaCl), and immunoprecipitated with the specific antibodies. Samples were separated by SDS-PAGE using 4-12% gels, fixed, dried, and exposed to film or a phosphorimaging screen (Bio-Rad). Images were analyzed using a Personal Molecular Imager FX and quantified using Quantity One software (Bio-Rad, Hercules Calif.). For BACE pulse chase experiments, the anti-BACE antibodies were unable to immunoprecipitate endogenous BACE. Thus, H4-APP751 cells were transfected with 10 µg of pcDNA-BACE-myc cDNA using Superfect (Qiagen, Bothell Wash.) according to the manufacturer's protocol. 24 hr following transfection, cells were harvested and pooled together to avoid difference in transfection efficiency and plated again. After 24 hr, cells were metabolically labeled as described above.

Middle Cerebral Artery Occlusion

Female Charles River Sprague-Dawley rats (250 g, Wilmington, Mass.) were acclimatized for three days before surgery. Bilateral ovariectomy was performed 2 weeks before MCAO. The University of North Texas Health Science Center Animal Care and Use Committee approved all animal procedures. Ischemic stroke was induced by occlusion of the middle cerebral artery (MCAO) as described before (Wen et al., 2004). The animals were anesthetized and decapitated at the desired time after the onset of reperfusion (12, 24 and 48 hrs). The brains were harvested, separated into ischemic and non-ischemic hemisphere, dissected in cortex (Ctx) and sub-cortex (Suc-Ctx), and frozen in liquid nitrogen. Then, the tissues were homogenized in RIPA buffer and analyzed by WB.

Real Time PCR

Total RNA was extracted using RNeasy Mini Kit (Qiagen). Equal quantities of DNAse treated RNA samples were subjected to cDNA synthesis using Superscript III Reverse Transcriptase (Invitrogen). Subsequently, SYBR Green Master PCR Mix (Applied Biosystems) and target-specific PCR primers for GGA3 (5'-GGGACAGGGTGTGAGAAAG-3' and 5'-AGAGGGGATCAGCGTCCTAT-3') and GAPDH (5'-GGTCTCCTCTGACTTCAACA-3' and 5'-GTGAGGGTCTCTCTCTTCCT-3') were used for amplification of cDNA samples with iCycler real time PCR machine (Bio-Rad).

PCR primers were designed to amplify a region flanking two different exons and the target specificity of PCR products were confirmed by sequencing. Standard curve method was used to obtain GAPDH normalized GGA3 values.

Site-Directed Mutagenesis

Site-directed mutagenesis was performed using QuickChange site-directed mutagenesis kit (Stratagene) according to manufacturer's instructions. The primers used to produce the D313A substitution: (forward) CCTTAACCCTGCCTGCCTCGGAAGGAAAC and (reverse) GTTTCCTTCCGAGGCAGGCAGGGTTAAGG. The primers used to produce D328A mutation were: (forward) GGCACGCTCATCGCCCTTGCGGAGCTGG and (reverse) CCAGCTCCGCAAGGGCGATGAGCGTGCC. The primers used to produce D333A mutation were: (forward) GACCTTGCGGAGCTGGCCACGACCAACAG and (reverse) CTGTTGGTCGTGGCCAGCTCCGCAAGGTC. The primers used to produce D428A mutation were: (forward) CAGTCCGACCTGGCCTTCTTCAGCCCC and (reverse) GGGGCTGAAGAAGGCCAGGTCGGACTG. The GGA3DN was produced with the introduction of a stop codon. The primers used to produce GGA3DN were: (forward) CCCTGCCTGACTAGGAAGGAAACAGTCAGTGC and (reverse) GCACTGACTGTTTCCTTCCTAGTCAGGCAGGG. The resulting cDNA constructs were sequenced for verification.

Lentiviral RNAi

Custom-designed lentiviral vectors (pLKO.1) carrying expression cassettes that express shRNAs that target human and mouse GGA3 gene were purchased from Sigma. The packaging of the virus was performed as previously described (Sena-Esteves et al., 2004).

REFERENCES

Abe, K., Tanzi, R. E., and Kogure, K. (1991). Selective induction of Kunitz-type protease inhibitor domain-containing amyloid precursor protein mRNA after persistent focal ischemia in rat cerebral cortex. Neurosci Lett 125, 172-174.

Abrahamson, E. E., Ikonomovic, M. D., Ciallella, J. R., Hope, C. E., Paljug, W. R., Isanski, B. A., Flood, D. G., Clark, R. S., and Dekosky, S. T. (2006). Caspase inhibition therapy abolishes brain trauma-induced increases in Abeta peptide: Implications for clinical outcome. Exp Neurol 197, 437-450.

Banati, R. B., Gehrmann, J., Wiessner, C., Hossmann, K. A., and Kreutzberg, G. W. (1995). Glial expression of the beta-amyloid precursor protein (APP) in global ischemia. J Cereb Blood Flow Metab 15, 647-654.

Barnes, N. Y., Li, L., Yoshikawa, K., Schwartz, L. M., Oppenheim, R. W., and Milligan, C. E. (1998). Increased production of amyloid precursor protein provides a substrate for caspase-3 in dying motoneurons. J Neurosci 18, 5869-5880.

Blasko, I., Beer, R., Bigl, M., Apelt, J., Franz, G., Rudzki, D., Ransmayr, G., Kampfl, A., and Schliebs, R. (2004). Experimental traumatic brain injury in rats stimulates the expression, production and activity of Alzheimer's disease beta-secretase (BACE-1). J Neural Transm 111, 523-536.

Bonifacino, J. S. (2004). The GGA proteins: adaptors on the move. Nat Rev Mol Cell Biol 5, 23-32.

Bonifacino, J. S., and Traub, L. M. (2003). Signals for sorting of transmembrane proteins to endosomes and lysosomes. Annu Rev Biochem 72, 395-447.

Brancolini, C., Sgorbissa, A., and Schneider, C. (1998). Proteolytic processing of the adherens junctions components beta-catenin and gamma-catenin/plakoglobin during apoptosis. Cell Death Differ 5, 1042-1050.

Chen, X. H., Siman, R., Iwata, A., Meaney, D. F., Trojanowski, J. Q., and Smith, D. H. (2004). Long-term accumulation of amyloid-beta, beta-secretase, presenilin-1, and caspase-3 in damaged axons following brain trauma. Am J Pathol 165, 357-371.

Citron, M. (2004). Beta-secretase inhibition for the treatment of Alzheimer's disease—promise and challenge. Trends Pharmacol Sci 25, 92-97.

Cribbs, D. H., Poon, W. W., Rissman, R. A., and Blurton-Jones, M. (2004). Caspase mediated degeneration in Alzheimer's disease. Am J Pathol 165, 353-355.

Davoli, M. A., Fourtounis, J., Tam, J., Xanthoudakis, S., Nicholson, D., Robertson, G. S., Ng, G. Y., and Xu, D. (2002). Immunohistochemical and biochemical assessment of caspase-3 activation and DNA fragmentation following transient focal ischemia in the rat. Neuroscience 115, 125-136.

De Strooper, B., and Annaert, W. (2000). Proteolytic processing and cell biological functions of the amyloid precursor protein. J Cell Sci 113 (Pt 11), 1857-1870.

Fukumoto, H., Cheung, B. S., Hyman, B. T., and Irizarry, M. C. (2002). Beta-secretase protein and activity are increased in the neocortex in Alzheimer disease. Arch Neurol 59, 1381-1389.

Galli, C., Piccini, A., Ciotti, M. T., Castellani, L., Calissano, P., Zaccheo, D., and Tabaton, M. (1998). Increased amyloidogenic secretion in cerebellar granule cells undergoing apoptosis. Proc Natl Acad Sci USA 95, 1247-1252.

Gervais, F. G., Xu, D., Robertson, G. S., Vaillancourt, J. P., Zhu, Y., Huang, J., LeBlanc, A., Smith, D., Rigby, M., Shearman, M. S., et al. (1999). Involvement of caspases in proteolytic cleavage of Alzheimer's amyloid-beta precursor protein and amyloidogenic A beta peptide formation. Cell 97, 395-406.

Grupe, A., Li, Y., Rowland, C., Nowotny, P., Hinrichs, A. L., Smemo, S., Kauwe, J. S., Maxwell, T. J., Cherny, S., Doil, L., et al. (2006). A scan of chromosome 10 identifies a novel locus showing strong association with late-onset Alzheimer disease. Am J Hum Genet. 78, 78-88.

Guo, Q., Xie, J., Chang, X., and Du, H. (2001). Prostate apoptosis response-4 enhances secretion of amyloid beta peptide 1-42 in human neuroblastoma IMR-32 cells by a caspase-dependent pathway. J Biol Chem 276, 16040-16044.

He, X., Chang, W. P., Koelsch, G., and Tang, J. (2002). Memapsin 2 (beta-secretase) cytosolic domain binds to the VHS domains of GGA1 and GGA2: implications on the endocytosis mechanism of memapsin 2. FEBS Lett 524, 183-187.

He, X., Li, F., Chang, W. P., and Tang, J. (2005). GGA proteins mediate the recycling pathway of memapsin 2 (BACE). J Biol. Chem.

He, X., Zhu, G., Koelsch, G., Rodgers, K. K., Zhang, X. C., and Tang, J. (2003). Biochemical and structural characterization of the interaction of memapsin 2 (beta-secretase) cytosolic domain with the VHS domain of GGA proteins. Biochemistry 42, 12174-12180.

Holsinger, R. M., McLean, C. A., Beyreuther, K., Masters, C. L., and Evin, G. (2002). Increased expression of the amyloid precursor beta-secretase in Alzheimer's disease. Ann Neurol 51, 783-786.

Honig, L. S., Tang, M. X., Albert, S., Costa, R., Luchsinger, J., Manly, J., Stern, Y., and Mayeux, R. (2003). Stroke and the risk of Alzheimer disease. Arch Neurol 60, 1707-1712.

Huse, J. T., Pijak, D. S., Leslie, G. J., Lee, V. M., and Doms, R. W. (2000). Maturation and endosomal targeting of beta-site amyloid precursor protein-cleaving enzyme. The Alzheimer's disease beta-secretase. J Biol Chem 275, 33729-33737.

Kalaria, R. N. (2000). The role of cerebral ischemia in Alzheimer's disease. Neurobiol Aging 21, 321-330.

Kalaria, R. N., Bhatti, S. U., Palatinsky, E. A., Pennington, D. H., Shelton, E. R., Chan, H. W., Perry, G., and Lust, W. D. (1993). Accumulation of the beta amyloid precursor protein at sites of ischemic injury in rat brain. Neuroreport 4, 211-214.

Kim, H. S., Lee, S. H., Kim, S. S., Kim, Y. K., Jeong, S. J., Ma, J., Han, D. H., Cho, B. K., and Suh, Y. H. (1998). Post-ischemic changes in the expression of Alzheimer's APP isoforms in rat cerebral cortex. Neuroreport 9, 533-537.

Koh, Y. H., Suzuki, K., Che, W., Park, Y. S., Miyamoto, Y., Higashiyama, S., and Taniguchi, N. (2001). Inactivation of glutathione peroxidase by NO leads to the accumulation of H2O2 and the induction of HB-EGF via c-Jun NH2-terminal kinase in rat aortic smooth muscle cells. Faseb J 15, 1472-1474.

Koh, Y. H., von Arnim, C. A., Hyman, B. T., Tanzi, R. E., and Tesco, G. (2005). BACE is degraded via the lysosomal pathway. J Biol Chem 280, 32499-32504.

Koistinaho, J., Pyykonen, I., Keinanen, R., and Hokfelt, T. (1996). Expression of beta amyloid precursor protein mRNAs following transient focal ischaemia. Neuroreport 7, 2727-2731.

Lane, J. D., Lucocq, J., Pryde, J., Barr, F. A., Woodman, P. G., Allan, V. J., and Lowe, M. (2002). Caspase-mediated cleavage of the stacking protein GRASP65 is required for Golgi fragmentation during apoptosis. J Cell Biol 156, 495-509.

LeBlanc, A. (1995). Increased production of 4 kDa amyloid beta peptide in serum deprived human primary neuron cultures: possible involvement of apoptosis. J Neurosci 15, 7837-7846.

LeBlanc, A., Liu, H., Goodyer, C., Bergeron, C., and Hammond, J. (1999). Caspase-6 role in apoptosis of human neurons, amyloidogenesis, and Alzheimer's disease. J Biol Chem 274, 23426-23436.

LeBlanc, A. C. (2005). The role of apoptotic pathways in Alzheimer's disease neurodegeneration and cell death. Curr Alzheimer Res 2, 389-402.

Li, R., Lindholm, K., Yang, L. B., Yue, X., Citron, M., Yan, R., Beach, T., Sue, L., Sabbagh, M., Cai, H., et al. (2004a). Amyloid beta peptide load is correlated with increased beta-secretase activity in sporadic Alzheimer's disease patients. Proc Natl Acad Sci USA 101, 3632-3637.

Li, Y., Nowotny, P., Holmans, P., Smemo, S., Kauwe, J. S., Hinrichs, A. L., Tacey, K., Doil, L., van Luchene, R., Garcia, V., et al. (2004b). Association of late-onset Alzheimer's disease with genetic variation in multiple members of the GAPD gene family. Proc Natl Acad Sci USA 101, 15688-15693.

Li, Y., Grupe, A., Rowland, C., Nowotny, P., Kauwe, J. S., Smemo, S., Hinrichs, A., Tacey, K., Toombs, T. A., Kwok, S., et al. (2006). DAPK1 variants are associated with Alzheimer's disease and allele-specific expression. Hum Mol Genet. 15, 2560-2568.

Liu, R., Yang, S. H., Perez, E., Yi, K. D., Wu, S. S., Eberst, K., Prokai, L., Prokai-Tatrai, K., Cai, Z. Y., Covey, D. F., et al. (2002). Neuroprotective effects of a novel non-receptorbinding estrogen analogue: in vitro and in vivo analysis. Stroke 33, 2485-2491.

Namura, S., Zhu, J., Fink, K., Endres, M., Srinivasan, A., Tomaselli, K. J., Yuan, J., and Moskowitz, M. A. (1998). Activation and cleavage of caspase-3 in apoptosis induced by experimental cerebral ischemia. J Neurosci 18, 3659-3668.

Nolan, K. A., Lino, M. M., Seligmann, A. W., and Blass, J. P. (1998). Absence of vascular dementia in an autopsy series from a dementia clinic. J Am Geriatr Soc 46, 597-604.

Pastorino, L., Ikin, A. F., Nairn, A. C., Pursnani, A., and Buxbaum, J. D. (2002). The carboxyl-terminus of BACE contains a sorting signal that regulates BACE trafficking but not the formation of total A(beta). Mol Cell Neurosci 19, 175-185.

Pellegrini, L., Passer, B. J., Tabaton, M., Ganjei, J. K., and D'Adamio, L. (1999). Alternative, non-secretase processing of Alzheimer's beta-amyloid precursor protein during apoptosis by caspase-6 and -8. J Biol Chem 274, 21011-21016.

Petrovitch, H., Ross, G. W., Steinhorn, S. C., Abbott, R. D., Markesbery, W., Davis, D., Nelson, J., Hardman, J., Masaki, K., Vogt, M. R., et al. (2005). AD lesions and infarcts in demented and non-demented Japanese-American men. Ann Neurol 57, 98-103.

Puertollano, R., and Bonifacino, J. S. (2004). Interactions of GGA3 with the ubiquitin sorting machinery. Nat Cell Biol 6, 244-251.

Puertollano, R., Randazzo, P. A., Presley, J. F., Hartnell, L. M., and Bonifacino, J. S. (2001). The GGAs promote ARF-dependent recruitment of clathrin to the TGN. Cell 105, 93-102.

Qing, H., Zhou, W., Christensen, M. A., Sun, X., Tong, Y., and Song, W. (2004). Degradation of BACE by the ubiquitin-proteasome pathway. Faseb J.

Riekse, R. G., Leverenz, J. B., McCormick, W., Bowen, J. D., Teri, L., Nochlin, D., Simpson, K., Eugenio, C., Larson, E. B., and Tsuang, D. (2004). Effect of vascular lesions on cognition in Alzheimer's disease: a community-based study. J Am Geriatr Soc 52, 1442-1448.

Rippon, G. A., Tang, M. X., Lee, J. H., Lantigua, R., Medrano, M., and Mayeux, R. (2006). Familial Alzheimer disease in Latinos: interaction between APOE, stroke, and estrogen replacement. Neurology 66, 35-40.

Sena-Esteves, M., Tebbets, J. C., Steffens, S., Crombleholme, T., and Flake, A. W. (2004). Optimized large-scale production of high titer lentivirus vector pseudotypes. J Virol Methods 122, 131-139.

Shi, J., Yang, S. H., Stubley, L., Day, A. L., and Simpkins, J. W. (2000). Hypoperfusion induces overexpression of beta-amyloid precursor protein mRNA in a focal ischemic rodent model. Brain Res 853, 1-4.

Shiba, T., Kametaka, S., Kawasaki, M., Shibata, M., Waguri, S., Uchiyama, Y., and Wakatsuki, S. (2004). Insights into the phosphoregulation of beta-secretase sorting signal by the VHS domain of GGA1. Traffic 5, 437-448.

Sinha, S., Anderson, J. P., Barbour, R., Basi, G. S., Caccavello, R., Davis, D., Doan, M., Dovey, H. F., Frigon, N., Hong, J., et al. (1999). Purification and cloning of amyloid precursor protein beta-secretase from human brain. Nature 402, 537-540.

Snowdon, D. A., Greiner, L. H., Mortimer, J. A., Riley, K. P., Greiner, P. A., and Markesbery, W. R. (1997). Brain infarction and the clinical expression of Alzheimer disease. The Nun Study [see comments]. Jama 277, 813-817.

Sodhi, C. P., Rampalli, S., Perez, R. G., Koo, E. H., Quinn, B., and Gottardi-Littell, N. R. (2004). The endocytotic pathway is required for increased A beta 42 secretion during apoptosis. Brain Res Mol Brain Res 128, 201-211.

Stephenson, D. T., Rash, K., and Clemens, J. A. (1992). Amyloid precursor protein accumulates in regions of neurodegeneration following focal cerebral ischemia in the rat. Brain Res 593, 128-135.

Tamagno, E., Bardini, P., Obbili, A., Vitali, A., Borghi, R., Zaccheo, D., Pronzato, M. A., Danni, O., Smith, M. A., Perry, G., and Tabaton, M. (2002). Oxidative stress increases expression and activity of BACE in NT2 neurons. Neurobiol Dis 10, 279-288.

Tamagno, E., Guglielmotto, M., Bardini, P., Santoro, G., Davit, A., Di Simone, D., Danni, O., and Tabaton, M. (2003). Dehydroepiandrosterone reduces expression and activity of BACE in NT2 neurons exposed to oxidative stress. Neurobiol Dis 14, 291-301.

Tamagno, E., Parola, M., Bardini, P., Piccini, A., Borghi, R., Guglielmotto, M., Santoro, G., Davit, A., Danni, O., Smith, M. A., et al. (2005). Beta-site APP cleaving enzyme upregulation induced by 4-hydroxynonenal is mediated by stress-activated protein kinases pathways. J Neurochem 92, 628-636.

Tesco, G., Koh, Y. H., and Tanzi, R. E. (2003). Caspase activation increases beta-amyloid generation independently of caspase cleavage of the beta-amyloid precursor protein (APP). J Biol Chem 278, 46074-46080.

Tong, Y., Zhou, W., Fung, V., Christensen, M. A., Qing, H., Sun, X., and Song, W. (2005). Oxidative stress potentiates BACE1 gene expression and Abeta generation. J Neural Transm 112, 455-469.

Tyler, S. J., Dawbarn, D., Wilcock, G. K., and Allen, S. J. (2002). alpha- and betasecretase: profound changes in Alzheimer's disease. Biochem Biophys Res Commun 299, 373-376.

Vassar, R., Bennett, B. D., Babu-Khan, S., Kahn, S., Mendiaz, E. A., Denis, P., Teplow, D. B., Ross, S., Amarante, P., Loeloff, R., et al. (1999). Beta-secretase cleavage of Alzheimer's amyloid precursor protein by the transmembrane aspartic protease BACE. Science 286, 735-741.

Velliquette, R. A., O'Connor, T., and Vassar, R. (2005). Energy inhibition elevates beta-secretase levels and activity and is potentially amyloidogenic in APP transgenic mice: possible early events in Alzheimer's disease pathogenesis. J Neurosci 25, 10874-10883.

von Arnim, C. A., Tangredi, M. M., Peltan, I. D., Lee, B. M., Irizarry, M. C., Kinoshita, A., and Hyman, B. T. (2004). Demonstration of BACE (beta-secretase) phosphorylation and its interaction with GGA1 in cells by fluorescence-lifetime imaging microscopy. J Cell Sci 117, 5437-5445.

Wahle, T., Prager, K., Raffler, N., Haass, C., Famulok, M., and Walter, J. (2005). GGA proteins regulate retrograde transport of BACE1 from endosomes to the trans-Golgi network. Mol Cell Neurosci 29, 453-461.

Wakita, H., Tomimoto, H., Akiguchi, I., Ohnishi, K., Nakamura, S., and Kimura, J. (1992). Regional accumulation of amyloid beta/A4 protein precursor in the gerbil brain following transient cerebral ischemia. Neurosci Lett 146, 135-138.

Weidemann, A., Paliga, K., Durrwang, U., Reinhard, F. B., Schuckert, O., Evin, G., and Masters, C. L. (1999). Proteolytic processing of the Alzheimer's disease amyloid precursor protein within its cytoplasmic domain by caspase-like proteases. J Biol Chem 274, 5823-5829.

Wen, Y., Onyewuchi, O., Yang, S., Liu, R., and Simpkins, J. W. (2004). Increased beta-secretase activity and expression in rats following transient cerebral ischemia. Brain Res 1009, 1-8.

Yan, R., Bienkowski, M. J., Shuck, M. E., Miao, H., Tory, M. C., Pauley, A. M., Brashier, J. R., Stratman, N. C., Mathews, W. R., Buhl, A. E., et al. (1999). Membrane-anchored aspartyl protease with Alzheimer's disease beta-secretase activity. Nature 402, 533-537.

Yang, L. B., Lindholm, K., Yan, R., Citron, M., Xia, W., Yang, X. L., Beach, T., Sue, L., Wong, P., Price, D., et al. (2003). Elevated beta-secretase expression and enzymatic activity detected in sporadic Alzheimer disease. Nat Med 9, 3-4.

Zlokovic, B. V. (2002). Vascular disorder in Alzheimer's disease: role in pathogenesis of dementia and therapeutic targets. Adv Drug Deliv Rev 54, 1553-1559.

EQUIVALENTS

Those skilled in the art will recognize, or be able to ascertain using no more than routine experimentation, many equivalents to the specific embodiments of the invention described herein. Such equivalents are intended to be encompassed by the following claims.

All references, including patent documents, disclosed herein are incorporated by reference in their entirety.

We claim:

1. A method for diagnosing a disorder associated with altered β-secretase processing of substrates, comprising
measuring the stability of a GGA protein in a biological sample from a subject, wherein decreased protein stability relative to that in a control biological sample is an indication that the subject has a disorder associated with altered β-secretase processing of substrates, wherein the disorder associated with altered β-secretase processing of substrates is an Aβ-accumulation-associated disorder.

2. The method of claim 1, wherein the disorder is a neurological disease or disorder.

3. The method of claim 1, wherein the disorder is selected from the group consisting of Alzheimer's disease, Down's syndrome, cerebrovascular amyloidosis, diseases associated with abnormal BACE activity, ischemia, oxidative stress, and stroke.

4. The method of claim 1, wherein the GGA protein is GGA1, GGA2 or GGA3.

5. The method of claim 4, wherein the GGA protein is GGA3.

6. The method of claim 1, wherein the subject is human.

7. The method of claim 1, wherein the subject is at risk of developing Alzheimer's disease.

8. The method of claim 1, wherein the biological sample is selected from the group consisting of cells and tissues.

9. The method of claim 8, wherein the cells are neuronal cells.

10. The method of claim 8, wherein the tissue comprises neuronal cells.

11. A method for determining onset, progression, or regression, of a disorder associated with altered β-secretase processing of substrates in a subject, comprising:
measuring the stability of a GGA protein in a first biological sample of a subject,
measuring the stability of the GGA protein in a second biological sample of a subject obtained at a second time, and
comparing the measurement of stability in the first sample to the measurement of stability in the second sample as a determination of the onset, progression, or regression of the disorder associated with altered β-secretase processing of substrates, wherein the disorder associated with altered β-secretase processing of substrates is an Aβ-accumulation-associated disorder.

12. The method of claim 11, wherein the disorder is a neurological disease or disorder.

13. The method of claim 11, wherein the disorder is selected from the group consisting of Alzheimer's disease, Down's syndrome, cerebrovascular amyloidosis, diseases associated with abnormal BACE activity, ischemia, oxidative stress, and stroke.

14. The method of claim 11, wherein the GGA protein is GGA1, GGA2 or GGA3.

15. The method of claim 14, wherein the GGA protein is GGA3.

16. The method of claim 11, wherein the subject is human.

17. The method of claim 11, wherein the subject has been diagnosed with Alzheimer's disease or is at risk of developing Alzheimer's disease.

18. The method of claim 11, wherein the biological sample is selected from the group consisting of cells and tissues.

19. The method of claim 18, wherein the cells are neuronal cells.

20. The method of claim 18, wherein the tissue comprises neuronal cells.

* * * * *